(12) United States Patent
Mason et al.

(10) Patent No.: US 8,252,574 B2
(45) Date of Patent: Aug. 28, 2012

(54) **PSEUDOINFECTIOUS *FLAVIVIRUS* AND USES THEREOF**

(75) Inventors: Peter W. Mason, Galveston, TX (US);
Elena Frolova, Galveston, TX (US);
Ilya Frolov, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 512 days.

(21) Appl. No.: 11/711,532

(22) Filed: Feb. 27, 2007

(65) Prior Publication Data

US 2009/0155301 A1    Jun. 18, 2009

Related U.S. Application Data

(60) Provisional application No. 60/777,189, filed on Feb. 27, 2006.

(51) Int. Cl.
*C12N 7/00* (2006.01)
*A61K 39/12* (2006.01)

(52) U.S. Cl. ............... 435/235.1; 424/218.1; 424/205.1

(58) Field of Classification Search ........................ None
See application file for complete search history.

(56) References Cited

FOREIGN PATENT DOCUMENTS

| WO | WO 02/72803 A2 | 2/2002 |
|---|---|---|
| WO | WO 2006/017206 A2 | 2/2006 |

OTHER PUBLICATIONS

Kofler et al. Journal of Virology, 2003, 77(1):443-451.*
Aberle et al. Journal of Virology, 2005, 79(24):15107-15113.*
Jones et al., Journal of Virology, 2003, 77(12):7143-7149.*
Mandl, et al. *Flavivirus* Immunization with Capsid-Deletion Mutants: Basics, Benefits and Barriers: *Viral Immunology*, 2004, vol. 17, No. 4, p. 461-472.
Harvey, et al. Tetracycline-Inducible Packaging Cell Line for Production of *Flavivirus* Replicon Particles: *Journal of Virology*, Jan. 2004, vol. 78, No. 1, p. 531-538.

* cited by examiner

*Primary Examiner* — Stacy B. Chen

(57) ABSTRACT

The present invention discloses a replication-deficient pseudoinfective virus belonging to the Flaviviridae family that lack the capsid gene, where the replication-deficient pseudoinfective virus propagates only in cells expressing the capsid or capsid, prM and envelope protein of the flavivirus. The present also discloses the method of producing such viruses on a large scale and the use of these pseudoinfective viruses as vaccines for preventing diseases caused by infections of humans or animals by the viruses belonging to this family.

25 Claims, 29 Drawing Sheets

Fig.1

YFV genome

| C | prM | E | NS1 | 2A | 2B | NS3 | 4A | 4B | NS5 |

YF PIV genome

| GFP | prM | E | NS1 | 2A | 2B | NS3 | 4A | 4B | NS5 |

Fig.2A

VEErep/C1/Pac

| nsP1 | nsP2 | nsP3 | nsP4 | C | Pac |

VEErep/C2/Pac

| nsP1 | nsP2 | nsP3 | nsP4 | C | Pac |

VEErep/C-prM-E/Pac

| nsP1 | nsP2 | nsP3 | nsP4 | C | prM | E | Pac |

ATGagcGGccGgaAgGCTcAGGGcaAGgaCCCTgGGGCgCagGCCTcTCcAACAAg
ATcAAgCAgaAgaCCaAgCTgatCcGGcaAGaCCgCaAcAgaACCgagccGGcGgCGTccAGaGGCCGtccAtCTTcTTcTTccTG
TTcAAcATccTcACaGGtAAgaAgATCACgGCtCACCTgAAgAGaCGcTctGCCTgAAgATGCTggACCCTcTgGGctTc
GCggTgCTcAGaAAgGTgAACGgggtCgCTgCCtccCTgTCTcTgCCAgaAtGCTgGGCtGgcTgAGgCTGcTCcCAgGAT
GTgCTcAccGTcCAAgTGctgCAATTCCTcATTcTGGAATGCtgCTgATGACtGCGGcGGTgACtgGgGGCAAgAACcGcTGG
cTGCTgcTTgAATGTGACcagTGAGGACCCTCGG SEQ ID NO: 1

WN PIV genome delC — prM | E | NS1 | 2A | 2B | NS3 | 4A | 4B | NS5

VEErep/C*-E*-Pac nsP1 | nsP2 | nsP3 | nsP4 — C | prM | E | Pac delNS1 delNS2b
2A FMDV Fig. 5B          Fig. 5C

Top                                    Bottom

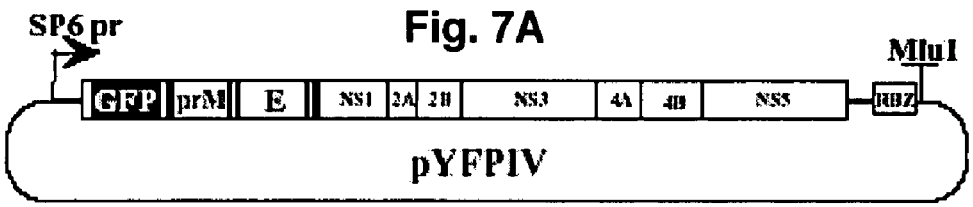
Fig. 7A
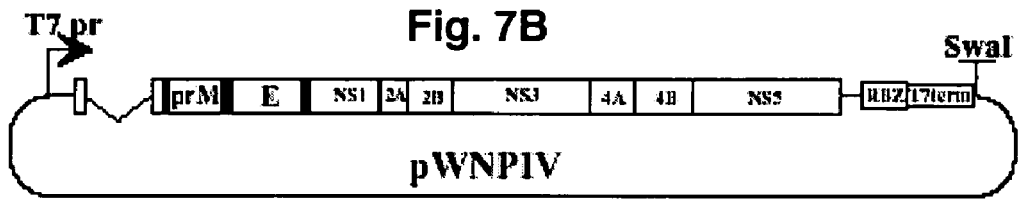
Fig. 7B
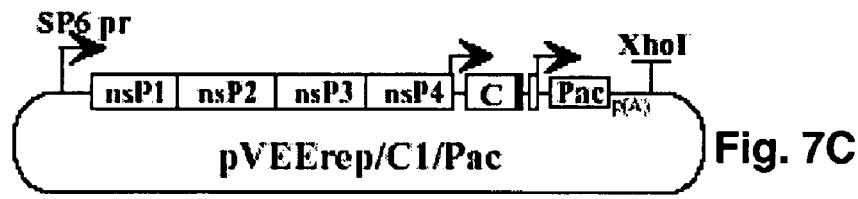
Fig. 7C
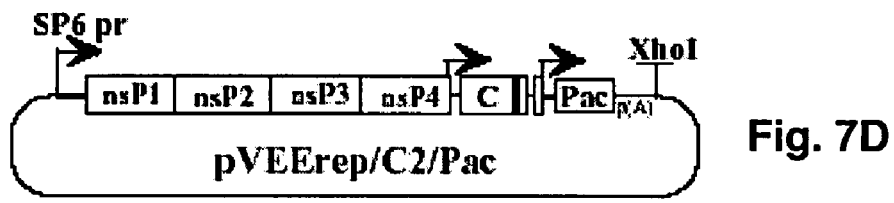
Fig. 7D
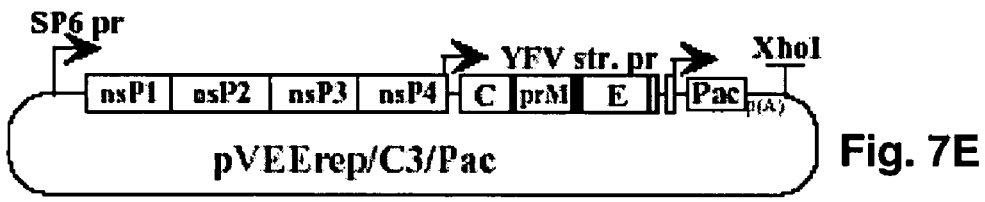
Fig. 7E
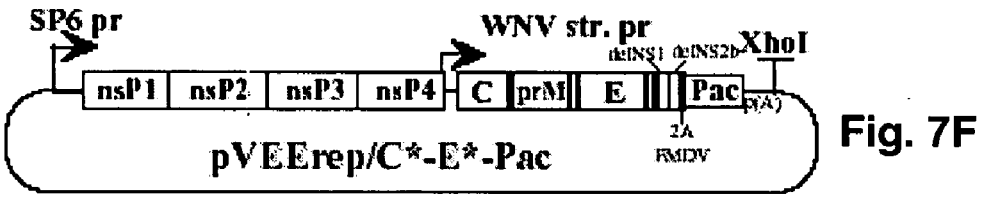

gagtaaatcctgtgtgctaattgaggtgcattggtctgcaaatcgagttgctaggcaataaacacatttggattaattttaatcgt
tcgttgagcgattagcagagaactgaccagaacatgtctggtcgtaaagctcagggaaaaaccctgggcgtcaatatggt
acgacgaggagttcgctccttgtcaaacaccatggtgagcaagggcgaggagctgttcaccggggtggtgcccatcctgg
tcgagctggacggcgacgtaaacggccacaagttcagcgtgtccggcgagggcgagggcgatgccacctacggcaag
ctgaccctgaagttcatctgcaccaccggcaagctgcccgtgccctggcccaccctcgtgaccaccctgacctacggcgtg
cagtgcttcagccgctaccccgaccacatgaagcagcacgacttcttcaagtccgccatgcccgaaggctacgtccagga
gcgcaccatcttcttcaaggacgacggcaactacaagacccgcgccgaggtgaagttcgagggcgacaccctggtgaa
ccgcatcgagctgaagggcatcgacttcaaggaggacggcaacatcctggggcacaagctggagtacaactacaaca
gccacaacgtctatatcatggccgacaagcagaagaacggcatcaaggtgaacttcaagatccgccacaacatcgagg
acggcagcgtgcagctcgccgaccactaccagcagaacacccccatcggcgacggccccgtgctgctgcccgacaac
cactacctgagcacccagtccgccctgagcaaagaccccaacgagaagcgcgatcacatggtcctgctggagttcgtga
ccgccgccgggatcactctcggcatggacgagctgtacaagcttggattgtcctcaaggaaacgccgttcccatgatgttct
gactgtgcaattcctaattttgggaatgctgttgatgacgggtggagtgaccttggtgcggaaaaacagatggttgctcctaa
atgtgacatctgaggacctcgggaaaacattctctgtgggcacaggcaactgcacaacaaacattttggaagccaagtact
ggtgcccagactcaatggaatacaactgtcccaatctcagtccaagagaggagccagatgacattgattgctggtgctatg
gggtggaaaacgttagagtcgcatatggtaagtgtgactcagcaggcaggtctaggaggtcaagaagggccattgacttg
cctacgcatgaaaaccatggtttgaagacccggcaagaaaaatggatgactggaagaatgggtgaaaggcaactccaa
aagattgagagatggttcgtgaggaaccccttttttgcagtgacggctctgaccattgcctaccttgtgggaagcaacatgac
gcaacgagtcgtgattgccctactggtcttggctgttggtccggcctactcagctcactgcattggaattactgacagggatttc
attgaggggtgcatggaggaacttgggtttcagctaccctggagcaagacaagtgtgtcactgttatggcccctgacaag
ccttcattggacatctcactagagacagtagccattgatagacctgctgaggtgaggaaagtgtgttacaatgcagttctcac
tcatgtgaagattaatgacaagtgccccagcactggagagggcccacctagctgaagagaacgaaggggacaatgcgtg
caagcgcacttattctgatagaggctggggcaatggctgtggcctatttgggaaagggagcattgtggcatgcgccaaattc
acttgtgccaaatccatgagtttgtttgaggttgatcagaccaaaattcagtatgtcatcagagcacaattgcatgtaggggcc
aagcaggaaaattggaataccgacattaagactctcaagtttgatgccctgtcaggctcccaggaagtcgagttcattgggt
atggaaaagctacactggaatgccaggtgcaaactgcggtggactttggtaacagttacatcgctgagatggaaacagag
agctggatagtggacagacagtgggcccaggacttgaccctgccatggcagagtggaagtggcggggtgtggagagag
atgcatcatcttgtcgaatttgaacctccgcatgccgccactatcagagtactggccctgggaaaccaggaaggctccttga
aaacagctcttactggcgcaatgaggggttacaaaggacacaaatgacaacaaccctttacaaactacatggtggacatgttt
cttgcagagtgaaattgtcagctttgacactcaaggggacatcctacaaaatatgcactgacaaaatgttttttgtcaagaac
ccaactgacactggccatggcactgttgtgatgcaggtgaaagtgtcaaaaggagccccctgcaggattccagtgatagta
gctgatgatcttacagcggcaatcaataaaggcatttggttacagttaacccatcgcctcaaccaatgatgatgaagtgct
gattgaggtgaacccacctttttggagacagctacattatcgttgggagaggagattcacgtctcacttaccagtggcacaaa
gagggaagctcaataggaaagttgttcactcagaccatgaaaggcgtggaacgcctggccgtcatgggagacaccgcct
gggatttcagctccgctggagggttcttcacttcggttgggaaaggaattcatacggtgtttggctctgcctttcaggggctattt
ggcggcttgaactggataacaaaggtcatcatggggggcggtacttatatggggttggcatcaacacaagaaacatgacaat
gtccatgagcatgatcttggtaggagtgatcatgatgttttgtctctaggagttggggcggatcaaggatgcgccatcaacttt
ggcaagagagagctcaagtgcggagatggtatcttcatatttagagactctgatgactggctgaacaagtactcatactatc
cagaagatcctgtgaagcttgcatcaatagtgaaagcctcttttgaagaagggaagtgtggcctaaattcagttgactccctt
gagcatgagatgtggagaagcagggcagatgagatcaatgccattttgaggaaaacgaggtggacatttctgttgtcgtg
caggatccaaagaatgtttaccagagaggaactcatccattttccagaattcgggatggtctgcagtatggttggaagacttg
gggtaagaaccttgtgttctccccagggaggaagaatggaagcttcatcatagatggaaagtccaggaaagaatgcccgt
tttcaaaccgggtctggaattctttccagatagaggagtttgggacgggagtgttcaccacacgcgtgtacatggacgcagt
ctttgaatacaccatagactgcgatggatctatcttgggtgcagcggtgaacggaaaaaagagtgcccatggctctccaac
attttggatgggaagtcatgaagtaaatgggacatggatgatccacaccttggaggcattagattacaaggagtgtgagtgg
ccactgacacatacgattggaacatcagttgaagagagtgaaatgttcatgccgagatcaatcggaggcccagttagctct
cacaatcatatccctggatacaaggttcagacgaacggaccttggatgcaggtaccactagaagtgaagagagaagctt
gcccagggactagcgtgatcattgatggcaactgtgatggacggggaaaatcaaccagatccaccacggatagcggga
aagttattcctgaatggtgttgccgctcctgcacaatgccgcctgtgagcttccatggtagtgatgggtgttggtatcccatgga
aattaggccaaggaaaacgcatgaaagccatctggtgcgctcctgggttacagctggagaaatacatgctgtcccttttggt ttggtgagcatgatgatagcaatggaagtggtcctaaggaaaagacagggaccaaagcaaatgttggttggaggagtag
tgctcttgggagcaatgctggtcgggcaagtaactctccttgatttgctgaaactcacagtggctgtgggattgcatttccatga
gatgaacaatggaggagacgccatgtatatggcgttgattgctgccttttcaatcagaccagggctgctcatcggctttgggc
tcaggaccctatggagccctcgggaacgccttgtgctgacccctaggagcagccatggtggagattgccttgggtggcgtga
tgggcggcctgtggaagtatctaaatgcagtttctctctgcatcctgacaataaatgctgttgcttctaggaaagcatcaaata
ccatcttgcccctcatggctctgttgacacctgtcactatggctgaggtgagacttgccgcaatgttcttttgtgccgtggttatcat
aggggtccttcaccagaatttcaaggacacctccatgcagaagactatacctctggtggccctcacactcacatcttacctg
ggcttgacacaaccttttttgggcctgtgtgcatttctggcaacccgcatatttgggcgaaggagtatcccagtgaatgaggca
ctcgcagcagctggtctagtgggagtgctggcaggactggcttttcaggagatggagaacttccttggtccgattgcagttgg
aggactcctgatgatgctggttagcgtggctgggagggtggatgggctagagctcaagaagcttggtgaagtttcatggga
agaggaggcggagatcagcgggagttccgcccgctatgatgtggcactcagtgaacaaggggagttcaagctgctttctg
aagagaaagtgccatgggaccaggttgtgatgacctcgctggccttggttggggctgccctccatccatttgctcttctgctgg
tccttgctgggtggctgtttcatgtcaggggagctaggagaagtggggatgtcttgtgggatattcccactcctaagatcatcg
aggaatgtgaacatctggaggatgggatttatggcatattccagtcaaccttcttgggggcctcccagcgaggagtgggagt
ggcacagggagggggtgttccacacaatgtggcatgtcacaagaggagctttccttgtcaggaatggcaagaagttgattcc
atcttgggcttcagtaaaggaagaccttgtcgcctatggtggctcatggaagttggaaggcagatgggatggagaggaag
aggtccagttgatcgcggctgttccaggaaagaacgtggtcaacgtccagacaaaaccgagcttgttcaaagtgaggaat
gggggagaaatcggggctgtcgctcttgactatccgagtggcacttcaggatctcctattgttaacaggaacggagaggtg
attgggctgtacggcaatggcatccttgtcggtgacaactccttcgtgtccgccatatcccagactgaggtgaaggaagaag
gaaaggaggagctccaagagatcccgacaatgctaaagaaaggaatgacaactgtccttgattttcatcctggagctggg
aagacaagacgtttcctcccacagatcttggccgagtgcgcacggagacgcttgcgcactcttgtgttggcccccaccagg
gttgttctttctgaaatgaaggaggcttttcacgccctggacgtgaaattccacacacaggcttttccgctcacggcagcggg
agagaagtcattgatgccatgtgccatgccacccctaacttacaggatgttggaaccaactagggttgttaactgggaagtga
tcattatggatgaagcccatttttttggatccagctagcatagccgctagaggttgggcagcgcacagagctagggcaaatg
aaagtgcaacaatcttgatgacagccacaccgcctgggactagtgatgaatttccacattcaaatggtgaaatagaagatg
ttcaaacggacatacccagtgagccctggaacacagggcatgactggatcctagctgacaaaaggcccacggcatggtt
ccttccatccatcagagctgcaaatgtcatggcgcctctttgcgtaaggctggaaagagtgtggtggtcctgaacaggaaaa
cctttgagagagaatacccccacgataaagcagaagaaacctgactttatattggccactgacatagctgaaatgggagcc
aacctttgcgtggagcgagtgctggattgcaggacggcttttaagcctgtgcttgtggatgaagggaggaaggtggcaata
aaagggccacttcgtatctccgcatcctctgctgctcaaaggaggggcgcattgggagaaatcccaacagagatggag
actcatactactattctgagcctacaagtgaaaataatgcccaccacgtctgctggttggaggcctcaatgctcttggacaac
atggaggtgaggggtggaatggtcgcccactctatggcgttgaaggaactaaaacaccagtttcccctggtgaaatgag
actgagggatgaccagaggaaagtcttcagagaactagtgaggaattgtgacctgcccgtttggctttcgtggcaagtggc
caaggctggtttgaagacgaatgatcgtaagtggtgttttgaaggccctgaggaacatgagatcttgaatgacagcggtga
aacagtgaagtgcagggctcctggaggagcaaagaagcctctgcgcccaaggtggtgtgatgaaagggtgtcatctgac
cagagtgcgctgtctgaatttattaagtttgctgaaggtaggaggggagctgctgaagtgctagttgtgctgagtgaactccct
gatttcctggctaaaaaaggtggagaggcaatggataccatcagtgtgttcctccactctgaggaaggctctagggcttacc
gcaatgcactatcaatgatgcctgaggcaatgacaatagtcatgctgtttatactggctggactactgacatcgggaatggtc
atcttttcatgtctcccaaaggcatcagtagaatgtctatggcgatgggcacaatggccggctgtggatatctcatgttccttgg
aggcgtcaaacccactcacatctcctatgtcatgctcatattctttgtcctgatggtggttgtgatccccgagccagggcaaca
aaggtccatccaagacaaccaagtggcatacctcattattggcatcctgacgctggtttcagcggtggcagccaacgagct
aggcatgctggagaaaaccaaagaggacctctttgggaagaagaacttaattccatcagtgcttcaccctggagttggcc
ggatcttgacctgaagccaggagctgcctggacagtgtacgttggcattgttacaatgctctctccaatgttgcaccactggat
caaagtcgaatatggcaacctgtctctgtctggaatagcccagtcagcctcagtcctttctttcatggacaaggggataccatt
catgaagatgaatatctcggtcataatgctgctggtcagtggctggaattcaataacagtgatgcctctgctctgtggcatagg
gtgcgccatgctccactggtctctcatttacctggaatcaaagcgcagcagtcaaagcttgcacagagaagggtgttccat
ggcgttgccgagaaccctgtggttgatgggaatccaacagttgacattgaggaagctcctgaaatgcctgcccttatgaga
agaaactggctctatatctccttcttgctctcagcctagcttctgttgccatgtgcagaacgcccttttcattggctgaaggcattgt
cctagcatcagctgccttagggccgctcatagagggaaacaccagccttctttggaatggacccatggctgtctccatgaca
ggagtcatgaggggaatcactatgctttgtgggagtcatgtacaatctatggaagatgaaaactggacgccgggggag
cgcgaatggaaaaactttgggtgaagtctggaagagggaactgaatctgttggacaagcgacagtttgagttgtataaaag gaccgacattgtggaggtggatcgtgatacggcacgcaggcatttggccgaagggaaggtggacaccggggtggcggt
ctccagggggaccgcaaagttaaggtggttccatgagcgtggctatgtcaagctggaaggtagggtgattgacctggggtg
tggccgcggaggctggtgttactacgctgctgcgcaaaaggaagtgagtggggtcaaaggatttactcttggaagagacg
gccatgagaaacccatgaatgtgcaaagtctgggatggaacatcatcaccttcaaggacaaaactgtatatccaccgccta
gaaccagtgaaatgtgacacccttttgtgtgacattggagagtcatcatcgtcatcggtcacagaggggggaaaggaccgtg
agagttcttgatactgtagaaaaatggctggcttgtggggttgacaacttctgtgtgaaggtgttagctccatacatgccagat
gttcttgagaaactggaattgctccaaggaggtttggcggaacagtgatcaggaaccctctctccaggaattccactcatg
aaatgtactacgtgtctggagcccgcagcaatgtcacatttactgtgaaccaaacatcccgcctcctgatgaggagaatga
ggcgtccaactggaaaagtgaccctggaggctgacgtcatcctcccaattgggacacgcagtgttgagacagacaaggg
accccctggacaaagaggccatagaagaaagggttgagaggataaaatctgagtacatgacctcttggttttatgacaatg
acaaccccctacaggacctggcactactgtggctcctatgtcacaaaaacctcaggaagtgcggcgagcatggtaaatggt
gttattaaaattctgacatatccatgggacaggatagaggaggtcacaagaatggcaatgactgacacaacccccttttgga
cagcaaagagtgtttaaagaaaaagttgacaccagagcaaaggatccaccagcgggaactaggaagatcatgaaagt
tgtcaacaggtggctgttccgccacctggccagagaaaagaaccccagactgtgcacaaaggaagaatttattgcaaaa
gtccgaagtcatgcagccattggagcttacctggaagaacaagaacagtggaagactgccaatgaggctgtccaagacc
caaagttctgggaactggtggatgaagaaaggaagctgcaccaacaaggcaggtgtcggacttgtgtgtacaacatgat
ggggaaaagagagaagaagctgtcagagtttgggaaagcaaagggaagccgtgccatatggtatatgtggctgggagc
gcggtatcttgagtttgaggccctgggattcctgaatgaggaccattgggcttccagggaaaactcaggaggaggagtgga
aggcattggcttacaatacctaggatatgtgatcagagacctggctgcaatggatggtggtggattctacgcggatgacacc
gctggatgggacacgcgcatcacagaggcagaccttgatgatgaacaggagatcttgaactacatgagcccacatcaca
aaaaactggcacaagcagtgatggaaatgacatacaagaacaaagtggtgaaagtgttgagaccagccccaggagg
gaaagcctacatggatgtcataagtcgacgagaccagagaggatccgggcaggtagtgacttatgctctgaacaccatc
accaacttgaaagtccaattgatcagaatggcagaagcagagatggtgatacatcaccaacatgttcaagattgtgatgaa
tcagttctgaccaggctggaggcatggctcactgagcacggatgtgacagactgaagaggatggcggtgagtggagacg
actgtgtggtccggcccatcgatgacaggttcggcctggccctgtcccatctcaacgccatgtccaaggttagaaaggacat
atctgaatggcagccatcaaaagggtggaatgattgggagaatgtgcccttctgttcccaccacttccatgaactacagctg
aaggatggcaggaggattgtggtgccttgccgagaacaggacgagctcattgggagaggaagggtgtctccaggaaac
ggctggatgatcaaggaaacagcttgcctcagcaaagcctatgccaacatgtggtcactgatgtatttcacaaaagggac
atgaggctactgtcattggctgtttcctcagctgttcccacctcatgggttccacaaggacgcacaacatggtcgattcatggg
aaaggggagtggatgaccacggaagacatgcttgaggtgtggaacagagtatggataaccaacaacccacacatgca
ggacaagacaatggtgaaaaaatggagagatgtcccttatctaaccaagagacaagacaagctgtgcggatcactgatt
ggaatgaccaatagggccacctgggcctcccacatccatttagtcatccatcgtatccgaacgctgattggacaggagaa
atacactgactacctaacagtcatggacaggtattctgtggatgctgacctgcaactgggtgagcttatctgaaacaccatct
aacaggaataaccgggatacaaaccacgggtggagaaccggactccccacaacctgaaaccgggatataaaccacg
gctggagaaccggactccgcacttaaaatgaaacagaaaccgggataaaaactacggatggagaaccggactccaca
cattgagacagaagaagttgtcagcccagaaccccacacgagttttgccactgctaagctgtgaggcagtgcaggctggg
acagccgacctccaggttgcgaaaaacctggtttctgggacctccaccccagagtaaaagaacggagcctccgctac
caccctcccacgtggtggtagaaagacggggtctagaggttagaggagaccctccagggaacaaatagtgggaccata
ttgacgccagggaaagaccggagtggttctctgcttttcctccagaggtctgtgagcacagtttgctcaagaataagcagac
ctttggatgacaaacacaaaaccactgggtcggcatggcatctccacctcctcgcggtccgacctgggcatccgaaggag
gacgcacgtccactcggatggctaagggagagccacgagctcctcgacagatcataatcagccataccacatttgtaga
ggttttacttgctttaaaaaacctcccacacctcccctgaacctgaaacataaaatgaatgcaattgttgttgttaacttgtttatt
gcagcttataatggttacaaataaagcaatagcatcacaaatttcacaaataaagcatttttttcactgcattctagttgtggtttg
tccaaactcatcaagatctcgagcaagacgtttcccgttgaatatggctcataacacccccttgtattactgtttatgtaagcaga
cagttttattgttcatgatgatatattttatcttgtgcaatgtaacatcagagattttgagacacaacgtggctttgttgaataaatc
gaacttttgctgagttgaaggatcagatcacgcatcttcccgacaacgcagaccgttccgtggcaaagcaaaagttcaaaa
tcaccaactggtccacctacaacaaagctctcatcaaccgtggctccctcactttctggctggatgatggggcgattcaggc
ctggtatgagtcagcaacaccttcttcacgaggcagacctcagcgctagcggagtgtatactggcttactatgttggcactga
tgagggtgtcagtgaagtgcttcatgtggcaggagaaaaaggctgcaccggtgcgtcagcagaatatgtgatacaggat
atattccgcttcctcgctcactgactcgctacgctcggtcgttcgactgcggcgagcggaaatggcttacgaacggggcgga
gatttcctggaagatgccaggaagatacttaacagggaagtgagagggccgcggcaaagccgtttttccataggctccgc

Fig. 8C cccctgacaagcatcacgaaatctgacgctcaaatcagtggtggcgaaacccgacaggactataaagataccaggcg
tttccctggcggctccctcgtgcgctctcctgttcctgcctttcggtttaccggtgtcattccgctgttatggccgcgtttgtctcatt
ccacgcctgacactcagttccgggtaggcagttcgctccaagctggactgtatgcacgaacccccgttcagtccgaccgc
tgcgccttatccggtaactatcgtcttgagtccaacccggaaagacatgcaaaagcaccactggcagcagccactggtaat
tgatttagaggagttagtcttgaagtcatgcgccggttaaggctaaactgaaaggacaagttttggtgactgcgctcctccaa
gccagttacctcggttcaaagagttggtagctcagagaaccttcgaaaaaccgccctgcaaggcggttttttcgttttcagag
caagagattacgcgcagaccaaaacgatctcaagaagatcatcttattaaggggtctgacgctcagtggaacgaaaact
cacgttaagggattttggtcatgagattatcaaaaaggatcttcacctagatccttttaaattaaaaatgaagttttaaatcaatc
taaagtatatatgagtaaacttggtctgacagttaccaatgcttaatcagtgaggcacctatctcagcgatctgtctatttcgttc
atccatagttgcctgactccccgtcgtgtagataactacgatacgggagggcttaccatctggccccagtgctgcaatgatac
cgcgagacccacgctcaccggctccagatttatcagcaataaaccagccagccggaagggccgagcgcagaagtggt
cctgcaactttatccgcctccatccagtctattaattgttgccgggaagctagagtaagtagttcgccagttaatagtttgcgca
acgttgttgccattgctgcaggcatcgtggtgtcacgctcgtcgtttggtatggcttcattcagctccggttcccaacgatcaag
gcgagttacatgatcccccatgttgtgcaaaaaagcggttagctccttcggtcctccgatcgttgtcagaagtaagttggccg
cagtgttatcactcatggttatggcagcactgcataattctcttactgtcatgccatccgtaagatgcttttctgtgactggtgagta
ctcaaccaagtcattctgagaatagtgtatgcggcgaccgagttgctcttgcccggcgtcaacacgggataataccgcgcc
acatagcagaactttaaaagtgctcatcattggaaaacgttcttcggggcgaaaactctcaaggatcttaccgctgttgagat
ccagttcgatgtaacccactcgtgcacccaactgatcttcagcatcttttactttcaccagcgtttctgggtgagcaaaaacag
gaaggcaaaatgccgcaaaaaagggaataagggcgacacggaaatgttgaatactcatactcttcctttttcaatattattg
aagcatttatcagggttattgtctcatgagcggatacatatttgaatgtatttagaaaaataaacaaataggggttccgcgcac
atttccccgaaaagtgccacctgacgtgtcgacgcggccgctagcgatgaccctgctgattggttcgctgaccatttccgggt
gcgggacggcgttaccagaaactcagaaggttcgtccaaccaaaccgactctgacggcagtttacgagagagatgatag
ggtctgcttcagtaagccagatgctacacaattaggcttgtacatattgtcgttagaacgcggctacaattaatacataaccttt
atgtatcatacacatacgatttaggtgacactata (SEQ ID NO: 6)

Fig. 8D gatgggcggcgcatgagagaagcccagaccaattacctacccaaaatggagaaagttcacgttgacatcgaggaaga
cagcccattcctcagagctttgcagcggagcttcccgcagtttgaggtagaagccaagcaggtcactgataatgaccatgc
taatgccagagcgttttcgcatctggcttcaaaactgatcgaaacggaggtggacccatccgacacgatccttgacattgga
agtgcgcccgcccgcagaatgtattctaagcacaagtatcattgtatctgtccgatgagatgtgcggaagatccggacagat
tgtataagtatgcaactaagctgaagaaaaactgtaaggaaataactgataaggaattggacaagaaaatgaaggagct
ggccgccgtcatgagcgaccctgacctggaaactgagactatgtgcctccacgacgacgagtcgtgtcgctacgaaggg
caagtcgctgtttaccaggatgtatacgcggttgacggaccgacaagtctctatcaccaagccaataagggagttagagtc
gcctactggataggctttgacaccaccccttttatgtttaagaacttggctggagcatatccatcatactctaccaactgggccg
acgaaaccgtgttaacggctcgtaacataggcctatgcagctctgacgttatggagcggtcacgtagagggatgtccattct
agaaagaagtatttgaaaccatccaacaatgttctattctctgttggctcgaccatctaccacgagaagagggacttactga
ggagctggcacctgccgtctgtatttcacttacgtggcaagcaaaattacacatgtcggtgtgagactatagttagttgcgac
gggtacgtcgttaaaagaatagctatcagtccaggcctgtatgggaagccttcaggctatgctgctacgatgcaccgcgag
ggattcttgtgctgcaaagtgacagacacattgaacggggagagggtctcttttcccgtgtgcacgtatgtgccagctacatt
gtgtgaccaaatgactggcatactggcaacagatgtcagtgcggacgacgcgcaaaaactgctggttgggctcaaccag
cgtatagtcgtcaacggtcgcacccagagaaacaccaataccatgaaaaattaccttttgcccgtagtggcccaggcattt
gctaggtgggcaaaggaatataaggaagatcaagaagatgaaaggccactaggactacgagatagacagttagtcatg
gggtgttgttgggcttttagaaggcacaagataacatctatttataagcgcccggatacccaaaccatcatcaaagtgaaca
gcgatttccactcattcgtgctgcccaggataggcagtaacacattggagatcgggctgagaacaagaatcaggaaaatg
ttagaggagcacaaggagccgtcacctctcattaccgccgaggacgtacaagaagctaagtgcgcagccgatgaggct
aaggaggtgcgtgaagccgaggagttgcgcgcagctctaccacctttggcagctgatgttgaggagcccactctggaagc
cgatgtcgacttgatgttacaagaggctggggccggctcagtggagacacctcgtggcttgataaaggttaccagctacga
tggcgaggacaagatcggctcttacgctgtgctttctccgcaggctgtactcaagagtgaaaaattatcttgcatccaccctct
cgctgaacaagtcatagtgataacacactctggccgaaaagggcgttatgccgtggaaccataccatggtaaagtagtgg

Fig. 8E tgccagagggacatgcaatacccgtccaggactttcaagctctgagtgaaagtgccaccattgtgtacaacgaacgtgagt
tcgtaaacaggtacctgcaccatattgccacacatggaggagcgctgaacactgatgaagaatattacaaaactgtcaag
cccagcgagcacgacggcgaatacctgtacgacatcgacaggaaacagtgcgtcaagaaagaactagtcactgggct
agggctcacaggcgagctggtggatcctcccttccatgaattcgcctacgagagtctgagaacacgaccagccgctcctta
ccaagtaccaaccataggggtgtatggcgtgccaggatcaggcaagtctggcatcattaaaagcgcagtcaccaaaaaa
gatctagtggtgagcgccaagaaagaaactgtgcagaaattataagggacgtcaagaaaatgaaagggctggacgtc
aatgccagaactgtggactcagtgctcttgaatggatgcaaacaccccgtagagaccctgtatattgacgaagcttttgcttgt
catgcaggtactctcagagcgctcatagccattataagacctaaaaaggcagtgctctgcggggatcccaaacagtgcgg
ttttttttaacatgatgtgcctgaaagtgcattttaaccacgagatttgcacacaagtcttccacaaaagcatctctcgccgttgca
ctaaatctgtgacttcggtcgtctcaaccttgttttacgacaaaaaaatgagaacgacgaatccgaaagagactaagattgt
gattgacactaccggcagtaccaaacctaagcaggacgatctcattctcacttgtttcagagggtgggtgaagcagttgcaa
atagattacaaaggcaacgaaataatgacggcagctgcctctcaagggctgacccgtaaaggtgtgtatgccgttcggta
caaggtgaatgaaaatcctctgtacgcacccacctcagaacatgtgaacgtcctactgacccgcacggaggaccgcatc
gtgtggaaaacactagccggcgacccatggataaaaacactgactgccaagtaccctgggaatttcactgccacgatag
aggagtggcaagcagagcatgatgccatcatgaggcacatcttggagagaccggaccctaccgacgtcttccagaataa
ggcaaacgtgtgttgggccaaggctttagtgccggtgctgaagaccgctggcatagacatgaccactgaacaatggaac
actgtggatttttttgaaacggacaaagctcactcagcagagatagtattgaaccaactatgcgtgaggttctttggactcgat
ctggactccggtctattttctgcacccactgttccgttatccattaggaataatcactgggataactccccgtcgcctaacatgta
cgggctgaataaagaagtggtccgtcagctctctcgcaggtacccacaactgcctcgggcagttgccactggaagagtct
atgacatgaacactggtacactgcgcaattatgatccgcgcataaacctagtacctgtaaacagaagactgcctcatgcttt
agtcctccaccataatgaacacccacagagtgacttttcttcattcgtcagcaaattgaagggcagaactgtcctggtggtcg
gggaaaagttgtccgtcccaggcaaaatggttgactggttgtcagaccggcctgaggctaccttcagagctcggctggattt
aggcatcccaggtgatgtgcccaaatatgacataatatttgttaatgtgaggaccccatataaataccatcactatcagcagt
gtgaagaccatgccattaagcttagcatgttgaccaagaaagcttgtctgcatctgaatcccggcggaacctgtgtcagcat
aggttatggttacgctgacagggccagcgaaagcatcattggtgctatagcgcggcagttcaagttttcccgggtatgcaaa
ccgaaatcctcacttgaagagacggaagttctgtttgtattcattgggtacgatcgcaaggcccgtacgcacaatccttacaa
gctttcatcaaccttgaccaacatttatacaggttccagactccacgaagccggatgtgcaccctcatatcatgtggtgcgag
gggatattgccacggccaccgaaggagtgattataaatgctgctaacagcaaaggacaacctggcggaggggt
gtgcggagcgctgtataagaaattcccggaaagcttcgatttacagccgatcgaagtaggaaaagcgcgactggtcaaa
ggtgcagctaaacatatcattcatgccgtaggaccaaaacttcaacaaagtttcggaggttgaaggtgacaaacagttggca
gaggcttatgagtccatcgctaagattgtcaacgataacaattacaagtcagtagcgattccactgttgtccaccggcatctttt
ccgggaacaaagatcgactaacccaatcattgaaccatttgctgacagctttagacaccactgatgcagatgtagccatat
actgcagggacaagaaatgggaaatgactctcaaggaagcagtggctaggagagaagcagtggaggagatatgcata
tccgacgactcttcagtgacagaacctgatgcagagctggtgagggtgcatccgaagagttctttggctggaaggaaggg
ctacagcacaagcgatggcaaaactttctcatatttggaagggaccaagtttcaccaggcggccaaggatatagcagaa
attaatgccatgtggcccgttgcaacggaggccaatgagcaggtatgcatgtatatcctcggagaaagcatgagcagtatt
aggtcgaaatgccccgtcgaagagtcggaagcctccacaccacctagcacgctgccttgcttgtgcatccatgccatgact
ccagaaagagtacagcgcctaaaagcctcacgtccagaacaaattactgtgtgctcatcctttccattgccgaagtataga
atcactggtgtgcagaagatccaatgctcccagcctatattgttctcaccgaaagtgcctgcgtatattcatccaaggaagtat
ctcgtggaaacaccaccggtagacgagactccggagccatcggcagagaaccaatccacagaggggacacctgaac
aaccaccacttataaccgaggatgagaccaggactagaacgcctgagccgatcatcatcgaagaggaagaagaggat
agcataagtttgctgtcagatggcccgacccaccaggtgctgcaagtcgaggcagacattcacgggccgccctctgtatct
agctcatcctggtccattcctcatgcatccgactttgatgtggacagtttatccatacttgacaccctggagggagctagcgtg
accagcggggcaacgtcagccgagactaactcttacttcgcaaagagtatggagtttctggcgcgaccggtgcctgcgcct
cgaacagtattcaggaaccctccacatcccgctccgcgcacaagaacaccgtcacttgcacccagcagggcctgctcga
gaaccagcctagtttccaccccgccaggcgtgaatagggtgatcactagagaggagctcgaggcgcttaccccgtcacg
cactcctagcaggtcggtctcgagaaccagcctggtctccaacccgccaggcgtaaataggtgattacaagagaggag
tttgaggcgttcgtagcacaacaacaatgacggtttgatgcgggtgcatacatcttttcctccgacaccggtcaagggcattta
caacaaaaatcagtaaggcaaacggtgctatccgaagtggtgttggagaggaccgaattggagatttcgtatgccccgcg
cctcgaccaagaaaaagaagaattactacgcaagaaattacagttaaatcccacacctgctaacagaagcagatacca
gtccaggaaggtggagaacatgaaagccataacagctagacgtattctgcaaggcctagggcattatttgaaggcagaa

Fig. 8F

```
ggaaaagtggagtgctaccgaaccctgcatcctgttcctttgtattcatctagtgtgaaccgtgccttttcaagccccaaggtc
gcagtggaagcctgtaacgccatgttgaaagagaactttccgactgtggcttcttactgtattattccagagtacgatgcctat
tggacatggttgacggagcttcatgctgcttagacactgccagttttttgccctgcaaagctgcgcagctttccaaagaaacac
tcctatttggaacccacaatacgatcggcagtgccttcagcgatccagaacacgctccagaacgtcctggcagctgccac
aaaaagaaattgcaatgtcacgcaaatgagagaattgcccgtattggattcggcggcctttaatgtggaatgcttcaagaa
atatgcgtgtaataatgaatattgggaaacgtttaaagaaaaaccccatcaggcttactgaagaaaacgtggtaaattacatt
accaaattaaaaggaccaaaagctgctgctcttttgcgaagacacataatttgaatatgttgcaggacataccaatggaca
ggtttgtaatggacttaaagagagacgtgaaagtgactccaggaacaaaacatactgaagaacggcccaaggtacagg
tgatccaggctgccgatccgctagcaacagcgtatctgtgcggaatccaccgagagctggttaggagattaaatgcggtcc
tgcttccgaacattcatacactgtttgatatgtcggctgaagactttgacgctattatagccgagcacttccagcctggggattgt
gttctggaaactgacatcgcgtcgtttgataaaagtgaggacgacgccatggctctgaccgcgttaatgattctggaagactt
aggtgtggacgcagagctgttgacgctgattgaggcggctttcggcgaaatttcatcaatacatttgcccactaaaactaaat
ttaaattcggagccatgatgaaatctggaatgttcctcacactgtttgtgaacacagtcattaacattgtaatcgcaagcagag
tgttgagagaacggctaaccggatcaccatgtgcagcattcattggagatgacaatatcgtgaaaggagtcaaatcggac
aaattaatggcagacaggtgcgccacctggttgaatatggaagtcaagattatagatgctgtggtgggcgagaaagcgcc
ttatttctgtggagggtttatttttgtgtgactccgtgaccggcacagcgtgccgtgtggcagaccccctaaaaaggctgtttaag
cttggcaaacctctggcagcagacgatgaacatgatgatgacaggagaagggcattgcatgaagagtcaacacgctgg
aaccgagtgggtattctttcagagctgtgcaaggcagtagaatcaaggtatgaaaccgtaggaacttccatcatagttatgg
ccatgactactctagctagcagtgttaaatcattcagctacctgagaggggcccctataactctctacggctaacctgaatgg
actacgacatagtctagtccgccaagtctagaccatgtctggtcgtaaagctcagggaaaaaccctgggcgtcaatatggt
acgacgaggagttcgctccttgtcaaacaaaataaaacaaaaaacaaaacaaattggaaacagacctggaccttcaag
aggtgttcaaggatttatcttttcttttttgttcaacattttgactggaaaaaagatcacagcccacctaaagaggttgtggaaaa
tgctggacccaagacaaggcttggctgttctaaggaaagtcaagagagtggtggccagtttgatgagaggattgtcctcaa
ggaaacgccgttcccatgatgttctgactgtgcaattcctaattttgggaatgctgttgatgacgggtggataagggcccctat
aactctctacggctaacctgaatggactacgacatagtctagtccgccaagtctagagcttaccatgaccgagtacaagcc
cacggtgcgcctcgccacccgcgacgacgtccccagggccgtacgcaccctcgccgccgcgttcgccgactacccgc
cacgcgccacaccgtcgatccggaccgccacatcgagcgggtcaccgagctgcaagaactcttcctcacgcgcgtcgg
gctcgacatcggcaaggtgtgggtcgcggacgacggcgccgcggtggcggtctggaccacgccggagagcgtcgaag
cgggggcggtgttcgccgagatcggcccgcgcatggccgagttgagcggttcccggctggccgcgcagcaacagatgg
aaggcctcctggcgccgcaccggccccaaggagcccgcgtggttcctggccaccgtcggcgtctcgcccgaccaccagg
gcaagggtctgggcagcgccgtcgtgctccccggagtggaggcggccgagcgcgccggggtgcccgccttcctggaga
cctccgcgccccgcaacctcccccttctacgagcggctcggcttcaccgtcaccgccgacgtcgagtgcccgaaggaccg
cgcgacctggtgcatgacccgcaagcccggtgcctgacgcccgcccacgacccgcagcgcccgaccgaaaggagc
gcacgaccccatgatcgctagaccatggggtaccgagtatgttacgtgcaaaggtgattgtcaccccccgaaagaccata
ttgtgacacaccctcagtatcacgcccaaacatttacagccgcggtgtcaaaaaccgcgtggacgtggttaacatccctgct
gggaggatcagccgtaattattataattggcttggtgctggctactattgtggccatgtacgtgctgaccaaccagaaacata
attgaatacagcagcaattggcaagctgcttacatagaactcgcggcgattggcatgccgccttaaaattttattttatttttcct
ttcttttccgaatcggattttgttttaatatttcaaaaaaaaaaaaaaaaaaaaaacgcgtcgaggggaattaattcttga
agacgaaagggccaggtggcacttttcggggaaatgtgcgcggaacccctatttgtttattttctaaatacattcaaatatgta
tccgctcatgagacaataaccctgataaatgcttcaataatattgaaaaggaagagtatgagtattcaacatttccgtgtcg
cccttattccctttttgcggcattttgccttcctgtttttgctcacccagaaacgctggtgaaagtaaaagatgctgaagatcagtt
gggtgcacgagtgggttacatcgaactggatctcaacagcggtaagatccttgagagttttcgccccgaagaacgttttcca
atgatgagcacttttaaagttctgctatgtggcgcggtattatcccgtgttgacgccgggcaagagcaactcggtcgccgcat
acactattctcagaatgacttggttgagtactcaccagtcacagaaaagcatcttacggatggcatgacagtaagagaatta
tgcagtgctgccataaccatgagtgataacactgcggccaacttacttctgacaacgatcggaggaccgaaggagctaac
cgcttttttgcacaacatgggggatcatgtaactcgccttgatcgttgggaaccggagctgaatgaagccataccaaacgac
gagcgtgacaccacgatgcctgtagcaatggcaacaacgttgcgcaaactattaactggcgaactacttactctagcttccc
ggcaacaattaatagactggatggaggcggataaagttgcaggaccacttctgcgctcggcccttccggctggctggtttatt
gctgataaatctggagccggtgagcgtgggtctcgcggtatcattgcagcactggggccagatggtaagccctcccgtatc
gtagttatctacacgacggggagtcaggcaactatggatgaacgaaatagacagatcgctgagataggtgcctcactgatt
aagcattggtaactgtcagaccaagtttactcatatatactttagattgatttaaaacttcatttttaatttaaaaggatctaggtga
```

Fig. 8G agatccttttgataatctcatgaccaaaatcccttaacgtgagttttcgttccactgagcgtcagaccccgtagaaaagatca
aaggatcttcttgagatcctttttttctgcgcgtaatctgctgcttgcaaacaaaaaaaccaccgctaccagcggtggtttgtttg
ccggatcaagagctaccaactctttttccgaaggtaactggcttcagcagagcgcagataccaaatactgtccttctagtgta
gccgtagttaggccaccacttcaagaactctgtagcaccgcctacatacctcgctctgctaatcctgttaccagtggctgctgc
cagtggcgataagtcgtgtcttaccgggttggactcaagacgatagttaccggataaggcgcagcggtcgggctgaacgg
ggggttcgtgcacacagcccagcttggagcgaacgacctacaccgaactgagatacctacagcgtgagcattgagaaa
gcgccacgcttcccgaagggagaaaggcggacaggtatccggtaagcggcagggtcggaacaggagagcgcacga
gggagcttccaggggggaaacgcctggtatctttatagtcctgtcgggtttcgccacctctgacttgagcgtcgattttgtgatgc
tcgtcaggggggcggagcctatggaaaaacgccagcaacgcgagctcgatttaggtgacactata
(SEQ ID NO: 7)

Fig. 8H gatgggcggcgcatgagagaagcccagaccaattacctacccaaaatggagaaagttcacgttgacatcgaggaaga
cagcccattcctcagagctttgcagcggagcttcccgcagtttgaggtagaagccaagcaggtcactgataatgaccatgc
taatgccagagcgttttcgcatctggcttcaaaactgatcgaaacggaggtggacccatccgacacgatccttgacattgga
agtgcgcccgcccgcagaatgtattctaagcacaagtatcattgtatctgtccgatgagatgtgcggaagatccggacagat
tgtataagtatgcaactaagctgaagaaaaactgtaaggaaataactgataaggaattggacaagaaaatgaaggagct
ggccgccgtcatgagcgaccċtgacctggaaactgagactatgtgcctccacgacgacgagtcgtgtcgctacgaaggg
caagtcgctgtttaccaggatgtatacgcggttgacggaccgacaagtctctatcaccaagccaataagggagttagagtc
gcctactggataggctttgacaccaccccttttatgtttaagaacttggctggagcatatccatcatactctaccaactgggccg
acgaaaccgtgttaacggctcgtaacataggcctagcagctctgacgttatggagcggtcacgtagagggatgccattctt
agaaagaagtatttgaaaccatccaacaatgttctattctctgttggctcgaccatctaccacgagaagagggacttactga
ggagctggcacctgccgtctgtatttcacttacgtggcaagcaaaattacacatgtcggtgtgagactatagttagttgcgac
gggtacgtcgttaaaagaatagctatcagtccaggcctgtatgggaagccttcaggctatgctgctacgatgcaccgcgag
ggattcttgtgctgcaaagtgacagacacattgaacggggagagggtctcttttcccgtgtgcacgtatgtgccagctacatt
gtgtgaccaaatgactggcatactggcaacagatgtcagtgcggacgacgcgcaaaaactgctggttgggctcaaccag
cgtatagtcgtcaacggtcgcacccagagaaacaccaataccatgaaaaattaccttttgcccgtagtggcccaggcattt
gctaggtgggcaaaggaatataaggaagatcaagaagatgaaaggccactaggactacgagatagacagttagtcatg
gggtgttgttgggcttttagaaggcacaagataacatctatttataagcgcccggatacccaaaccatcatcaaagtgaaca
gcgatttccactcattcgtgctgcccaggataggcagtaacacattggagatcgggctgagaacaagaatcaggaaaatg
ttagaggagcacaaggagccgtcacctctcattaccgccgaggacgtacaagaagctaagtgcgcagccgatgaggct
aaggaggtgcgtgaagccgaggagttgcgcgcagctctaccacctttggcagctgatgttgaggagcccactctggaagc
cgatgtcgacttgatgttacaagaggctggggccggctcagtggagacacctcgtggcttgataaaggttaccagctacga
tggcgaggacaagatcggctcttacgctgtgctttctccgcaggctgtactcaagagtgaaaaattatcttgcatccaccctct
cgctgaacaagtcatagtgataacacactctggccgaaaagggcgttatgccgtggaaccataccatggtaaagtagtgg
tgccagagggacatgcaatacccgtccaggactttcaagctctgagtgaaagtgccaccattgtgtacaacgaacgtgagt
tcgtaaacaggtacctgcaccatattgccacacatggaggagcgctgaacactgatgaagaatattacaaaactgtcaag
cccagcgagcacgacggcgaatacctgtacgacatcgacaggaaacagtgcgtcaagaaagaactagtcactgggct
agggctcacaggcgagctggtggatcctcccttccatgaattcgcctacgagagtctgagaacacgaccagccgctcctta
ccaagtaccaaccataggggtgtatggcgtgccaggatcaggcaagtctggcatcattaaaagcgcagtcaccaaaaaa
gatctagtggtgagcgccaagaaagaaaactgtgcagaaattataagggacgtcaagaaaatgaaagggctggacgtc
aatgccagaactgtggactcagtgctcttgaatggatgcaaacaccccgtagagaccctgtatattgacgaagcttttgcttgt
catgcaggtactctcagagcgctcatagccattataagacctaaaaaggcagtgctctgcggggatcccaaacagtgcgg
tttttttaacatgatgtgcctgaaagtgcattttaaccacgagatttgcacacaagtcttccacaaaagcatctctcgccgttgca
ctaaatctgtgacttcggtcgtctcaaccttgttttacgacaaaaaatgagaacgacgaatccgaaagagactaagattgt
gattgacactaccggcagtaccaaacctaagcaggacgatctcattctcacttgtttcagagggtgggtgaagcagttgcaa
atagattacaaaggcaacgaaataatgacggcagctgcctctcaagggctgacccgtaaaggtgtgtatgccgttcggta
caaggtgaatgaaaatcctctgtacgcacccacctcagaacatgtgaacgtcctactgacccgcacggaggaccgcatc
gtgtggaaaacactagccggcgacccatggataaaaacactgactgccaagtaccctgggaatttcactgccacgatag
aggagtggcaagcagagcatgatgccatcatgaggcacatcttggagagaccggaccctaccgacgtcttccagaataa

Fig. 8I

```
ggcaaacgtgtgttgggccaaggctttagtgccggtgctgaagaccgctggcatagacatgaccactgaacaatggaac
actgtggattattttgaaacggacaaagctcactcagcagagatagtattgaaccaactatgcgtgaggttctttggactcgat
ctggactccggtctattttctgcacccactgttccgttatccattaggaataatcactgggataactccccgtcgcctaacatgta
cgggctgaataaagaagtggtccgtcagctctctcgcaggtacccacaactgcctcgggcagttgccactggaagagtct
atgacatgaacactggtacactgcgcaattatgatccgcgcataaacctagtacctgtaaacagaagactgcctcatgcttt
agtcctccaccataatgaacacccacagagtgacttttcttcattcgtcagcaaattgaagggcagaactgtcctggtggtcg
gggaaaagttgtccgtcccaggcaaaatggttgactggttgtcagaccggcctgaggctaccttcagagctcggctggattt
aggcatcccaggtgatgtgcccaaatatgacataatatttgttaatgtgaggaccccatataaataccatcactatcagcagt
gtgaagaccatgccattaagcttagcatgttgaccaagaaagcttgtctgcatctgaatcccggcggaacctgtgtcagcat
aggttatggttacgctgacagggccagcgaaagcatcattggtgctatagcgcggcagttcaagttttcccgggtatgcaaa
ccgaaatcctcacttgaagagacggaagttctgtttgtattcattgggtacgatcgcaaggcccgtacgcacaatccttacaa
gctttcatcaaccttgaccaacatttatacaggttccagactccacgaagccggatgtgcaccctcatatcatgtggtgcgag
gggatattgccacggccaccgaaggagtgattataaatgctgctaacagcaaaggacaacctggcggaggggtgtgcg
gagcgctgtataagaaattcccggaaagcttcgatttacagccgatcgaagtaggaaaagcgcgactggtcaaaggtgc
agctaaacatatcattcatgccgtaggaccaaacttcaacaaagtttcggaggttgaaggtgacaaacagttggcagagg
cttatgagtccatcgctaagattgtcaacgataacaattacaagtcagtagcgattccactgttgtccaccggcatcttttccgg
gaacaaagatcgactaacccaatcattgaaccatttgctgacagctttagacaccactgatgcagatgtagccatatactgc
agggacaagaaatgggaaatgactctcaaggaagcagtggctaggagagaagcagtggaggagatatgcatatccga
cgactcttcagtgacagaacctgatgcagagctggtgagggtgcatccgaagagttctttggctggaaggaagggctaca
gcacaagcgatggcaaaactttctcatatttggaagggaccaagtttcaccaggcggccaaggatatagcagaaattaat
gccatgtggcccgttgcaacggaggccaatgagcaggtatgcatgtatatcctcggagaaagcatgagcagtattaggtc
gaaatgccccgtcgaagagtcggaagcctccacaccacctagcacgctgccttgcttgtgcatccatgccatgactccaga
aagagtacagcgcctaaaagcctcacgtccagaacaaaattactgtgtgctcatcctttccattgccgaagtatagaatcact
ggtgtgcagaagatccaatgctcccagcctatattgttctcaccgaaagtgcctgcgtatattcatccaaggaagtatctcgtg
gaaacaccaccggtagacgagactccggagccatcggcagagaaccaatccacagaggggacacctgaacaacca
ccacttataaccgaggatgagaccaggactagaacgcctgagccgatcatcatcgaagaggaagaagaggatagcat
aagtttgctgtcagatggcccgacccaccaggtgctgcaagtcgaggcagacattcacgggccgccctctgtatctagctc
atcctggtccattcctcatgcatccgactttgatgtggacagtttatccatacttgacaccctggagggagctagcgtgaccag
cggggcaacgtcagccgagactaactcttacttcgcaaagagtatggagtttctggcgcgaccggtgcctgcgcctcgaac
agtattcaggaaccctccacatcccgctccgcgcacaagaacaccgtcacttgcacccagcagggcctgctcgagaacc
agcctagtttccaccccgccaggcgtgaatagggtgatcactagagaggagctcgaggcgcttacccccgtcacgcactcc
tagcaggtcggtctcgagaaccagcctggtctccaacccgccaggcgtaaatagggtgattacaagagaggagtttgag
gcgttcgtagcacaacaacaatgacggtttgatgcgggtgcatacatcttttcctccgacaccggtcaagggcatttacaac
aaaaatcagtaaggcaaacggtgctatccgaagtggtgttggagaggaccgaattggagatttcgtatgccccgcgcctc
gaccaagaaaaagaagaattactacgcaagaaattacagttaaatcccacacctgctaacagaagcagataccagtcc
aggaaggtggagaacatgaaagccataacagctagacgtattctgcaaggcctagggcattatttgaaggcagaagga
aaagtggagtgctaccgaaccctgcatcctgttcctttgtattcatctagtgtgaaccgtgccttttcaagccccaaggtcgcag
tggaagcctgtaacgccatgttgaaagagaacttccgactgtggcttcttactgtattattccagagtacgatgcctatttgga
catggttgacggagcttcatgctgcttagacactgccagttttgccctgcaaagctgcgcagctttccaaagaaacactccta
tttggaacccacaatacgatcggcagtgccttcagcgatccagaacacgctccagaacgtcctggcagctgccacaaaa
agaaattgcaatgtcacgcaaatgagagaattgcccgtattggattcggcggcctttaatgtggaatgcttcaagaaatatgc
gtgtaataatgaatattgggaaacgtttaaagaaaaccccatcaggcttactgaagaaaacgtggtaaattacattaccaa
attaaaaggaccaaaagctgctgctcttttgcgaagacacataatttgaatatgttcaggacataccaatggacaggtttgt
aatggacttaaagagagacgtgaaagtgactccaggaacaaaacatactgaagaacggcccaaggtacaggtgatcc
aggctgccgatccgctagcaacagcgtatctgtgcggaatccaccgagagctggttaggagattaaatgcggtcctgcttc
cgaacattcatacactgtttgatatgtcggctgaagactttgacgctattatagccgagcacttccagcctggggattgtgttctg
gaaactgacatcgcgtcgtttgataaaagtgaggacgacgccatggctctgaccgcgttaatgattctggaagacttaggtg
tggacgcagagctgttgacgctgattgaggcggcttcggcgaaatttcatcaatacatttgcccactaaaactaaatttaaat
tcggagccatgatgaaatctggaatgttcctcacactgtttgtgaacacagtcattaacattgtaatcgcaagcagagtgttga
gagaacggctaaccggatcaccatgtgcagcattcattggagatgacaatatcgtgaaggagtcaaatcggacaaatta
atggcagacaggtgcgccacctggttgaatatggaagtcaagattatagatgctgtggtgggcgagaaagcgccttatttct
```

Fig. 8J gtggagggtttattttgtgtgactccgtgaccggcacagcgtgccgtgtggcagaccccctaaaaaggctgtttaagcttggc
aaacctctggcagcagacgatgaacatgatgatgacaggagaagggcattgcatgaagagtcaacacgctggaaccg
agtgggtattctttcagagctgtgcaaggcagtagaatcaaggtatgaaaccgtaggaacttccatcatagttatggccatga
ctactctagctagcagtgttaaatcattcagctacctgagaggggccccctataactctctacggctaacctgaatggactacg
acatagtctagtccgccaagtctagaccatgtctggtcgtaaagctcagggaaaaaccctgggcgtcaatatggtacgacg
aggagttcgctccttgtcaaacaaaataaaacaaaaaacaaaacaaattggaaacagacctggaccttcaagaggtgtt
caaggatttatcttttcttttgttcaacattttgactggaaaaaagatcacagcccacctaaagaggttgtggaaaatgctgga
cccaagacaaggcttggctgttctaaggaaagtcaagagagtggtggccagtttgatgagaggattgtcctcaaggaaac
gccgttcccatgatgttctgactgtgcaattcctaattttgggaatgctgttgatgacgggtggagtgaccttggtgcggaaaaa
cagatggttgctcctaaatgtgacatctgaggacctcgggtaagggcccctataactctctacggctaacctgaatggacta
cgacatagtctagtccgccaagtctagagcttaccatgaccgagtacaagcccacggtgcgcctcgccacccgcgacga
cgtccccagggccgtacgcaccctcgccgccgcgttcgccgactaccccgccacgcgccacaccgtcgatccggaccg
ccacatcgagcgggtcaccgagctgcaagaactcttcctcacgcgcgtcgggctcgacatcggcaaggtgtgggtcgcg
gacgacggcgccgcggtggcggtctggaccacgccggagagcgtcgaagcgggggcggtgttcgccgagatcggccc
gcgcatggccgagttgagcggttcccggctggccgcgcagcaacagatggaaggcctcctggcgccgcaccggccca
aggagcccgcgtggttcctggccaccgtcggcgtctcgcccgaccaccagggcaagggtctgggcagcgccgtcgtgct
ccccggagtggaggcggccgagcgcgccggggtgcccgccttcctggagacctccgcgccccgcaacctcccttctac
gagcggctcggcttcaccgtcaccgccgacgtcgagtgccccgaaggaccgcgcgacctggtgcatgacccgcaagccc
ggtgcctgacgcccgccccacgacccgcagcgcccgaccgaaaggagcgcacgacccccatgatcgctagaccatgg
ggtaccgagtatgttacgtgcaaggtgattgtcaccccccgaaagaccatattgtgacacaccctcagtatcacgcccaa
acatttacagccgcggtgtcaaaaaccgcgtggacgtggttaacatccctgctgggaggatcagccgtaattattataattg
gcttggtgctggctactattgtggccatgtacgtgctgaccaaccagaaacataattgaatacagcagcaattggcaagctg
cttacatagaactcgcggcgattggcatgccgccttaaaattttatttttattttttctttctttttccgaatcggattttgttttaatatttc
aaaaaaaaaaaaaaaaaaaaaaaaacgcgtcgaggggaattaattcttgaagacgaaagggccaggtggcacttttc
ggggaaatgtgcgcggaaccccctatttgtttatttttctaaatacattcaaatatgtatccgctcatgagacaataaccctgata
aatgcttcaataatattgaaaaggaagagtatgagtattcaacatttccgtgtcgcccttattccctttttgcggcattttgcctt
cctgtttttgctcacccagaaacgctggtgaaagtaaaagatgctgaagatcagttgggtgcacgagtgggttacatcgaac
tggatctcaacagcggtaagatccttgagagttttcgccccgaagaacgttttccaatgatgagcacttttaaagttctgctatg
tggcgcggtattatcccgtgttgacgccgggcaagagcaactcggtcgccgcatacactattctcagaatgacttggttgagt
actcaccagtcacagaaaagcatcttacggatggcatgacagtaagagaattatgcagtgctgccataaccatgagtgat
aacactgcggccaacttacttctgacaacgatcggaggaccgaaggagctaaccgcttttttgcacaacatgggggatcat
gtaactcgccttgatcgttgggaaccggagctgaatgaagccataccaaacgacgagcgtgacaccacgatgcctgtag
caatggcaacaacgttgcgcaaactattaactggcgaactacttactctagcttcccggcaacaattaatagactggatgga
ggcggataaagttgcaggaccacttctgcgctcggcccttccggctggctggtttattgctgataaatctggagccggtgagc
gtgggtctcgcggtatcattgcagcactggggccagatggtaagccctcccgtatcgtagttatctacacgacggggagtca
ggcaactatggatgaacgaaatagacagatcgctgagataggtgcctcactgattaagcattggtaactgtcagaccaagt
ttactcatatatactttagattgatttaaaacttcattttaatttaaaaggatctaggtgaagatccttttgataatctcatgaccaa
aatcccttaacgtgagttttcgttccactgagcgtcagaccccgtagaaaagatcaaaggatcttcttgagatccttttttctgc
gcgtaatctgctgcttgcaaacaaaaaaaccaccgctaccagcggtggtttgtttgccggatcaagagctaccaactctttt
ccgaaggtaactggcttcagcagagcgcagataccaaatactgtccttctagtgtagccgtagttaggccaccacttcaag
aactctgtagcaccgcctacatacctcgctctgctaatcctgttaccagtggctgctgccagtggcgataagtcgtgtcttacc
gggttggactcaagacgatagttaccggataaggcgcagcggtcgggctgaacggggggttcgtgcacacagcccagct
tggagcgaacgacctacaccgaactgagatacctacagcgtgagcattgagaaagcgccacgcttcccgaagggaga
aaggcggacaggtatccggtaagcggcagggtcggaacaggagagcgcacgagggagcttccaggggaaacgcc
tggtatctttatagtcctgtcgggtttcgccacctctgacttgagcgtcgatttttgtgatgctcgtcaggggggcggagcctatgg
aaaaacgccagcaacgcgagctcgatttaggtgacactata (SEQ ID NO: 8)

```
gatgggcggcgcatgagagaagcccagaccaattacctacccaaaatggagaaagttcacgttgacatcgaggaaga
cagcccattcctcagagctttgcagcggagcttcccgcagtttgaggtagaagccaagcaggtcactgataatgaccatgc
taatgccagagcgttttcgcatctggcttcaaaactgatcgaaacggaggtggacccatccgacacgatccttgacattgga
agtgcgcccgcccgcagaatgtattctaagcacaagtatcattgtatctgtccgatgagatgtgcggaagatccggacagat
tgtataagtatgcaactaagctgaagaaaaactgtaaggaaataactgataaggaattggacaagaaaatgaaggagct
ggccgccgtcatgagcgaccctgacctggaaactgagactatgtgcctccacgacgacgagtcgtgtcgctacgaaggg
caagtcgctgtttaccaggatgtatacgcggttgacggaccgacaagtctctatcaccaagccaataagggagttagagtc
gcctactggataggctttgacaccaccccttttatgtttaagaacttggctggagcatatccatcatactctaccaactgggccg
acgaaaccgtgttaacggctcgtaacataggcctatgcagctctgacgttatggagcggtcacgtagagggatgtccattctt
agaaagaagtatttgaaacccatccaacaatgttctattctctgttggctcgaccatctaccacgagaagagggacttactga
ggagctggcacctgccgtctgtatttcacttacgtggcaagcaaaattacacatgtcggtgtgagactatagttagttgcgac
gggtacgtcgttaaaagaatagctatcagtccaggcctgtatgggaagccttcaggctatgctgctacgatgcaccgcgag
ggattcttgtgctgcaaagtgacagacacattgaacggggagagggtctcttttcccgtgtgcacgtatgtgccagctacatt
gtgtgaccaaatgactggcatactggcaacagatgtcagtgcggacgacgcgcaaaaactgctggttgggctcaaccag
cgtatagtcgtcaacggtcgcacccagagaaacaccaataccatgaaaaattaccttttgcccgtagtggcccaggcattt
gctaggtgggcaaaggaatataaggaagatcaagaagatgaaaggccactaggactacgagatagacagttagtcatg
gggtgttgttgggcttttagaaggcacaagataacatctatttataagcgcccggatacccaaaccatcatcaaagtgaaca
gcgatttccactcattcgtgctgcccaggataggcagtaacacattggagatcgggctgagaacaagaatcaggaaaatg
ttagaggagcacaaggagccgtcacctctcattaccgccgaggacgtacaagaagctaagtgcgcagccgatgaggct
aaggaggtgcgtgaagccgaggagttgcgcgcagctctaccacctttggcagctgatgttgaggagcccactctggaagc
cgatgtcgacttgatgttacaagaggctggggccggctcagtggagacacctcgtggcttgataaaggttaccagctacga
tggcgaggacaagatcggctcttacgctgtgctttctccgcaggctgtactaagagtgaaaaattatcttgcatccaccctct
cgctgaacaagtcatagtgataacacactctggccgaaaagggcgttatgccgtggaaccataccatggtaaagtagtgg
tgccagagggacatgcaatacccgtccaggactttcaagctctgagtgaaagtgccaccattgtgtacaacgaacgtgagt
tcgtaaacaggtacctgcaccatattgccacacatggaggagcgctgaacactgatgaagaatattacaaaactgtcaag
cccagcgagcacgacggcgaatacctgtacgacatcgacaggaaacagtgcgtcaagaaagaactagtcactgggct
agggctcacaggcgagctggtggatcctcccttccatgaattcgcctacgagagtctgagaacacgaccagccgctcctta
ccaagtaccaaccataggggtgtatggcgtgccaggatcaggcaagtctggcatcattaaaagcgcagtcaccaaaaaa
gatctagtggtgagcgccaagaaagaaactgtgcagaaattataagggacgtcaagaaatgaaagggctggacgtc
aatgccagaactgtggactcagtgctcttgaatggatgcaaacaccccgtagagaccctgtatattgacgaagcttttgcttgt
catgcaggtactctcagagcgctcatagccattataagacctaaaaaggcagtgctctgcggggatcccaaacagtgcgg
tttttttaacatgatgtgcctgaaagtgcattttaaccacgagatttgcacacaagtcttccacaaaagcatctctcgccgttgca
ctaaatctgtgacttcggtcgtctcaaccttgttttacgacaaaaaatgagaacgacgaatccgaaagagactaagattgt
gattgacactaccggcagtaccaaacctaagcaggacgatctcattctcacttgtttcagagggtgggtgaagcagttgcaa
atagattacaaaggcaacgaaataatgacggcagctgcctctcaagggctgacccgtaaaggtgtgtatgccgttcggta
caaggtgaatgaaaatcctctgtacgcaccccacctcagaacatgtgaacgtcctactgacccgcacggaggaccgcatc
gtgtggaaaacactagccggcgacccatggataaaaacactgactgccaagtaccctgggaatttcactgccacgatag
aggagtggcaagcagagcatgatgccatcatgaggcacatcttggagagaccggaccctaccgacgtcttccagaataa
ggcaaacgtgtgttgggccaaggctttagtgccggtgctgaagaccgctggcatagacatgaccactgaacaatggaac
actgtggattattttgaaacggacaaagctcactcagcagagatagtattgaaccaactatgcgtgaggttctttggactcgat
ctggactccggtctattttctgcacccactgttccgttatccattaggaataatcactgggataactccccgtcgcctaacatgta
cgggctgaataaagaagtggtccgtcagctctctcgcaggtacccacaactgcctcgggcagttgccactggaagagtct
atgacatgaacactggtacactgcgcaattatgatccgcgcataaacctagtacctgtaaacagaagactgcctcatgcttt
agtcctccaccataatgaacacccacagagtgacttttcttcattcgtcagcaaattgaagggcagaactgtcctggtggtcg
gggaaaagttgtccgtcccaggcaaaatggttgactggttgtcagaccggcctgaggctaccttcagagctcggctggattt
aggcatcccaggtgatgtgcccaaatatgacataatatttgttaatgtgaggacccccatataaataccatcactatcagcagt
gtgaagaccatgccattaagcttagcatgttgaccaagaaagcttgtctgcatctgaatcccggcggaacctgtgtcagcat
aggttatggttacgctgacagggccagcgaaagcatcattggtgctatagcgcggcagttcaagttttcccgggtatgcaaa
ccgaaatcctcacttgaagagacggaagttctgtttgtattcattgggtacgatcgcaaggcccgtacgcacaatccttacaa
gctttcatcaaccttgaccaacatttatacaggttccagactccacgaagccggatgtgcaccctcatatcatgtggtgcgag
gggatattgccacggccaccgaaggagtgattataaatgctgctaacagcaaaggacaacctggcggaggggtgtgcg
```

Fig. 8L gagcgctgtataagaaattcccggaaagcttcgatttacagccgatcgaagtaggaaaagcgcgactggtcaaggtgc
agctaaacatatcattcatgccgtaggaccaaacttcaacaaagtttcggaggttgaaggtgacaaacagttggcagagg
cttatgagtccatcgctaagattgtcaacgataacaattacaagtcagtagcgattccactgttgtccaccggcatcttttccgg
gaacaaagatcgactaacccaatcattgaaccatttgctgacagctttagacaccactgatgcagatgtagccatatactgc
agggacaagaaatgggaaatgactctcaaggaagcagtggctaggagagaagcagtggaggagatatgcatatccga
cgactcttcagtgacagaacctgatgcagagctggtgaggtgcatccgaagagttctttggctggaaggaagggctaca
gcacaagcgatggcaaaactttctcatatttggaagggaccaagtttcaccaggcggccaaggatatagcagaaattaat
gccatgtggcccgttgcaacggaggccaatgagcaggtatgcatgtatatcctcggagaaagcatgagcagtattaggtc
gaaatgccccgtcgaagagtcggaagcctccacaccacctagcacgctgccttgcttgtgcatccatgccatgactccaga
aagagtacagcgcctaaaagcctcacgtccagaacaaattactgtgtgctcatcctttccattgccgaagtatagaatcact
ggtgtgcagaagatccaatgctcccagcctatattgttctcaccgaaagtgcctgcgtatattcatccaaggaagtatctcgtg
gaaacaccaccggtagacgagactccggagccatcggcagagaaccaatccacagaggggacacctgaacaacca
ccacttataaccgaggatgagaccaggactagaacgcctgagccgatcatcatcgaagaggaagaagaggatagcat
aagtttgctgtcagatggcccgacccaccaggtgctgcaagtcgaggcagacattcacgggccgccctctgtatctagctc
atcctggtccattcctcatgcatccgactttgatgtggacagttatccatacttgacaccctggagggagctagcgtgaccag
cggggcaacgtcagccgagactaactcttacttcgcaaagagtatggagtttctggcgcgaccggtgcctgcgcctcgaac
agtattcaggaaccctccacatcccgctccgcgcacaagaacaccgtcacttgcacccagcagggcctgctcgagaacc
agcctagtttccaccccgccaggcgtgaataggtgatcactagagaggagctcgaggcgcttaccccgtcacgcactcc
tagcaggtcggtctcgagaaccagcctggtctccaacccgccaggcgtaaataggtgattacaagagaggagtttgag
gcgttcgtagcacaacaacaatgacggtttgatgcgggtgcatacatctttttcctccgacaccggtcaagggcatttacaac
aaaaatcagtaaggcaaaccgtgctatccgaagtggtgttggagaggaccgaattggagatttcgtatgccccgcgcctc
gaccaagaaaaagaagaattactacgcaagaaattacagttaaatcccacacctgctaacagaagcagataccagtcc
aggaaggtggagaacatgaaagccataacagctagacgtattctgcaaggcctagggcattatttgaaggcagaagga
aaagtggagtgctaccgaaccctgcatcctgttcctttgtattcatcagtgtgaaccgtgccttttcaagccccaaggtcgcag
tggaagcctgtaacgccatgttgaaagagaacttccgactgtggcttcttactgtattattccagagtacgatgcctatttgga
catggttgacggagcttcatgctgcttagacactgccagtttttgccctgcaaagctgcgcagctttccaaagaaacactccta
tttggaacccacaatacgatcggcagtgccttcagcgatccagaacacgctccagaacgtcctggcagctgccacaaaa
agaaattgcaatgtcacgcaaatgagagaattgcccgtattggattcggcggcctttaatgtggaatgcttcaagaaatatgc
gtgtaataatgaatattgggaaacgtttaaagaaaaccccatcaggcttactgaagaaaacgtggtaaattacattaccaa
attaaaaggaccaaaagctgctgctcttttgcgaagacacataatttgaatatgttgcaggacataccaatggacaggtttgt
aatggacttaaagagagacgtgaaagtgactccaggaacaaaacatactgaagaacggcccaaggtacaggtgatcc
aggctgccgatccgctagcaacagcgtatctgtgcggaatccaccgagagctggttaggagattaaatgcggtcctgcttc
cgaacattcatacactgtttgatatgtcggctgaagactttgacgctattatagccgagcacttccagcctggggattgtgttctg
gaaactgacatcgcgtcgtttgataaaagtgaggacgacgccatggctctgaccgcgttaatgattctggaagacttaggtg
tggacgcagagctgttgacgctgattgaggcggcttcggcgaaatttcatcaatacatttgcccactaaaactaaatttaaat
tcggagccatgatgaaatctggaatgttcctcacactgtttgtgaacacagtcattaacattgtaatcgcaagcagagtgttga
gagaacggctaaccggatcaccatgtgcagcattcattggagatgacaatatcgtgaaaggagtcaaatcggacaaatta
atggcagacaggtgcgccacctggttgaatatggaagtcaagattatagatgctgtggtgggcgagaaagcgccttatttct
gtggagggttttattttgtgtgactccgtgaccggcacagcgtgccgtgtggcagacccctaaaaaggctgtttaagcttggc
aaacctctggcagcagacgatgaacatgatgatgacaggagaagggcattgcatgaagagtcaacacgctggaaccg
agtgggtattctttcagagctgtgcaaggcagtagaatcaaggtatgaaaccgtaggaacttccatcatagttatggccatga
ctactctagctagcagtgttaaatcattcagctacctgagaggggcccctataactctctacggctaacctgaatggactacg
acatagtctagtccgccaagtctagaccatgtctggtcgtaaagctcagggaaaaaccctgggcgtcaatatggtacgacg
aggagttcgctccttgtcaaacaaaataaaacaaaaaacaaaacaaattggaaacagacctggaccttcaagaggtgtt
caaggatttatctttttcttttgttcaacattttgactggaaaaaagatcacagcccacctaaagaggttgtggaaaatgctgga
cccaagacaaggcttggctgttctaaggaaagtcaagagagtggtggccagtttgatgagaggattgtcctcaaggaaac
gccgttcccatgatgttctgactgtgcaattcctaattttgggaatgctgttgatgacgggtggagtgaccttggtcggaaaaa
cagatggttgctcctaaatgtgacatctgaggacctcgggaaaacattctctgtgggcacaggcaactgcacaacaaacat
tttggaagccaagtactggtgcccagactcaatggaatacaactgtcccaatctcagtccaagagaggagccagatgaca
ttgattgctggtgctatggggtggaaaacgttagagtcgcatatggtaagtgtgactcagcaggcaggtctaggaggtcaag
aagggccattgacttgcctacgcatgaaaaccatggtttgaagacccggcaagaaaaatggatgactggaagaatgggt gaaaggcaactccaaaagattgagagatggttcgtgaggaaccccttttttgcagtgacggctctgaccattgcctaccttgt
gggaagcaacatgacgcaacgagtcgtgattgccctactggtcttggctgttggtccggcctactcagctcactgcattgga
attactgacagggatttcattgagggggtgcatggaggaacttgggttcagctaccctggagcaagacaagtgtgtcactgt
tatggcccctgacaagccttcattggacatctcactagagacagtagccattgatagacctgctgaggtgaggaaagtgtgt
tacaatgcagttctcactcatgtgaagattaatgacaagtgccccagcactggagaggcccacctagctgaagagaacga
aggggacaatgcgtgcaagcgcacttattctgatagaggctggggcaatggctgtggcctatttgggaaagggagcattgt
ggcatgcgccaaattcacttgtgccaaatccatgagtttgtttgaggttgatcagaccaaaattcagtatgtcatcagagcac
aattgcatgtaggggccaagcaggaaaattggaataccgacattaagactctcaagtttgatgccctgtcaggctcccagg
aagtcgagttcattgggtatggaaaagctacactggaatgccaggtgcaaactgcggtggactttggtaacagttacatcgc
tgagatggaaacagagagctggatagtggacagacagtgggcccaggacttgaccctgccatggcagagtggaagtgg
cggggtgtggagagagatgcatcatcttgtcgaatttgaacctccgcatgccgccactatcagagtactggccctgggaaa
ccaggaaggctccttgaaaacagctcttactggcgcaatgagggttacaaaggacacaaatgacaacaaccttttacaaa
ctacatggtggacatgtttcttgcagagtgaaattgtcagctttgacactcaaggggacatcctacaaaatatgcactgacaa
aatgttttttgtcaagaacccaactgacactggccatggcactgttgtgatgcaggtgaaagtgtcaaaaggagcccctgc
aggattccagtgatagtagctgatgatcttacagcggcaatcaataaaggcattttggttacagttaacccccatcgcctcaac
caatgatgatgaagtgctgattgaggtgaacccaccttttggagacagctacattatcgttgggagaggagattcacgtctca
cttaccagtggcacaaagagggaagctcaataggaaagttgttcactcagaccatgaaaggcgtggaacgcctggccgt
catgggagacaccgcctgggatttcagctccgctggagggttcttcacttcggttgggaaaggaattcatacggtgtttggctc
tgcctttcaggggctatttggcggcttgaactggataacaaaggtcatcatgggggcggtacttatatgggttggcatcaaca
caagaaacatgacaatgtccatgagcatgatcttggtaggagtgatcatgatgttttgtctctaggagttggggcgtaagcg
gcccctataactctctacggctaacctgaatggactacgacatagtctagtccgccaagtctagagcttaccatgaccgagt
acaagcccacggtgcgcctcgccacccgcgacgacgtcccccagggccgtacgcacctcgccgccgcgttcgccgact
accccgccacgcgccacaccgtcgatccggaccgccacatcgagcgggtcaccgagctgcaagaactcttcctcacgc
gcgtcgggctcgacatcggcaaggtgtgggtcgcggacgacggcgccgcggtggcggtctggaccacgccggagagc
gtcgaagcgggggcggtgttcgccgagatcggcccgcgcatggccgagttgagcggttcccggctggccgcgcagcaa
cagatggaaggcctcctggcgccgcaccggcccaaggagcccgcgtggttcctggccaccgtcggcgtctcgcccgac
caccagggcaagggtctgggcagcgccgtcgtgctcccggagtggaggcggccgagcgcgccggggtgcccgcctt
cctggagacctccgcgccccgcaacctcccccttctacgagcggctcggcttcaccgtcaccgccgacgtcgagtgcccga
aggaccgcgcgacctggtgcatgacccgcaagcccggtgcctgacgcccgccccacgacccgcagcgcccgaccga
aaggagcgcacgaccccatgatcgctagaccatggggtaccgagtatgttacgtgcaaaggtgattgtcaccccccgaa
agaccatattgtgacacaccctcagtatcacgcccaaacatttacagccgcggtgtcaaaaaccgcgtggacgtggttaac
atccctgctgggaggatcagccgtaattattataattggcttggtgctggctactattgtggccatgtacgtgctgaccaaccag
aaacataattgaatacagcagcaattggcaagctgcttacatagaactcgcggcgattggcatgccgccttaaaattttattt
tatttttctttctttccgaatcggattttgttttaatatttcaaaaaaaaaaaaaaaaaaaaaaacgcgtcgagggaatt
aattcttgaagacgaaagggccaggtggcacttttcggggaaatgtgcgcggaacccctatttgtttattttctaaatacattc
aaatatgtatccgctcatgagacaataaccctgataaatgcttcaataatattgaaaaaggaagagtatgagtattcaacatt
tccgtgtcgcccttattcccttttttgcggcattttgccttcctgttttgctcacccagaaacgctggtgaaagtaaaagatgctga
agatcagttgggtgcacgagtgggttacatcgaactggatctcaacagcggtaagatccttgagagttttcgccccgaaga
acgttttccaatgatgagcacttttaaagttctgctatgtggcgcggtattatcccgtgttgacgccgggcaagagcaactcggt
cgccgcatacactattctcagaatgacttggttgagtactcaccagtcacagaaaagcatcttacggatggcatgacagtaa
gagaattatgcagtgctgccataaccatgagtgataacactgcggccaacttacttctgacaacgatcggaggaccgaag
gagctaaccgcttttttgcacaacatgggggatcatgtaactcgccttgatcgttgggaaccggagctgaatgaagccatac
caaacgacgagcgtgacaccacgatgcctgtagcaatggcaacaacgttgcgcaaactattaactggcgaactacttact
ctagcttcccggcaacaattaatagactggatggaggcggataaagttgcaggaccacttctgcgctcggcccttccggct
ggctggtttattgctgataaatctggagccggtgagcgtgggtctcgcggtatcattgcagcactggggccagatggtaagc
cctcccgtatcgtagttatctacacgacggggagtcaggcaactatggatgaacgaaatagacagatcgctgagataggt
gcctcactgattaagcattggtaactgtcagaccaagtttactcatatatactttagattgatttaaaacttcatttttaatttaaaag
gatctaggtgaagatccttttgataatctcatgaccaaaatcccttaacgtgagttttcgttccactgagcgtcagaccccgta
gaaaagatcaaaggatcttcttgagatcctttttttctgcgcgtaatctgctgcttgcaaacaaaaaaaccaccgctaccagc
ggtggtttgtttgccggatcaagagctaccaactctttttccgaaggtaactggcttcagcagagcgcagataccaaatactgt
ccttctagtgtagccgtagttaggccaccacttcaagaactctgtagcaccgcctacatacctcgctctgctaatcctgttacca

Fig. 8N gtggctgctgccagtggcgataagtcgtgtcttaccggggttggactcaagacgatagttaccggataaggcgcagcggtcg
ggctgaacgggggggttcgtgcacacagcccagcttggagcgaacgacctacaccgaactgagatacctacagcgtgag
cattgagaaagcgccacgcttcccgaagggagaaaggcggacaggtatccggtaagcggcagggtcggaacaggag
agcgcacgagggagcttccaggggggaaacgcctggtatctttatagtcctgtcgggtttcgccacctctgacttgagcgtcg
attttgtgatgctcgtcagggggcggagcctatggaaaaacgccagcaacgcgagctcgatttaggtgacactata
(SEQ ID NO: 9)

Fig. 8O gatgggcggcgcatgagagaagcccagaccaattacctacccaaaatggagaaagttcacgttgacatcgaggaaga
cagcccattcctcagagctttgcagcggagcttcccgcagtttgaggtagaagccaagcaggtcactgataatgaccatgc
taatgccagagcgttttcgcatctggcttcaaaactgatcgaaacggaggtggacccatccgacacgatccttgacattgga
agtgcgcccgcccgcagaatgtattctaagcacaagtatcattgtatctgtccgatgagatgtgcggaagatccggacagat
tgtataagtatgcaactaagctgaagaaaaactgtaaggaaataactgataaggaattggacaagaaaatgaaggagct
ggccgccgtcatgagcgaccctgacctggaaactgagactatgtgcctccacgacgacgagtcgtgtcgctacgaaggg
caagtcgctgtttaccaggatgtatacgcggttgacggaccgacaagtctctatcaccaagccaataagggagttagagtc
gcctactggataggctttgacaccaccccttttatgtttaagaacttggctggagcatatccatcatactctaccaactgggccg
acgaaaccgtgttaacggctcgtaacataggcctatgcagctctgacgttatggagcggtcacgtagagggatgtccattctt
agaaagaagtatttgaaaccatccaacaatgttcattctctgttggctcgaccatctaccacgagaagagggacttactga
ggagctggcacctgccgtctgtatttcacttacgtggcaagcaaaattacacatgtcggtgtgagactatagttagttgcgac
gggtacgtcgttaaaagaatagctatcagtccaggcctgatgggaagccttcaggctatgctgctacgatgcaccgcgag
ggattcttgtgctgcaaagtgacagacacattgaacggggagagggtctcttttcccgtgtgcacgtatgtgccagctacatt
gtgtgaccaaatgactggcatactggcaacagatgtcagtgcggacgacgcgcaaaaactgctggttgggctcaaccag
cgtatagtcgtcaacggtcgcacccagagaaacaccaataccatgaaaaattacctttttgcccgtagtggcccaggcattt
gctaggtgggcaaaggaatataaggaagatcaagaagatgaaaggccactaggactacgagatagacagttagtcatg
gggtgttgttgggcttttagaaggcacaagataacatctatttataagcgcccggatacccaaaccatcatcaaagtgaaca
gcgatttccactcattcgtgctgcccaggataggcagtaacacattggagatcgggctgagaacaagaatcaggaaaatg
ttagaggagcacaaggagccgtcacctctcattaccgccgaggacgtacaagaagctaagtgcgcagccgatgaggct
aaggaggtgcgtgaagccgaggagttgcgcgcagctctaccaccctttggcagctgatgttgaggagcccactctggaagc
cgatgtcgacttgatgttacaagaggctggggccggctcagtggagacacctcgtggcttgataaaggttaccagctacga
tggcgaggacaagatcggctcttacgctgtgctttctccgcaggctgtactcaagagtgaaaaattatcttgcatccaccctct
cgctgaacaagtcatagtgataacacactctggccgaaaagggcgttatgccgtggaaccataccatggtaaagtagtgg
tgccagagggacatgcaatacccgtccaggactttcaagctctgagtgaaagtgccaccattgtgtacaacgaacgtgagt
tcgtaaacaggtacctgcaccatattgccacacatggaggagcgctgaacactgatgaagaatattacaaaactgtcaag
cccagcgagcacgacggcgaatacctgtacgacatcgacaggaaacagtgcgtcaagaagaactagtcactgggct
agggctcacaggcgagctggtggatcctcccttccatgaattcgcctacgagagtctgagaacacgaccagccgctcctta
ccaagtaccaaccatagggggtgtatggcgtgccaggatcaggcaagtctggcatcattaaaagcgcagtcaccaaaaaa
gatctagtggtgagcgccaagaaagaaaactgtgcagaaattataagggacgtcaagaaaatgaaagggctggacgtc
aatgccagaactgtggactcagtgctcttgaatggatgcaaacaccccgtagagaccctgtatattgacgaagcttttgcttgt
catgcaggtactctcagagcgctcatagccattataagacctaaaaaggcagtgctctgcggggatcccaaacagtgcgg
ttttttttaacatgatgtgcctgaaagtgcattttaaccacgagatttgcacacaagtcttccacaaaagcatctctcgccgttgca
ctaaatctgtgacttcggtcgtccaaccttgttttacgacaaaaaaatgagaacgacgaatccgaaagagactaagattgt
gattgacactaccggcagtaccaaacctaagcaggacgatctcattctcacttgtttcagagggtgggtgaagcagttgcaa
atagattacaaaggcaacgaaataatgacggcagctgcctctcaagggctgacccgtaaaggtgtgtatgccgttcggta
caaggtgaatgaaaatcctctgtacgcacccacctcagaacatgtgaacgtcctactgacccgcacggaggaccgcatc
gtgtggaaaacactagccggcgacccatggataaaaacactgactgccaagtaccctgggaatttcactgccacgatag
aggagtggcaagcagagcatgatgccatcatgaggcacatcttggagagaccggaccctaccgacgtcttccagaataa
ggcaaacgtgtgttgggccaaggcttagtgccggtgctgaagaccgctggcatagacatgaccactgaacaatggaac
actgtggattattttgaaacggacaaagctcactcagcagagatagtattgaaccaactatgcgtgaggttctttggactcgat

Fig. 8P ctggactccggtctattttctgcacccactgttccgttatccattaggaataatcactgggataactccccgtcgcctaacatgta
cgggctgaataaagaagtggtccgtcagctctctcgcaggtacccacaactgcctcgggcagttgccactggaagagtct
atgacatgaacactggtacactgcgcaattatgatccgcgcataaacctagtacctgtaaacagaagactgcctcatgcttt
agtcctccaccataatgaacacccacagagtgacttttcttcattcgtcagcaaattgaagggcagaactgtcctggtggtcg
gggaaaagttgtccgtcccaggcaaaatggttgactggttgtcagaccggcctgaggctaccttcagagctcggctggattt
aggcatcccaggtgatgtgcccaaatatgacataatatttgttaatgtgaggaccccatataaataccatcactatcagcagt
gtgaagaccatgccattaagcttagcatgttgaccaagaaagcttgtctgcatctgaatcccggcggaacctgtgtcagcat
aggttatggttacgctgacagggccagcgaaagcatcattggtgctatagcgcggcagttcaagttttcccgggtatgcaaa
ccgaaatcctcacttgaagagacggaagttctgtttgtattcattgggtacgatcgcaaggcccgtacgcacaatccttacaa
gctttcatcaaccttgaccaacatttatacaggttccagactccacgaagccggatgtgcaccctcatatcatggtgcgag
gggatattgccacggccaccgaaggagtgattataaatgctgctaacagcaaaggacaacctggcggagggtgtgcg
gagcgctgtataagaaattcc:ggaaagcttcgatttacagccgatcgaagtaggaaaagcgcgactggtcaaaggtgc
agctaaacatatcattcatgccgtaggaccaaacttcaacaaagtttcggaggttgaaggtgacaaacagttggcagagg
cttatgagtccatcgctaagattgtcaacgataacaattacaagtcagtagcgattccactgttgtccaccggcatcttttccgg
gaacaaagatcgactaacccaatcattgaaccatttgctgacagctttagacaccactgatgcagatgtagccatatactgc
agggacaagaaatgggaaagactctcaaggaagcagtggctaggagagaagcagtggaggagatatgcatatccga
cgactcttcagtgacagaacctgatgcagagctggtgaggtgcatccgaagagttctttggctggaaggaagggctaca
gcacaagcgatggcaaaactttctcatatttggaagggaccaagtttcaccaggcggccaaggatatagcagaaattaat
gccatgtggcccgttgcaacggaggccaatgagcaggtatgcatgtatatcctcggagaaagcatgagcagtattaggtc
gaaatgccccgtcgaagagtcggaagcctccacaccacctagcacgctgccttgcttgtgcatccatgccatgactccaga
aagagtacagcgcctaaaagcctcacgtccagaacaaattactgtgtgctcatcctttccattgccgaagtatagaatcact
ggtgtgcagaagatccaatgctcccagcctatattgttctcaccgaaagtgcctgcgtatattcatccaaggaagtatctcgtg
gaaacaccaccggtagacgagactccggagccatcggcagagaaccaatccacagaggggacacctgaacaacca
ccacttataaccgaggatgagaccaggactagaacgcctgagccgatcatcatcgaagaggaagaagaggatagcat
aagtttgctgtcagatggcccgacccaccaggtgctgcaagtcgaggcagacattcacgggccgccctctgtatctagctc
atcctggtccattcctcatgcatccgactttgatgtggacagtttatccatacttgacaccctggagggagctagcgtgaccag
cggggcaacgtcagccgagactaactcttacttcgcaaagagtatggagtttctggcgcgaccggtgcctgcgcctcgaac
agtattcaggaaccctccacatcccgctccgcgcacaagaacaccgtcacttgcacccagcagggcctgctcgagaacc
agcctagtttccaccccgccaggcgtgaatagggtgatcactagagaggagctcgaggcgcttacccccgtcacgcactcc
tagcaggtcggtctcgagaaccagcctggtctccaacccgccaggcgtaaatagggtgattacaagagaggagtttgag
gcgttcgtagcacaacaacaatgacggtttgatgcgggtgcatacatctttcctccgacaccggtcaagggcatttacaac
aaaaatcagtaaggcaaacggtgctatccgaagtggtgttggagaggaccgaattggagatttcgtatgccccgcgcctc
gaccaagaaaaagaagaattactacgcaagaaattacagttaaatcccacacctgctaacagaagcagataccagtcc
aggaaggtggagaacatgaaagccataacagctagacgtattctgcaaggcctagggcattatttgaaggcagaagga
aaagtggagtgctaccgaaccctgcatcctgttcctttgtattcatcagtgtgaaccgtgccttttcaagccccaaggtcgcag
tggaagcctgtaacgccatgttgaaagagaacttccgactgtggcttcttactgtattattccagagtacgatgcctatttgga
catggttgacggagcttcatgctgcttagacactgccagttttttgccctgcaaagctgcgcagctttccaaagaaacactccta
tttggaacccacaatacgatcggcagtgccttcagcgatccagaacacgctccagaacgtcctggcagctgccacaaaa
agaaattgcaatgtcacgcaaatgagagaattgcccgtattggattcggcggcctttaatgtggaatgcttcaagaaatatgc
gtgtaataatgaatattgggaaacgtttaaagaaaacccatcaggcttactgaagaaaacgtggtaaattacattaccaa
attaaaaggaccaaaagctgctgctcttttgcgaagacacataatttgaatatgttgcaggacataccaatggacaggtttgt
aatggacttaaagagagacgtgaaagtgactccaggaacaaaacactgaagaacggcccaaggtacaggtgatcc
aggctgccgatccgctagcaacagcgtatctgtgcggaatccaccgagagctggttaggagattaaatgcggtcctgcttc
cgaacattcatacactgtttgatatgtcggctgaagactttgacgctattatagccgagcacttccagcctggggattgtgttctg
gaaactgacatcgcgtcgtttgataaaagtgaggacgacgccatggctctgaccgcgttaatgattctggaagacttaggtg
tggacgcagagctgttgacgctgattgaggcggctttcggcgaaatttcatcaatacatttgcccactaaaactaaatttaaat
tcggagccatgatgaaatctggaatgttcctcacactgtttgtgaacacagtcattaacattgtaatcgcaagcagagtgttga
gagaacggctaaccggatcaccatgtgcagcattcattggagatgacaatatcgtgaaggagtcaaatcggacaaatta
atggcagacaggtgcgccacctggttgaatatggaagtcaagattatagatgctgtggtgggcgagaaagcgccttatttct
gtgagggtttattttgtgtgactccgtgaccggcacagcgtgccgtgtggcagaccccctaaaaaggctgtttaagcttggc
aaacctctggcagcagacgatgaacatgatgatgacaggagaagggcattgcatgaagagtcaacacgctggaaccg agtgggtattctttcagagctgtgcaaggcagtagaatcaaggtatgaaaccgtaggaacttccatcatagttatggccatga
ctactctagctagcagtgttaa:itcattcagctacctgagaggggcccctataactctctacggctaacctgaatggactacg
acatagtctagtccgccaagtctagaccatgagcggccggaaggctcagggcaagaccctgggcgtgaacatggtgag
gcgcggcgtgcgcagcctctccaacaagatcaagcagaagaccaagcagatcggcaacagacccggaccgagccg
gggcgtccaggggttcatcttcttcttcctgttcaacatcctcacaggtaagaagatcacggctcacctgaagaggctctgga
agatgctggaccctcgccagc:ggctcgcggtgctcagaaaggtgaagcgggtcgtcgcctccctgatgcgcggcctgtcc
tctcgcaagaggcgctcccacgatgtgctcaccgtccaattcctcattctggaatgctgctgatgactggcggcgtgaccctg
gtgcgcaagaaccgctggctgctgctgaatgtgaccagtgaggacctcgggtaagggcccctataactctctacggctaa
cctgaatggactacgacatagtctagtccgccaagtctagagcttaccatgaccgagtacaagcccacggtgcgcctcgc
cacccgcgacgacgtccccagggccgtacgcaccctcgccgccgcgttcgccgactaccccgccacgcgccacaccgt
cgatccggaccgccacatcgagcgggtcaccgagctgcaagaactcttcctcacgcgcgtcgggctcgacatcggcaag
gtgtgggtcgcggacgacggcgccgcggtggcggtctggaccacgccggagagcgtcgaagcgggggcggtgttcgc
cgagatcggcccgcgcatggccgagttgagcggttcccggctggccgcgcagcaacagatggaaggcctcctggcgcc
gcaccggcccaaggagcccgcgtggttcctggccaccgtcggcgtctcgcccgaccaccagggcaagggtctgggcag
cgccgtcgtgctccccggagtggaggcggccgagcgcgcggggtgcccgccttcctggagacctccgcgccccgcaa
cctccccttctacgagcggctcggcttcaccgtcaccgccgacgtcgaggtgcccgaaggaccgcgcacctggtgcatga
cccgcaagcccggtgcctgacgcccgccccacgacccgcagcgcccgaccgaaaggagcgcacgacccccatgatcg
ctagaccatggggtaccgagtatgttacgtgcaaaggtgattgtcaccccccgaaagaccatattgtgacacaccctcagt
atcacgcccaaacatttacagccgcggtgtcaaaaaccgcgtggacgtggttaacatccctgctgggaggatcagccgta
attattataattggcttggtgctggctactattgtggccatgtacgtgctgaccaaccagaaacataattgaatacagcagcaa
ttggcaagctgcttacatagaactcgcggcgattggcatgccgccttaaaattttttattttatttttcttttcttttccgaatcggatttt
gtttttaatatttcaaaaaaaaaaaaaaaaaaaaaaaacgcgtcgaggggaattaattcttgaagacgaaagggccag
gtggcacttttcggggaaatgtgcgcggaacccctatttgtttattttttctaaatacattcaaatatgtatccgctcatgagacaat
aaccctgataaatgcttcaataatattgaaaaaggaagagtatgagtattcaacatttccgtgtcgcccttattccttttttgcg
gcattttgccttcctgttttgctcacccagaaacgctggtgaaagtaaaagatgctgaagatcagttgggtgcacgagtgggt
tacatcgaactggatctcaacagcggtaagatccttgagagttttcgccccgaagaacgttttccaatgatgagcacttttaaa
gttctgctatgtggcgcggtattatcccgtgttgacgccgggcaagagcaactcggtcgccgcatacactattctcagaatga
cttggttgagtactcaccagtcacagaaaagcatcttacggatggcatgacagtaagagaattatgcagtgctgccataac
catgagtgataacactgcggccaacttacttctgacaacgatcggaggaccgaaggagctaaccgcttttttgcacaacat
gggggatcatgtaactcgccttgatcgttgggaaccggagctgaatgaagccataccaaacgacgagcgtgacaccacg
atgcctgtagcaatggcaacaacgttgcgcaaactattaactggcgaactacttactctagcttcccggcaacaattaatag
actggatggaggcggataaagttgcaggaccacttctgcgctcggcccttccggctggctggtttattgctgataaatctgga
gccggtgagcgtgggtctcgcggtatcattgcagcactggggccagatggtaagccctcccgtatcgtagttatctacacga
cggggagtcaggcaactatggatgaacgaaatagacagatcgctgagataggtgcctcactgattaagcattggtaactgt
cagaccaagtttactcatatatactttagattgatttaaaacttcatttttaatttaaaaggatctaggtgaagatccttttgataat
ctcatgaccaaaatcccttaacgtgagttttcgttccactgagcgtcagaccccgtagaaaagatcaaaggatcttcttgaga
tcctttttttctgcgcgtaatctgctgcttgcaaacaaaaaaaccaccgctaccagcggtggtttgtttgccggatcaagagcta
ccaactctttttccgaaggtaactggcttcagcagagcgcagataccaaatactgtccttctagtgtagccgtagttaggcca
ccacttcaagaactctgtagcaccgcctacatacctcgctctgctaatcctgttaccagtggctgctgccagtggcgataagt
cgtgtcttaccgggttggactcaagacgatagttaccggataaggcgcagcggtcgggctgaacggggggttcgtgcaca
cagcccagcttggagcgaacgacctacaccgaactgagatacctacagcgtgagcattgagaaagcgccacgcttccc
gaagggagaaaggcggacaggtatccggtaagcggcagggtcggaacaggagagcgcacgagggagcttccaggg
ggaaacgcctggtatctttatagtcctgtcgggtttcgccacctctgacttgagcgtcgatttttgtgatgctcgtcaggggggcg
gagcctatggaaaaacgccagcaacgcgagctcgatttaggtgacactata (SEQ ID NO: 10)

Fig. 8R

```
gatgggcggcgcatgagagaagcccagaccaattacctacccaaaatggagaaagttcacgttgacatcgaggaaga
cagcccattcctcagagctttgcagcggagcttcccgcagtttgaggtagaagccaagcaggtcactgataatgaccatgc
taatgccagagcgttttcgcatctggcttcaaaactgatcgaaacggaggtggacccatccgacacgatccttgacattgga
agtgcgcccgcccgcagaatgtattctaagcacaagtatcattgtatctgtccgatgagatgtgcggaagatccggacagat
tgtataagtatgcaactaagctgaagaaaaactgtaaggaaataactgataaggaattggacaagaaaatgaaggagct
ggccgccgtcatgagcgaccctgacctggaaactgagactatgtgcctccacgacgacgagtcgtgtcgctacgaaggg
caagtcgctgtttaccaggatgtatacgcggttgacggaccgacaagtctctatcaccaagccaataagggagttagagtc
gcctactggataggctttgacaccacccctttatgtttaagaacttggctggagcatatccatcatactctaccaactgggccg
acgaaaccgtgttaacggctcgtaacataggcctatgcagctctgacgttatggagcggtcacgtagagggatgtccattct
agaaagaagtatttgaaaccatccaacaatgttctattctctgttggctcgaccatctaccacgagaagagggacttactga
ggagctggcacctgccgtctgtatttcacttacgtggcaagcaaaattacacatgtcggtgtgagactatagttagttgcgac
gggtacgtcgttaaaagaatagctatcagtccaggcctgtatgggaagccttcaggctatgctgctacgatgcaccgcgag
ggattcttgtgctgcaaagtgacagacacattgaacggggagagggtctcttttcccgtgtgcacgtatgtgccagctacatt
gtgtgaccaaatgactggcatactggcaacagatgtcagtgcggacgacgcgcaaaaactgctggttgggctcaaccag
cgtatagtcgtcaacggtcgcacccagagaaacaccaataccatgaaaaattacctttgcccgtagtggcccaggcattt
gctaggtgggcaaaggaatataaggaagatcaagaagatgaaaggccactaggactacgagatagacagttagtcatg
gggtgttgttggcttttagaaggcacaagataacatctatttataagcgcccggatacccaaaccatcatcaaagtgaaca
gcgatttccactcattcgtgctgcccaggataggcagtaacacattggagatcgggctgagaacaagaatcaggaaaatg
ttagaggagcacaaggagccgtcacctctcattaccgccgaggacgtacaagaagctaagtgcgcagccgatgaggct
aaggaggtgcgtgaagccgaggagttgcgcgcagctctaccaccttttggcagctgatgttgaggagcccactctggaagc
cgatgtcgacttgatgttacaagaggctggggccggctcagtggagacacctcgtggcttgataaaggttaccagctacga
tggcgaggacaagatcggctcttacgctgtgctttctccgcaggctgtactcaagagtgaaaaattatcttgcatccaccctct
cgctgaacaagtcatagtgataacacactctggccgaaaagggcgttatgccgtggaaccataccatggtaaagtagtgg
tgccagagggacatgcaatacccgtccaggactttcaagctctgagtgaaagtgccaccattgtgtacaacgaacgtgagt
tcgtaaacaggtacctgcaccatattgccacacatggaggagcgctgaacactgatgaagaatattacaaaactgtcaag
cccagcgagcacgacggcgaatacctgtacgacatcgacaggaaacagtgcgtcaagaaagaactagtcactgggct
agggctcacaggcgagctggtggatcctcccttccatgaattcgcctacgagagtctgagaacacgaccagccgctcctta
ccaagtaccaaccatagggggtgtatggcgtgccaggatcaggcaagtctggcatcattaaaagcgcagtcaccaaaaaa
gatctagtggtgagcgccaagaaagaaaactgtgcagaaattataagggacgtcaagaaaatgaaagggctggacgtc
aatgccagaactgtggactcagtgctcttgaatggatgcaaacaccccgtagagaccctgtatattgacgaagcttttgcttgt
catgcaggtactctcagagcgctcatagccattataagacctaaaaaggcagtgctctgcggggatcccaaacagtgcgg
ttttttttaacatgatgtgcctgaaagtgcatttaaccacgagatttgcacacaagtcttccacaaaagcatctctcgccgttgca
ctaaatctgtgacttcggtcgtctcaaccttgttttacgacaaaaaaatgagaacgacgaatccgaaagagactaagattgt
gattgacactaccggcagtaccaaacctaagcaggacgatctcattctcacttgtttcagagggtgggtgaagcagttgcaa
atagattacaaaggcaacgatatgacggcagctgcctctcaagggctgacccgtaaaggtgtgtatgccgttcggtacaa
ggtgaatgaaaatcctctgtacgcacccacctcagaacatgtgaacgtcctactgacccgcacggaggaccgcatcgtgt
ggaaaacactagccggcgacccatggataaaaacactgactgccaagtaccctgggaatttcactgccacgatagagg
agtggcaagcagagcatgatgccatcatgaggcacatcttggagagaccggaccctaccgacgtcttccagaataaggc
aaacgtgtgttgggcccaaggctttagtgccggtgctgaagaccgctggcatagacatgaccactgaacaatggaacactg
tggattattttgaaacggacaaagctcactcagcagagatagtattgaaccaactatgcgtgaggttctttggactcgatctgg
actccggtctattttctgcacccactgttccgttatccattaggaataatcactgggataactccccgtcgcctaacatgtacgg
gctgaataaagaagtggtccgtcagctctctcgcaggtacccacaactgcctcgggcagttgccactggaagagtctatga
catgaacactggtacactgcgcaattatgatccgcgcataaacctagtacctgtaaacagaagactgcctcatgctttagtc
ctccaccataatgaacacccacagagtgacttttcttcattcgtcagcaaattgaagggcagaactgtcctggtggtcgggg
aaaagttgtccgtcccaggcaaaatggttgactggttgtcagaccggcctgaggctaccttcagagctcggctggatttagg
catcccaggtgatgtgcccaaatatgacataatatttgttaatgtgaggaccccatataaataccatcactatcagcagtgtg
aagaccatgccattaagcttagcatgttgaccaagaaagcttgtctgcatctgaatcccggcggaacctgtgtcagcatagg
ttatggttacgctgacagggccagcgaaagcatcattggtgctatagcgcggcagttcaagttttcccgggtatgcaaaccg
aaatcctcacttgaagagacggaagttctgtttgtattcattgggtacgatcgcaaggcccgtacgcacaatccttacaagctt
tcatcaacccttgaccaacatttatacaggttccagactccacgaagccggatgtgcaccctcatatcatgtggtgcgagggg
atattgccacggccaccgaaggagtgattataaatgctgctaacagcaaaggacaacctggcggagggggtgtgcggag
```

Fig. 8S cgctgtataagaaattcccggaaagcttcgatttacagccgatcgaagtaggaaaagcgcgactggtcaaaggtgcagct
aaacatatcattcatgccgtaggaccaaacttcaacaaagtttcggaggttgaaggtgacaaacagttggcagaggcttat
gagtccatcgctaagattgtcaacgataacaattacaagtcagtagcgattccactgttgtccaccggcatcttttccgggaa
caaagatcgactaacccaatcattgaaccatttgctgacagctttagacaccactgatgcagatgtagccatatactgcagg
gacaagaaatgggaaatgactctcaaggaagcagtggctaggagagaagcagtggaggagatatgcatatccgacga
ctcttcagtgacagaacctgatgcagagctggtgagggtgcatccgaagagttctttggctggaaggaagggctacagca
caagcgatggcaaaactttctcatatttggaagggaccaagtttcaccaggcggccaaggatatagcagaaattaatgcc
atgtggcccgttgcaacggaggccaatgagcaggtatgcatgtatatcctcggagaaagcatgagcagtattaggtcgaa
atgccccgtcgaagagtcggaagcctccacaccacctagcacgctgccttgcttgtgcatccatgccatgactccagaaag
agtacagcgcctaaaagcctcacgtccagaacaaattactgtgtgctcatcctttccattgccgaagtatagaatcactggtg
tgcagaagatccaatgctcccagcctatattgttctcaccgaaagtgcctgcgtatattcatccaaggaagtatctcgtggaa
acaccaccggtagacgagactccggagccatcggcagagaaccaatccacagaggggacacctgaacaaccacca
cttataaccgaggatgagaccaggactagaacgcctgagccgatcatcatcgaagaggaagaagaggatagcataagt
ttgctgtcagatggcccgacccaccaggtgctgcaagtcgaggcagacattcacgggccgccctctgtatctagctcatcct
ggtccattcctcatgcatccgactttgatgtggacagtttatccatacttgacaccctggagggagctagcgtgaccagcggg
gcaacgtcagccgagactaactcttacttcgcaaagagtatggagtttctggcgcgaccggtgcctgcgcctcgaacagta
ttcaggaaccctccacatcccgctccgcgcacaagaacaccgtcacttgcacccagcagggcctgctcgagaaccagcc
tagttttccaccccgccaggcgtgaataggggtgatcactagagaggagctcgaggcgcttaccccgtcacgcactcctagc
aggtcggtctcgagaaccagctggtctccaacccgccaggcgtaaatagggtgattacaagagaggagtttgaggcgttc
gtagcacaacaacaatgacggtttgatgcgggtgcatacatctttttcctccgacaccggtcaagggcatttacaacaaaaat
cagtaaggcaaacggtgctatccgaagtggtgttggagaggaccgaattggagatttcgtatgccccgcgcctcgaccaa
gaaaaagaagaattactacgcaagaaattacagttaaatcccacacctgctaacagaagcagataccagtccaggaag
gtggagaacatgaaagccataacagctagacgtattctgcaaggcctagggcattatttgaaggcagaaggaaaagtgg
agtgctaccgaaccctgcatcctgttcctttgtattcatctagtgtgaaccgtgccttttcaagccccaaggtcgcagtggaagc
ctgtaacgccatgttgaaagagaactttccgactgtggcttcttactgtattattccagagtacgatgcctatttggacatggttg
acggagcttcatgctgcttagacactgccagttttttgccctgcaaagctgcgcagcttttccaaagaaacactcctatttggaac
ccacaatacgatcggcagtgccttcagcgatccagaacacgctccagaacgtcctggcagctgccacaaaaagaaattg
caatgtcacgcaaatgagagaattgcccgtattggattcggcggcctttaatgtggaatgcttcaagaaatatgcgtgtaata
atgaatatgggaaacgtttaaagaaaaccccatcaggcttactgaagaaaacgtggtaaattacattaccaaattaaaag
gaccaaaagctgctgctctttttgcgaagacacataatttgaatatgttgcaggacataccaatggacaggtttgtaatggact
taaagagagacgtgaaagtgactccaggaacaaaacatactgaagaacggcccaaggtacaggtgatccaggctgcc
gatccgctagcaacagcgtatctgtgcggaatccaccgagagctggttaggagattaaatgcggtcctgcttccgaacattc
atacactgtttgatatgtcggctgaagactttgacgctattatagccgagcacttccagcctggggattgtgttctggaaactga
catcgcgtcgtttgataaaagtgaggacgacgccatggctctgaccgcgttaatgattctggaagacttaggtgtggacgca
gagctgttgacgctgattgaggcggctttcggcgaaatttcatcaatacatttgcccactaaaactaaatttaaattcggagcc
atgatgaaatctggaatgttcctcacactgtttgtgaacacagtcattaacattgtaatcgcaagcagagtgttgagagaacg
gctaaccggatcaccatgtgcagcattcattggagatgacaatatcgtgaaaggagtcaaatcggacaaattaatggcag
acaggtgcgccacctggttgaatatggaagtcaagattatagatgctgtggtgggcgagaaagcgccttattctgtggagg
gtttattttgtgtgactccgtgaccggcacagcgtgccgtgtggcagacccccctaaaaaggctgtttaagcttggcaaacctct
ggcagcagacgatgaacatgatgatgacaggagaagggcattgcatgaagagtcaacacgctggaaccgagtgggta
ttctttcagagctgtgcaaggcagtagaatcaaggtatgaaaccgtaggaacttccatcatagttatggccatgactactcta
gctagcagtgttaaatcattcagctacctgagaggggcccctataactctctacggctaacctgaatggactacgacatagt
ctagtccgccaagtctagaccatgagcggccggaaggctcagggcaagaccctgggcgtgaacatggtgaggcgcgg
cgtgcgcagcctctccaacaagatcaagcagaagaccaagcagatcggcaacagacccggaccgagccggggcgtc
caggggttcatcttcttcttcctgttcaacatcctcacaggtaagaagatcacggctcacctgaagaggctctggaagatgct
ggaccctcgccaggggctcgcggtgctcagaaaggtgaagcgggtcgtcgcctccctgatgcgcggcctgtcctctcgca
agaggcgctcccacgatgtgctcaccgtccaattcctcattctgggaatgctgttgatgacgggtggagtgaccttggtgcgg
aaaaacagatggttgctcctaaatgtgacatctgaggacctcgggaaaacattctctgtgggcacaggcaactgcacaac
aaacattttggaagccaagtactggtgcccagactcaatggaatacaactgtcccaatctcagtccaagagaggagccag
atgacattgattgctggtgctatggggtggaaaacgttagagtcgcatatggtaagtgtgactcagcaggcaggtctaggag
gtcaagaagggccattgacttgcctacgcatgaaaaccatggtttgaagacccggcaagaaaaatggatgactggaaga

Fig. 8T

```
atgggtgaaaggcaactccaaaagattgagagatggttcgtgaggaaccccttttttgcagtgacggctctgaccattgcct
accttgtgggaagcaacatgacgcaacgagtcgtgattgccctactggtcttggctgttggtccggcctactcagctcactgc
attggaattactgacagggatttcattgagggggtgcatggaggaacttgggtttcagctaccctggagcaagacaagtgtg
tcactgttatggcccctgacaagccttcattggacatctcactagagacagtagccattgatagacctgctgaggtgaggaa
agtgtgttacaatgcagttctcactcatgtgaagattaatgacaagtgccccagcactggagaggcccacctagctgaaga
gaacgaaggggacaatgcgtgcaagcgcacttattctgatagaggctggggcaatggctgtggcctatttgggaaaggg
agcattgtggcatgcgccaaattcacttgtgccaaatccatgagtttgtttgaggttgatcagaccaaaattcagtatgtcatca
gagcacaattgcatgtaggggccaagcaggaaaattggaataccgacattaagactctcaagtttgatgccctgtcaggct
cccaggaagtcgagttcattgggtatggaaaagctacactggaatgccaggtgcaaactgcggtggactttggtaacagtt
acatcgctgagatggaaacagagagctggatagtggacagacagtgggcccaggacttgaccctgccatggcagagtg
gaagtggcgggtgtggagagagatgcatcatcttgtcgaatttgaacctccgcatgccgccactatcagagtactggccct
gggaaaccaggaaggctccttgaaaacagctcttactggcgcaatgagggttacaaaggacacaaatgacaacaacct
ttacaaactacatggtggacatgtttcttgcagagtgaaattgtcagctttgacactcaaggggacatcctacaaaatatgca
ctgacaaaatgtttttttgtcaagaacccaactgacactggccatggcactgttgtgatgcaggtgaaagtgtcaaaaggagc
cccctgcaggattccagtgatagtagctgatgatcttacagcggcaatcaataaaggcattttggttacagttaaccccatcg
cctcaaccaatgatgatgaagtgctgattgaggtgaacccaccttttggagacagctacattatcgttgggagaggagattc
acgtctcacttaccagtggcacaaagagggaagctcaataggaaagttgttcactcagaccatgaaaggcgtggaacgc
ctggccgtcatgggagacaccgcctgggatttcagctccgctggagggttcttcacttcggttgggaaaggaattcatacggt
gtttggctctgcctttcaggggctatttggcggcttgaactggataacaaaggtcatcatgggggcggtacttatatgggttggc
atcaacacaagaaacatgacaatgtccatgagcatgatcttggtaggagtgatcatgatgttttgtctctaggagttggggc
gtaagcggccccctataactctctacggctaacctgaatggactacgacatagtctagtccgccaagtctagagcttaccatg
accgagtacaagcccacggtgcgcctcgccacccgcgacgacgtccccagggccgtacgcaccctcgccgccgcgttc
gccgactaccccgccacgcgccacaccgtcgatccggaccgccacatcgagcgggtcaccgagctgcaagaactcttc
ctcacgcgcgtcgggctcgacatcggcaaggtgtgggtcgcggacgacggcgccgcggtggcggtctggaccacgccg
gagagcgtcgaagcgggggcggtgttcgccgagatcggcccgcgcatggccgagttgagcggttcccggctggccgcg
cagcaacagatggaaggcctcctggcgccgcaccggcccaaggagcccgcgtggttcctggccaccgtcggcgtctcg
cccgaccaccagggcaagggtctgggcagcgccgtcgtgctccccggagtggaggcggccgagcgcgccggggtgc
ccgccttcctggagacctccgcgccccgcaacctcccccttctacgagcggctcggcttcaccgtcaccgccgacgtcgag
gtgcccgaaggaccgcgcacctgatgcatgacccgcaagcccggtgcctgacgcccgccccacgacccgcagcgccc
gaccgaaaggagcgcacgaccccatgatcgctagaccatgggggtaccgagtatgttacgtgcaaaggtgattgtcaccc
cccgaaagaccatattgtgacacaccctcagtatcacgcccaaacatttacagccgcggtgtcaaaaaccgcgtggacgt
ggttaacatccctgctgggaggatcagccgtaattattataattggcttggtgctggctactattgtggccatgtacgtgctgac
caaccagaaacataattgaatacagcagcaattggcaagctgcttacatagaactcgcggcgattgcatgccgccttaaa
atttttattttattttttcttttcttttccgaatcggattttgtttttaatatttcaaaaaaaaaaaaaaaaaaaaaaaaaacgcgtcgag
gggaattaattcttgaagacgaaagggccaggtggcacttttcggggaaatgtgcgcggaacccctatttgtttattttttctaaa
tacattcaaatatgtatccgctcatgagacaataaccctgataaatgcttcaataatattgaaaaaggaagagtatgagtatt
caacatttccgtgtcgcccttattccctttttttgcggcattttgccttcctgttttttgctcacccagaaacgctggtgaaagtaaaag
atgctgaagatcagttgggtgcacgagtgggttacatcgaactggatctcaacagcggtaagatccttgagagttttcgccc
cgaagaacgttttccaatgatgagcacttttaaagttctgctatgtggcgcggtattatcccgtgttgacgccgggcaagagc
aactcggtcgccgcatacactattctcagaatgacttggttgagtactcaccagtcacagaaaagcatcttacggatggcat
gacagtaagagaattatgcagtgctgccataaccatgagtgataacactgcggccaacttacttctgacaacgatcggag
gaccgaaggagctaaccgcttttttgcacaacatgggggatcatgtaactcgccttgatcgttgggaaccggagctgaatg
aagccataccaaacgacgagcgtgacaccacgatgcctgtagcaatggcaacaacgttgcgcaaactattaactggcg
aactacttactctagcttcccggcaacaattaatagactggatggaggcggataaagttgcaggaccacttctgcgctcggc
ccttccggctggctggtttattgctgataaatctggagccggtgagcgtgggtctcgcggtatcattgcagcactggggccag
atggtaagccctcccgtatcgtagttatctacacgacggggagtcaggcaactatggatgaacgaaatagacagatcgct
gagataggtgcctcactgattaagcattggtaactgtcagaccaagtttactcatatatactttagattgatttaaaacttcattttt
aatttaaaaggatctaggtgaagatcctttttgataatctcatgaccaaaatcccttaacgtgagttttcgttccactgagcgtca
gaccccgtagaaaagatcaaaggatcttcttgagatccttttttttctgcgcgtaatctgctgcttgcaaacaaaaaaaccacc
gctaccagcggtggtttgtttgccggatcaagagctaccaactctttttccgaaggtaactggcttcagcagagcgcagatac
caaatactgtccttctagtgtagccgtagttaggccaccacttcaagaactctgtagcaccgcctacatacctcgctctgctaa
```

Fig. 8U tcctgttaccagtggctgctgccagtggcgataagtcgtgtcttaccgggttggactcaagacgatagttaccggataaggcg
cagcggtcgggctgaacggggggttcgtgcacacagcccagcttggagcgaacgacctacaccgaactgagataccta
cagcgtgagcattgagaaagcgccacgcttcccgaagggagaaaggcggacaggtatccggtaagcggcagggtcg
gaacaggagagcgcacgacggagcttccaggggaaacgcctggtatctttatagtcctgtcgggtttcgccacctctgac
ttgagcgtcgattttgtgatgctcgtcagggggcggagcctatggaaaaacgccagcaacgcgagctcgatttaggtga
cactata (SEQ ID NO: 11)

Fig. 8V

WN RepliVAX p0    Fig. 10    WN RepliVAX p10

Fig. 11

Titer (IU/ml) vs Hours Post-infection

- RepliVAX from BHK
- RepliVAX obtained from WHO Vero (SFM)

SEQUENCE LISTING

<160> NUMBER OF SEQ ID NOS: 42

<210> SEQ ID NO 1
<211> LENGTH: 423
<212> TYPE: DNA
<213> ORGANISM: artificial sequence
<220> FEATURE:
<223> OTHER INFORMATION: a synthetic C gene of Yellow fever virus

<400> SEQUENCE: 1

```
atgagcggcc ggaaggctca gggcaagacc ctgggcgtga acatggtgag      50
gcgcggcgtg cgcagcctct ccaacaagat caagcagaag accaagcaga     100
tcggcaacag acccggaccg agccggggcg tccaggggtt catcttcttc     150
ttcctgttca acatcctcac aggtaagaag atcacggctc acctgaagag     200
```

-continued

```
gctctggaag atgctggacc ctcgccaggg gctcgcggtg ctcagaaagg        250
tgaagcgggt cgtcgcctcc ctgatgcgcg gcctgtcctc tcgcaagagg        300
cgctcccacg atgtgctcac cgtccaattc ctcattctgg gaatgctgct        350
gatgactggc ggcgtgaccc tggtgcgcaa gaaccgctgg ctgctgctga        400
atgtgaccag tgaggacctc ggg                                     423
```

```
<210> SEQ ID NO 2
<211> LENGTH: 11
<212> TYPE: RNA
<213> ORGANISM: artificial sequence
<220> FEATURE:
<223> OTHER INFORMATION: cyclization sequence in C gene of Venezuelan
      Equine Encephalitis replicon (VEErep)

<400> SEQUENCE: 2
gucaauaugc u                                                  11

<210> SEQ ID NO 3
<211> LENGTH: 11
<212> TYPE: RNA
<213> ORGANISM: artificial sequence
<220> FEATURE:
<223> OTHER INFORMATION: mutated cyclization sequence in C gene
      of Venezuelan Equine Encephalitis replicon

<400> SEQUENCE: 3
gugaacaugu u                                                  11

<210> SEQ ID NO 4
<211> LENGTH: 8
<212> TYPE: PRT
<213> ORGANISM: artificial sequence
<220> FEATURE:
<223> OTHER INFORMATION: amino acid sequence in the RepliVax genome
      that has the signal peptidase cleavage site

<400> SEQUENCE: 4

Ser Val Gly Ala Val Thr Leu Ser
  5

<210> SEQ ID NO 5
<211> LENGTH: 8
<212> TYPE: PRT
<213> ORGANISM: artificial sequence
<220> FEATURE:
<223> OTHER INFORMATION: amino acid sequence in the RepliVax genome
      that has the NS2B/NS3 cleavage site

<400> SEQUENCE: 5

Gln Lys Lys Arg Gly Gly Lys Thr
  5

<210> SEQ ID NO 6
<211> LENGTH: 14295
<212> TYPE: DNA
<213> ORGANISM: artificial sequence
<220> FEATURE:
<223> OTHER INFORMATION: sequence of Yellow Fever pseudoinfectious
      virus plasmid

<400> SEQUENCE: 6
gagtaaatcc tgtgtgctaa ttgaggtgca ttggtctgca aatcgagttg         50
ctaggcaata aacacatttg gattaatttt aatcgttcgt tgagcgatta        100
```

| | |
|---|---|
| gcagagaact gaccagaaca tgtctggtcg taaagctcag ggaaaaaccc | 150 |
| tgggcgtcaa tatggtacga cgaggagttc gctccttgtc aaacaccatg | 200 |
| gtgagcaagg gcgaggagct gttcaccggg gtggtgccca tcctggtcga | 250 |
| gctggacggc gacgtaaacg gccacaagtt cagcgtgtcc ggcgagggcg | 300 |
| agggcgatgc cacctacggc aagctgaccc tgaagttcat ctgcaccacc | 350 |
| ggcaagctgc ccgtgccctg gcccaccctc gtgaccaccc tgacctacgg | 400 |
| cgtgcagtgc ttcagccgct accccgacca catgaagcag cacgacttct | 450 |
| tcaagtccgc catgcccgaa ggctacgtcc aggagcgcac catcttcttc | 500 |
| aaggacgacg gcaactacaa gacccgcgcc gaggtgaagt tcgagggcga | 550 |
| caccctggtg aaccgcatcg agctgaaggg catcgacttc aaggaggacg | 600 |
| gcaacatcct ggggcacaag ctggagtaca actacaacag ccacaacgtc | 650 |
| tatatcatgg ccgacaagca gaagaacggc atcaaggtga acttcaagat | 700 |
| ccgccacaac atcgaggacg gcagcgtgca gctcgccgac cactaccagc | 750 |
| agaacacccc catcggcgac ggccccgtgc tgctgcccga caaccactac | 800 |
| ctgagcaccc agtccgccct gagcaaagac cccaacgaga gcgcgatca | 850 |
| catggtcctg ctggagttcg tgaccgccgc cgggatcact ctcggcatgg | 900 |
| acgagctgta caagcttgga ttgtcctcaa ggaaacgccg ttcccatgat | 950 |
| gttctgactg tgcaattcct aattttggga atgctgttga tgacgggtgg | 1000 |
| agtgaccttg gtgcggaaaa acagatggtt gctcctaaat gtgacatctg | 1050 |
| aggacctcgg gaaaacattc tctgtgggca caggcaactg cacaacaaac | 1100 |
| attttggaag ccaagtactg gtgcccagac tcaatggaat acaactgtcc | 1150 |
| caatctcagt ccaagagagg agccagatga cattgattgc tggtgctatg | 1200 |
| gggtggaaaa cgttagagtc gcatatggta agtgtgactc agcaggcagg | 1250 |
| tctaggaggt caagaagggc cattgacttg cctacgcatg aaaaccatgg | 1300 |
| tttgaagacc cggcaagaaa aatggatgac tggaagaatg ggtgaaaggc | 1350 |
| aactccaaaa gattgagaga tggttcgtga ggaaccccett ttttgcagtg | 1400 |
| acggctctga ccattgccta ccttgtggga agcaacatga cgcaacgagt | 1450 |
| cgtgattgcc ctactggtct tggctgttgg tccggcctac tcagctcact | 1500 |
| gcattggaat tactgacagg gatttcattg aggggtgca tggaggaact | 1550 |
| tgggtttcag ctaccctgga gcaagacaag tgtgtcactg ttatggcccc | 1600 |
| tgacaagcct tcattggaca tctcactaga gacagtagcc attgatagac | 1650 |
| ctgctgaggt gaggaaagtg tgttacaatg cagttctcac tcatgtgaag | 1700 |
| attaatgaca agtgccccag cactggagag gcccacctag ctgaagagaa | 1750 |
| cgaaggggac aatgcgtgca agcgcactta ttctgataga ggctggggca | 1800 |
| atggctgtgg cctatttggg aaagggagca ttgtggcatg cgccaaattc | 1850 |
| acttgtgcca aatccatgag tttgtttgag gttgatcaga ccaaaattca | 1900 |
| gtatgtcatc agagcacaat tgcatgtagg ggccaagcag gaaaattgga | 1950 |
| ataccgacat taagactctc aagtttgatg ccctgtcagg ctcccaggaa | 2000 |
| gtcgagttca ttgggtatgg aaaagctaca ctggaatgcc aggtgcaaac | 2050 |
| tgcggtggac tttggtaaca gttacatcgc tgagatggaa acagagagct | 2100 |

-continued

| | |
|---|---|
| ggatagtgga cagacagtgg gcccaggact tgaccctgcc atggcagagt | 2150 |
| ggaagtggcg gggtgtggag agagatgcat catcttgtcg aatttgaacc | 2200 |
| tccgcatgcc gccactatca gagtactggc cctgggaaac caggaaggct | 2250 |
| ccttgaaaac agctcttact ggcgcaatga gggttacaaa ggacacaaat | 2300 |
| gacaacaacc tttacaaact acatggtgga catgtttctt gcagagtgaa | 2350 |
| attgtcagct ttgacactca aggggacatc ctacaaaata tgcactgaca | 2400 |
| aaatgttttt tgtcaagaac ccaactgaca ctggccatgg cactgttgtg | 2450 |
| atgcaggtga aagtgtcaaa aggagccccc tgcaggattc cagtgatagt | 2500 |
| agctgatgat cttacagcgg caatcaataa aggcattttg gttacagtta | 2550 |
| accccatcgc ctcaaccaat gatgatgaag tgctgattga ggtgaaccca | 2600 |
| ccttttggag acagctacat tatcgttggg agaggagatt cacgtctcac | 2650 |
| ttaccagtgg cacaaagagg gaagctcaat aggaaagttg ttcactcaga | 2700 |
| ccatgaaagg cgtggaacgc ctggccgtca tgggagacac cgcctgggat | 2750 |
| ttcagctccg ctggagggtt cttcacttcg gttgggaaag gaattcatac | 2800 |
| ggtgtttggc tctgcctttc aggggctatt ggcggcttg aactggataa | 2850 |
| caaaggtcat catgggggcg gtacttatat gggttggcat caacacaaga | 2900 |
| aacatgacaa tgtccatgag catgatcttg gtaggagtga tcatgatgtt | 2950 |
| tttgtctcta ggagttgggg cggatcaagg atgcgccatc aactttggca | 3000 |
| agagagagct caagtgcgga gatggtatct tcatatttag agactctgat | 3050 |
| gactggctga acaagtactc atactatcca gaagatcctg tgaagcttgc | 3100 |
| atcaatagtg aaagcctctt ttgaagaagg gaagtgtggc ctaaattcag | 3150 |
| ttgactccct tgagcatgag atgtggaaa gcagggcaga tgagatcaat | 3200 |
| gccattttg aggaaaacga ggtggacatt tctgttgtcg tgcaggatcc | 3250 |
| aaagaatgtt taccagagag gaactcatcc attttccaga attcgggatg | 3300 |
| gtctgcagta tggttggaag acttgggggta agaaccttgt gttctcccca | 3350 |
| gggaggaaga atggaagctt catcatagat ggaaagtcca ggaaagaatg | 3400 |
| cccgttttca aaccgggtct ggaattcttt ccagatagag gagtttggga | 3450 |
| cgggagtgtt caccacacgc gtgtacatgg acgcagtctt tgaatacacc | 3500 |
| atagactgcg atgatctat cttgggtgca gcggtgaacg gaaaaagag | 3550 |
| tgcccatggc tctccaacat tttggatggg aagtcatgaa gtaaatggga | 3600 |
| catgatgat ccacaccttg gaggcattag attacaagga gtgtgagtgg | 3650 |
| ccactgacac atacgattgg aacatcagtt gaagagagtg aaatgttcat | 3700 |
| gccgagatca atcggaggcc cagttagctc tcacaatcat atccctggat | 3750 |
| acaaggttca gacgaacgga ccttggatgc aggtaccact agaagtgaag | 3800 |
| agagaagctt gccagggac tagcgtgatc attgatggca actgtgatgg | 3850 |
| acgggaaaa tcaaccagat ccaccacgga tagcgggaaa gttattcctg | 3900 |
| aatggtgttg ccgctcctgc acaatgccgc ctgtgagctt ccatggtagt | 3950 |
| gatgggtgtt ggtatcccat ggaaattagg ccaaggaaaa cgcatgaaag | 4000 |
| ccatctggtg cgctcctggg ttacagctgg agaaatacat gctgtcccctt | 4050 |
| ttggtttggt gagcatgatg atagcaatgg aagtggtcct aaggaaaaga | 4100 |

| | |
|---|---|
| cagggaccaa agcaaatgtt ggttggagga gtagtgctct tgggagcaat | 4150 |
| gctggtcggg caagtaactc tccttgattt gctgaaactc acagtggctg | 4200 |
| tgggattgca tttccatgag atgaacaatg gaggagacgc catgtatatg | 4250 |
| gcgttgattg ctgccttttc aatcagacca gggctgctca tcggctttgg | 4300 |
| gctcaggacc ctatggagcc ctcgggaacg ccttgtgctg accctaggag | 4350 |
| cagccatggt ggagattgcc ttgggtggcg tgatgggcgg cctgtggaag | 4400 |
| tatctaaatg cagtttctct ctgcatcctg acaataaatg ctgttgcttc | 4450 |
| taggaaagca tcaaatacca tcttgcccct catggctctg ttgacacctg | 4500 |
| tcactatggc tgaggtgaga cttgccgcaa tgttcttttg tgccgtggtt | 4550 |
| atcatagggg tccttcacca gaatttcaag gacacctcca tgcagaagac | 4600 |
| tatacctctg gtggccctca cactcacatc ttacctgggc ttgacacaac | 4650 |
| cttttttggg cctgtgtgca tttctggcaa cccgcatatt tgggcgaagg | 4700 |
| agtatcccag tgaatgaggc actcgcagca gctggtctag tgggagtgct | 4750 |
| ggcaggactg gcttttcagg agatggagaa cttccttggt ccgattgcag | 4800 |
| ttggaggact cctgatgatg ctggttagcg tggctggag ggtggatggg | 4850 |
| ctagagctca agaagcttgg tgaagtttca tgggaagagg aggcggagat | 4900 |
| cagcgggagt tccgcccgct atgatgtggc actcagtgaa caaggggagt | 4950 |
| tcaagctgct ttctgaagag aaagtgccat gggaccaggt tgtgatgacc | 5000 |
| tcgctggcct tggttggggc tgccctccat ccatttgctc ttctgctggt | 5050 |
| ccttgctggg tggctgtttc atgtcagggg agctaggaga agtggggatg | 5100 |
| tcttgtggga tattcccact cctaagatca tcgaggaatg tgaacatctg | 5150 |
| gaggatggga tttatggcat attccagtca accttcttgg gggcctccca | 5200 |
| gcgaggagtg ggagtggcac agggaggggt gttccacaca atgtggcatg | 5250 |
| tcacaagagg agcttttcctt gtcaggaatg gcaagaagtt gattccatct | 5300 |
| tgggcttcag taaaggaaga ccttgtcgcc tatggtggct catggaagtt | 5350 |
| ggaaggcaga tgggatggag aggaagaggt ccagttgatc gcggctgttc | 5400 |
| caggaaagaa cgtggtcaac gtccagacaa aaccgagctt gttcaaagtg | 5450 |
| aggaatgggg gagaaatcgg ggctgtcgct cttgactatc cgagtggcac | 5500 |
| ttcaggatct cctattgtta acaggaacgg agaggtgatt gggctgtacg | 5550 |
| gcaatggcat ccttgtcggt gacaactcct tcgtgtccgc catatcccag | 5600 |
| actgaggtga aggaagaagg aaaggaggag ctccaagaga tcccgacaat | 5650 |
| gctaaagaaa ggaatgacaa ctgtccttga ttttcatcct ggagctggga | 5700 |
| agacaagacg tttcctccca cagatcttgg ccgagtgcgc acggagacgc | 5750 |
| ttgcgcactc ttgtgttggc ccccaccagg gttgttcttt ctgaaatgaa | 5800 |
| ggaggctttt cacggcctgg acgtgaaatt ccacacacag ctttttccg | 5850 |
| ctcacggcag cgggagagaa gtcattgatg ccatgtgcca tgccacccta | 5900 |
| acttacagga tgttggaacc aactagggtt gttaactggg aagtgatcat | 5950 |
| tatggatgaa gcccattttt tggatccagc tagcatagcc gctagaggtt | 6000 |
| gggcagcgca cagagctagg gcaaatgaaa gtgcaacaat cttgatgaca | 6050 |
| gccacaccgc ctgggactag tgatgaattt ccacattcaa atggtgaaat | 6100 |

```
agaagatgtt caaacggaca tacccagtga gccctggaac acagggcatg    6150
actggatcct agctgacaaa aggcccacgg catggttcct tccatccatc    6200
agagctgcaa atgtcatggc tgcctctttg cgtaaggctg aaagagtgt     6250
ggtggtcctg aacaggaaaa cctttgagag agaatacccc acgataaagc    6300
agaagaaacc tgactttata ttggccactg acatagctga atgggagcc     6350
aacctttgcg tggagcgagt gctggattgc aggacggctt ttaagcctgt    6400
gcttgtggat gaagggagga aggtggcaat aaaagggcca cttcgtatct    6450
ccgcatcctc tgctgctcaa aggagggggc gcattgggag aaatcccaac    6500
agagatggag actcatacta ctattctgag cctacaagtg aaaataatgc    6550
ccaccacgtc tgctggttgg aggcctcaat gctcttggac aacatggagg    6600
tgaggggtgg aatggtcgcc ccactctatg gcgttgaagg aactaaaaca    6650
ccagtttccc ctggtgaaat gagactgagg gatgaccaga ggaaagtctt    6700
cagagaacta gtgaggaatt gtgacctgcc cgtttggctt tcgtggcaag    6750
tggccaaggc tggtttgaag acgaatgatc gtaagtggtg ttttgaaggc    6800
cctgaggaac atgagatctt gaatgacagc ggtgaaacag tgaagtgcag    6850
ggctcctgga ggagcaaaga agcctctgcg cccaaggtgg tgtgatgaaa    6900
gggtgtcatc tgaccagagt gcgctgtctg aatttattaa gtttgctgaa    6950
ggtaggaggg gagctgctga agtgctagtt gtgctgagtg aactccctga    7000
tttcctggct aaaaaaggtg gagaggcaat ggataccatc agtgtgttcc    7050
tccactctga ggaaggctct agggcttacc gcaatgcact atcaatgatg    7100
cctgaggcaa tgacaatagt catgctgttt atactggctg gactactgac    7150
atcgggaatg gtcatctttt tcatgtctcc caaaggcatc agtagaatgt    7200
ctatggcgat gggcacaatg gccggctgtg gatatctcat gttccttgga    7250
ggcgtcaaac ccactcacat ctcctatgtc atgctcatat tctttgtcct    7300
gatggtggtt gtgatccccg agccagggca acaaaggtcc atccaagaca    7350
accaagtggc atacctcatt attggcatcc tgacgctggt ttcagcggtg    7400
gcagccaacg agctaggcat gctggagaaa accaaagagg acctctttgg    7450
gaagaagaac ttaattccat ctagtgcttc accctggagt tggccggatc    7500
ttgacctgaa gccaggagct gcctggacag tgtacgttgg cattgttaca    7550
atgctctctc caatgttgca ccactggatc aaagtcgaat atggcaacct    7600
gtctctgtct ggaatagccc agtcagcctc agtcctttct ttcatggaca    7650
aggggatacc attcatgaag atgaatatct cggtcataat gctgctggtc    7700
agtggctgga attcaataac agtgatgcct ctgctctgtg gcataggggtg   7750
cgccatgctc cactggtctc tcattttacc tggaatcaaa gcgcagcagt    7800
caaagcttgc acagagaagg gtgttccatg gcgttgccga gaaccctgtg    7850
gttgatggga atccaacagt tgacattgag gaagctcctg aaatgcctgc    7900
cctttatgaa aagaaactgg ctctatatct ccttcttgct ctcagcctag    7950
cttctgttgc catgtgcaga acgccctttt cattggctga aggcattgtc    8000
ctagcatcag ctgccttagg gccgctcata gagggaaaca ccagccttct    8050
ttggaatgga cccatggctg tctccatgac aggagtcatg agggggaatc    8100
```

| | |
|---|---|
| actatgcttt tgtgggagtc atgtacaatc tatggaagat gaaaactgga | 8150 |
| cgccggggga gcgcgaatgg aaaaactttg ggtgaagtct ggaagaggga | 8200 |
| actgaatctg ttggacaagc gacagtttga gttgtataaa aggaccgaca | 8250 |
| ttgtggaggt ggatcgtgat acggcacgca ggcatttggc cgaagggaag | 8300 |
| gtggacaccg gggtggcggt ctccagggg accgcaaagt taaggtggtt | 8350 |
| ccatgagcgt ggctatgtca agctggaagg tagggtgatt gacctggggt | 8400 |
| gtggccgcgg aggctggtgt tactacgctg ctgcgcaaaa ggaagtgagt | 8450 |
| ggggtcaaag gatttactct tggaagagac ggccatgaga aacccatgaa | 8500 |
| tgtgcaaagt ctgggatgga acatcatcac cttcaaggac aaaactgata | 8550 |
| tccaccgcct agaaccagtg aaatgtgaca ccctttgtg tgacattgga | 8600 |
| gagtcatcat cgtcatcggt cacagagggg gaaaggaccg tgagagttct | 8650 |
| tgatactgta gaaaaatggc tggcttgtgg ggttgacaac ttctgtgtga | 8700 |
| aggtgttagc tccatacatg ccagatgttc ttgagaaact ggaattgctc | 8750 |
| caaaggaggt ttggcggaac agtgatcagg aaccctctct ccaggaattc | 8800 |
| cactcatgaa atgtactacg tgtctggagc ccgcagcaat gtcacattta | 8850 |
| ctgtgaacca acatcccgc ctcctgatga ggagaatgag gcgtccaact | 8900 |
| ggaaaagtga ccctggaggc tgacgtcatc ctcccaattg ggacacgcag | 8950 |
| tgttgagaca gacaagggac ccctggacaa agaggccata aagaaagggg | 9000 |
| ttgagaggat aaaatctgag tacatgacct cttggtttta tgacaatgac | 9050 |
| aaccectaca ggacctggca ctactgtggc tcctatgtca caaaaacctc | 9100 |
| aggaagtgcg gcgagcatgg taaatggtgt tattaaaatt ctgacatatc | 9150 |
| catgggacag gatagaggag gtcacaagaa tggcaatgac tgacacaacc | 9200 |
| ccttttggac agcaaagagt gtttaaagaa aaagttgaca ccagagcaaa | 9250 |
| ggatccacca gcgggaacta ggaagatcat gaaagttgtc aacaggtggc | 9300 |
| tgttccgcca cctggccaga gaaaagaacc ccagactgtg cacaaaggaa | 9350 |
| gaatttattg caaagtccg aagtcatgca gccattggag cttacctgga | 9400 |
| agaacaagaa cagtggaaga ctgccaatga ggctgtccaa gacccaaagt | 9450 |
| tctgggaact ggtggatgaa gaaaggaagc tgcaccaaca aggcaggtgt | 9500 |
| cggacttgtg tgtacaacat gatggggaaa agagagaaga agctgtcaga | 9550 |
| gtttgggaaa gcaaagggaa gccgtgccat atggtatatg tggctgggag | 9600 |
| cgcggtatct tgagtttgag gccctgggat tcctgaatga ggaccattgg | 9650 |
| gcttccaggg aaaactcagg aggaggagtg gaaggcattg gcttacaata | 9700 |
| cctaggatat gtgatcagag acctggctgc aatggatggt ggtggattct | 9750 |
| acgcggatga caccgctgga tgggacacgc gcatcacaga ggcagacctt | 9800 |
| gatgatgaac aggagatctt gaactacatg agcccacatc acaaaaaact | 9850 |
| ggcacaagca gtgatggaaa tgacatacaa gaacaaagtg gtgaaagtgt | 9900 |
| tgagaccagc cccaggaggg aaagcctaca tggatgtcat aagtcgacga | 9950 |
| gaccagagag gatccgggca ggtagtgact tatgctctga acaccatcac | 10000 |
| caacttgaaa gtccaattga tcagaatggc agaagcagag atggtgatac | 10050 |
| atcaccaaca tgttcaagat tgtgatgaat cagttctgac caggctggag | 10100 |

| | |
|---|---|
| gcatggctca ctgagcacgg atgtgacaga ctgaagagga tggcggtgag | 10150 |
| tggagacgac tgtgtggtcc ggcccatcga tgacaggttc ggcctggccc | 10200 |
| tgtcccatct caacgccatg tccaaggtta gaaaggacat atctgaatgg | 10250 |
| cagccatcaa aagggtggaa tgattgggag aatgtgccct tctgttccca | 10300 |
| ccacttccat gaactacagc tgaaggatgg caggaggatt gtggtgcctt | 10350 |
| gccgagaaca ggacgagctc attgggagag aaggggtgtc tccaggaaac | 10400 |
| ggctggatga tcaaggaaac agcttgcctc agcaaagcct atgccaacat | 10450 |
| gtggtcactg atgtattttc acaaaaggga catgaggcta ctgtcattgg | 10500 |
| ctgtttcctc agctgttccc acctcatggg ttccacaagg acgcacaaca | 10550 |
| tggtcgattc atgggaaagg ggagtggatg accacggaag acatgcttga | 10600 |
| ggtgtggaac agagtatgga taaccaacaa cccacacatg caggacaaga | 10650 |
| caatggtgaa aaaatggaga gatgtccctt atctaaccaa gagacaagac | 10700 |
| aagctgtgcg gatcactgat tggaatgacc aatagggcca cctgggcctc | 10750 |
| ccacatccat ttagtcatcc atcgtatccg aacgctgatt ggacaggaga | 10800 |
| aatacactga ctacctaaca gtcatggaca ggtattctgt ggatgctgac | 10850 |
| ctgcaactgg gtgagcttat ctgaaacacc atctaacagg aataaccggg | 10900 |
| atacaaacca cgggtggaga accggactcc ccacaacctg aaaccgggat | 10950 |
| ataaaccacg gctggagaac cggactccgc acttaaaatg aaacagaaac | 11000 |
| cgggataaaa actacggatg gagaaccgga ctccacacat tgagacagaa | 11050 |
| gaagttgtca gcccagaacc ccacacgagt tttgccactg ctaagctgtg | 11100 |
| aggcagtgca ggctgggaca gccgacctcc aggttgcgaa aaacctggtt | 11150 |
| tctgggacct cccaccccag agtaaaaaga acggagcctc cgctaccacc | 11200 |
| ctcccacgtg gtggtagaaa gacggggtct agaggttaga ggagaccctc | 11250 |
| cagggaacaa atagtgggac catattgacg ccagggaaag accggagtgg | 11300 |
| ttctctgctt ttcctccaga ggtctgtgag cacagtttgc tcaagaataa | 11350 |
| gcagaccttt ggatgacaaa cacaaaacca ctgggtcggc atggcatctc | 11400 |
| cacctcctcg cggtccgacc tgggcatccg aaggaggacg cacgtccact | 11450 |
| cggatggcta agggagagcc acgagctcct cgacagatca taatcagcca | 11500 |
| taccacattt gtagaggttt tacttgcttt aaaaaacctc ccacacctcc | 11550 |
| ccctgaacct gaaacataaa atgaatgcaa ttgttgttgt taacttgttt | 11600 |
| attgcagctt ataatggtta caaataaagc aatagcatca caaatttcac | 11650 |
| aaataaagca ttttttttcac tgcattctag ttgtggtttg tccaaactca | 11700 |
| tcaagatctc gagcaagacg tttcccgttg aatatggctc ataacacccc | 11750 |
| ttgtattact gtttatgtaa gcagacagtt ttattgttca tgatgatata | 11800 |
| tttttatctt gtgcaatgta acatcagaga ttttgagaca caacgtggct | 11850 |
| ttgttgaata aatcgaactt tgctgagtt gaaggatcag atcacgcatc | 11900 |
| ttcccgacaa cgcagaccgt tccgtggcaa agcaaaagtt caaaatcacc | 11950 |
| aactggtcca cctacaacaa agctctcatc aaccgtggct ccctcacttt | 12000 |
| ctggctggat gatggggcga ttcaggcctg gtatgagtca gcaacacctt | 12050 |
| cttcacgagg cagacctcag cgctagcgga gtgtatactg gcttactatg | 12100 |

```
ttggcactga tgagggtgtc agtgaagtgc ttcatgtggc aggagaaaaa    12150
aggctgcacc ggtgcgtcag cagaatatgt gatacaggta atattccgct    12200
tcctcgctca ctgactcgct acgctcggtc gttcgactgc ggcgagcgga    12250
aatggcttac gaacggggcg gagatttcct ggaagatgcc aggaagatac    12300
ttaacaggga agtgagaggg ccgcggcaaa gccgttttc cataggctcc     12350
gcccccctga caagcatcac gaaatctgac gctcaaatca gtggtggcga    12400
aacccgacag gactataaag ataccaggcg tttccctgg cggctccctc     12450
gtgcgctctc ctgttcctgc ctttcggttt accggtgtca ttccgctgtt    12500
atggccgcgt ttgtctcatt ccacgcctga cactcagttc cgggtaggca    12550
gttcgctcca agctggactg tatgcacgaa ccccccgttc agtccgaccg    12600
ctgcgcctta ccggtaact atcgtcttga gtccaacccg gaaagacatg      12650
caaaagcacc actggcagca gccactggta attgatttag aggagttagt    12700
cttgaagtca tgcgccggtt aaggctaaac tgaaaggaca gttttggtg     12750
actgcgctcc tccaagccag ttacctcggt tcaaagagtt ggtagctcag    12800
agaaccttcg aaaaaccgcc ctgcaaggcg gttttttcgt tttcagagca    12850
agagattacg cgcagaccaa aacgatctca agaagatcat cttattaagg    12900
ggtctgacgc tcagtggaac gaaaactcac gttaagggat tttggtcatg    12950
agattatcaa aaaggatctt cacctagatc cttttaaatt aaaaatgaag    13000
ttttaaatca atctaaagta tatatgagta aacttggtct gacagttacc    13050
aatgcttaat cagtgaggca cctatctcag cgatctgtct atttcgttca    13100
tccatagttg cctgactccc cgtcgtgtag ataactacga tacgggaggg    13150
cttaccatct ggccccagtg ctgcaatgat accgcgagac ccacgctcac    13200
cggctccaga tttatcagca ataaaccagc cagccggaag ggccgagcgc    13250
agaagtggtc ctgcaacttt atccgcctcc atccagtcta ttaattgttg    13300
ccgggaagct agagtaagta gttcgccagt taatagtttg cgcaacgttg    13350
ttgccattgc tgcaggcatc gtggtgtcac gctcgtcgtt tggtatggct    13400
tcattcagct ccggttccca acgatcaagg cgagttacat gatcccccat    13450
gttgtgcaaa aaagcggtta gctccttcgg tcctccgatc gttgtcagaa    13500
gtaagttggc cgcagtgtta tcactcatgg ttatggcagc actgcataat    13550
tctcttactg tcatgccatc cgtaagatgc ttttctgtga ctggtgagta    13600
ctcaaccaag tcattctgag aatagtgtat gcggcgaccg agttgctctt    13650
gcccggcgtc aacacgggat aataccgcgc cacatagcag aactttaaaa    13700
gtgctcatca ttggaaaacg ttcttcgggg cgaaaactct caaggatctt    13750
accgctgttg agatccagtt cgatgtaacc cactcgtgca cccaactgat    13800
cttcagcatc ttttactttc accagcgttt ctgggtgagc aaaaacagga    13850
aggcaaaatg ccgcaaaaaa gggaataagg gcgacacgga aatgttgaat    13900
actcatactc ttcctttttc aatattattg aagcatttat cagggttatt    13950
gtctcatgag cggatacata tttgaatgta tttagaaaaa taaacaaata    14000
ggggttccgc gcacatttcc ccgaaaagtg ccacctgacg tgtcgacgcg    14050
gccgctagcg atgaccctgc tgattggttc gctgaccatt tccgggtgcg    14100
```

-continued

| | |
|---|---|
| ggacggcgtt accagaaact cagaaggttc gtccaaccaa accgactctg | 14150 |
| acggcagttt acgagagaga tgatagggtc tgcttcagta agccagatgc | 14200 |
| tacacaatta ggcttgtaca tattgtcgtt agaacgcggc tacaattaat | 14250 |
| acataacctt atgtatcata cacatacgat ttaggtgaca ctata | 14295 |

<210> SEQ ID NO 7
<211> LENGTH: 10863
<212> TYPE: DNA
<213> ORGANISM: artificial sequence
<220> FEATURE:
<223> OTHER INFORMATION: sequence of VEErep/C1/Pac plasmid

<400> SEQUENCE: 7

| | |
|---|---|
| gatgggcggc gcatgagaga agcccagacc aattacctac ccaaaatgga | 50 |
| gaaagttcac gttgacatcg aggaagacag cccattcctc agagctttgc | 100 |
| agcggagctt cccgcagttt gaggtagaag ccaagcaggt cactgataat | 150 |
| gaccatgcta atgccagagc gttttcgcat ctggcttcaa aactgatcga | 200 |
| aacggaggtg gacccatccg acacgatcct tgacattgga agtgcgcccg | 250 |
| cccgcagaat gtattctaag cacaagtatc attgtatctg tccgatgaga | 300 |
| tgtgcggaag atccggacag attgtataag tatgcaacta agctgaagaa | 350 |
| aaactgtaag gaaataactg ataaggaatt ggacaagaaa atgaaggagc | 400 |
| tggccgccgt catgagcgac cctgacctgg aaactgagac tatgtgcctc | 450 |
| cacgacgacg agtcgtgtcg ctacgaaggg caagtcgctg tttaccagga | 500 |
| tgtatacgcg gttgacggac cgacaagtct ctatcaccaa gccaataagg | 550 |
| gagttagagt cgcctactgg ataggctttg acaccacccc ttttatgttt | 600 |
| aagaacttgg ctggagcata tccatcatac tctaccaact gggccgacga | 650 |
| aaccgtgtta acggctcgta acataggcct atgcagctct gacgttatgg | 700 |
| agcggtcacg tagagggatg tccattctta gaaagaagta tttgaaacca | 750 |
| tccaacaatg ttctattctc tgttggctcg accatctacc acgagaagag | 800 |
| ggacttactg aggagctggc acctgccgtc tgtatttcac ttacgtggca | 850 |
| agcaaaatta cacatgtcgg tgtgagacta tagttagttg cgacgggtac | 900 |
| gtcgttaaaa gaatagctat cagtccaggc ctgtatggga agccttcagg | 950 |
| ctatgctgct acgatgcacc gcgagggatt cttgtgctgc aaagtgacag | 1000 |
| acacattgaa cggggagagg gtctcttttc ccgtgtgcac gtatgtgcca | 1050 |
| gctacattgt gtgaccaaat gactggcata ctggcaacag atgtcagtgc | 1100 |
| ggacgacgcg caaaaactgc tggttgggct caaccagcgt atagtcgtca | 1150 |
| acggtcgcac ccagagaaac accaatacca tgaaaaatta cctttttgccc | 1200 |
| gtagtggccc aggcatttgc taggtgggca aggaatatata aggaagatca | 1250 |
| agaagatgaa aggccactag gactacgaga tagacagtta gtcatgggt | 1300 |
| gttgttgggc ttttagaagg cacaagataa catctatttta taagcgcccg | 1350 |
| gatacccaaa ccatcatcaa agtgaacagc gatttccact cattcgtgct | 1400 |
| gcccaggata ggcagtaaca cattggagat cgggctgaga acaagaatca | 1450 |
| ggaaaatgtt agaggagcac aaggagccgt cacctctcat taccgccgag | 1500 |
| gacgtacaag aagctaagtg cgcagccgat gaggctaagg aggtgcgtga | 1550 |

| | |
|---|---|
| agccgaggag ttgcgcgcag ctctaccacc tttggcagct gatgttgagg | 1600 |
| agcccactct ggaagccgat gtcgacttga tgttacaaga ggctgggcc | 1650 |
| ggctcagtgg agacacctcg tggcttgata aaggttacca gctacgatgg | 1700 |
| cgaggacaag atcggctctt acgctgtgct ttctccgcag gctgtactca | 1750 |
| agagtgaaaa attatcttgc atccaccctc tcgctgaaca agtcatagtg | 1800 |
| ataacacact ctggccgaaa agggcgttat gccgtggaac cataccatgg | 1850 |
| taaagtagtg gtgccagagg gacatgcaat acccgtccag gactttcaag | 1900 |
| ctctgagtga aagtgccacc attgtgtaca acgaacgtga gttcgtaaac | 1950 |
| aggtacctgc accatattgc cacacatgga ggagcgctga acactgatga | 2000 |
| agaatattac aaaactgtca gcccagcga gcacgacggc gaatacctgt | 2050 |
| acgacatcga caggaaacag tgcgtcaaga agaactagt cactgggcta | 2100 |
| gggctcacag gcgagctggt ggatcctccc ttccatgaat tcgcctacga | 2150 |
| gagtctgaga acacgaccag ccgctcctta ccaagtacca accatagggg | 2200 |
| tgtatggcgt gccaggatca ggcaagtctg gcatcattaa aagcgcagtc | 2250 |
| accaaaaaag atctagtggt gagcgccaag aaagaaaact gtgcagaaat | 2300 |
| tataagggac gtcaagaaaa tgaaagggct ggacgtcaat gccagaactg | 2350 |
| tggactcagt gctcttgaat ggatgcaaac accccgtaga gaccctgtat | 2400 |
| attgacgaag cttttgcttg tcatgcaggt actctcagag cgctcatagc | 2450 |
| cattataaga cctaaaaagg cagtgctctg cggggatccc aaacagtgcg | 2500 |
| gtttttttaa catgatgtgc ctgaaagtgc attttaacca cgagatttgc | 2550 |
| acacaagtct tccacaaaag catctctcgc cgttgcacta aatctgtgac | 2600 |
| ttcggtcgtc tcaaccttgt tttacgacaa aaaaatgaga acgacgaatc | 2650 |
| cgaaagagac taagattgtg attgacacta ccggcagtac caaacctaag | 2700 |
| caggacgatc tcattctcac ttgtttcaga gggtgggtga agcagttgca | 2750 |
| aatagattac aaaggcaacg aaataatgac ggcagctgcc tctcaagggc | 2800 |
| tgacccgtaa aggtgtgtat gccgttcggt acaaggtgaa tgaaaatcct | 2850 |
| ctgtacgcac ccacctcaga acatgtgaac gtcctactga cccgcacgga | 2900 |
| ggaccgcatc gtgtggaaaa cactagccgg cgacccatgg ataaaaacac | 2950 |
| tgactgccaa gtaccctggg aatttcactg ccacgataga ggagtggcaa | 3000 |
| gcagagcatg atgccatcat gaggcacatc ttggagagac cggaccctac | 3050 |
| cgacgtcttc cagaataagg caaacgtgtg ttgggccaag gctttagtgc | 3100 |
| cggtgctgaa gaccgctggc atagacatga ccactgaaca atggaacact | 3150 |
| gtggattatt ttgaaacgga caaagctcac tcagcagaga tagtattgaa | 3200 |
| ccaactatgc gtgaggttct ttggactcga tctggactcc ggtctatttt | 3250 |
| ctgcacccac tgttccgtta tccattagga ataatcactg gataactcc | 3300 |
| ccgtcgccta acatgtacgg gctgaataaa gaagtggtcc gtcagctctc | 3350 |
| tcgcaggtac ccacaactgc ctcgggcagt tgccactgga agagtctatg | 3400 |
| acatgaacac tggtacactg cgcaattatg atccgcgcat aaacctagta | 3450 |
| cctgtaaaca gaagactgcc tcatgcttta gtcctccacc ataatgaaca | 3500 |
| cccacagagt gactttttctt cattcgtcag caaattgaag ggcagaactg | 3550 |

```
tcctggtggt cggggaaaag ttgtccgtcc caggcaaaat ggttgactgg      3600
ttgtcagacc ggcctgaggc taccttcaga gctcggctgg atttaggcat      3650
cccaggtgat gtgcccaaat atgacataat atttgttaat gtgaggaccc      3700
catataaata ccatcactat cagcagtgtg aagaccatgc cattaagctt      3750
agcatgttga ccaagaaagc ttgtctgcat ctgaatcccg gcggaacctg      3800
tgtcagcata ggttatggtt acgctgacag ggccagcgaa agcatcattg      3850
gtgctatagc gcggcagttc aagttttccc gggtatgcaa accgaaatcc      3900
tcacttgaag agacggaagt tctgtttgta ttcattgggt acgatcgcaa      3950
ggcccgtacg cacaatcctt acaagctttc atcaaccttg accaacattt      4000
atacaggttc cagactccac gaagccggat gtgcaccctc atatcatgtg      4050
gtgcgagggg atattgccac ggccaccgaa ggagtgatta taaatgctgc      4100
taacagcaaa ggacaacctg gcggaggggt gtgcggagcg ctgtataaga      4150
aattcccgga aagcttcgat ttacagccga tcgaagtagg aaaagcgcga      4200
ctggtcaaag gtgcagctaa acatatcatt catgccgtag gaccaaactt      4250
caacaaagtt tcggaggttg aaggtgacaa acagttggca gaggcttatg      4300
agtccgctaa gattgtcaac gataacaatt acaagtcagt agcgattcca      4350 cttttgtccac cggcatcttt tccgggaaca agatcgact aacccaatca      4400 ttgaaccatt tgctgacagc tttagacacc actgatgcag atgtagccat      4450
atactgcagg gacaagaaat gggaatgact ctcaaggaag cagtggctag      4500
gagagaagca gtggaggaga tatgcatatc cgacgactct tcagtgacag      4550
aacctgatgc agagctggtg agggtgcatc cgaagagttc tttggctgga      4600
aggaagggct acagcacaag cgatggcaaa actttctcat atttggaagg      4650
gaccaagttt caccaggcgg ccaaggatat agcagaaatt aatgccatgt      4700
ggcccgttgc aacggaggcc aatgagcagg tatgcatgta tatcctcgga      4750
gaaagcatga gcagtattag gtcgaaatgc cccgtcgaag agtcggaagc      4800
ctccacacca cctagcacgc tgccttgctt gtgcatccat gccatgactc      4850
cagaaagagt acagcgccta aaagcctcac gtccagaaca aattactgtg      4900
tgctcatcct ttccattgcc gaagtataga atcactggtg tgcagaagat      4950
ccaatgctcc cagcctatat tgttctcacc gaaagtgcct gcgtatattc      5000
atccaaggaa gtatctcgtg aaacaccac cggtagacga gactccggag      5050
ccatcggcag agaaccaatc cacagagggg acacctgaac aaccaccact      5100
tataaccgag gatgagacca ggactagaac gcctgagccg atcatcatcg      5150
aagaggaaga agaggatagc ataagtttgc tgtcagatgg cccgacccac      5200
caggtgctgc aagtcgaggc agacattcac gggccgccct ctgtatctag      5250
ctcatcctgg tccattcctc atgcatccga ctttgatgtg acagtttat      5300 ccatacttga caccctggag ggagctagcg tgaccagcgg ggcaacgtca      5350
gccgagacta actcttactt cgcaaagagt atggagtttc tggcgcgacc      5400
ggtgcctgcg cctcgaacag tattcaggaa ccctccacat cccgctccgc      5450
gcacaagaac accgtcactt gcacccagca gggcctgctc gagaaccagc      5500
ctagtttcca ccccgccagg cgtgaatagg gtgatcacta gagaggagct      5550
```

```
cgaggcgctt accccgtcac gcactcctag caggtcggtc tcgagaacca      5600
gcctggtctc caacccgcca ggcgtaaata gggtgattac aagagaggag      5650
tttgaggcgt tcgtagcaca acaacaatga cggtttgatg cgggtgcata      5700
catcttttcc tccgacaccg gtcaagggca tttacaacaa aaatcagtaa      5750
ggcaaacggt gctatccgaa gtggtgttgg agaggaccga attggagatt      5800
tcgtatgccc cgcgcctcga ccaagaaaaa gaagaattac tacgcaagaa      5850
attacagtta aatcccacac ctgctaacag aagcagatac cagtccagga      5900
aggtggagaa catgaaagcc ataacagcta gacgtattct gcaaggccta      5950
gggcattatt tgaaggcaga aggaaaagtg gagtgctacc gaaccctgca      6000
tcctgttcct ttgtattcat ctagtgtgaa ccgtgccttt tcaagcccca      6050
aggtcgcagt ggaagcctgt aacgccatgt tgaaagagaa ctttccgact      6100
gtggcttctt actgtattat tccagagtac gatgcctatt tggacatggt      6150
tgacggagct tcatgctgct tagacactgc cagttttgc cctgcaaagc       6200
tgcgcagctt tccaaagaaa cactcctatt tggaacccac aatacgatcg      6250
gcagtgcctt cagcgatcca gaacacgctc cagaacgtcc tggcagctgc      6300
cacaaaaaga aattgcaatg tcacgcaaat gagagaattg cccgtattgg      6350
attcggcggc ctttaatgtg gaatgcttca agaaatatgc gtgtaataat      6400
gaatattggg aaacgtttaa agaaaacccc atcaggctta ctgaagaaaa      6450
cgtggtaaat tacattacca aattaaaagg accaaaagct gctgctcttt      6500
ttgcgaagac acataatttg aatatgttgc aggacatacc aatggacagg      6550
tttgtaatgg acttaaagag agacgtgaaa gtgactccag gaacaaaaca      6600
tactgaagaa cggcccaagg tacaggtgat ccaggctgcc gatccgctag      6650
caacagcgta tctgtgcgga atccaccgag agctggttag gagattaaat      6700
gcggtcctgc ttccgaacat tcatacactg tttgatatgt cggctgaaga      6750
cttttgacgct attatagccg agcacttcca gcctggggat tgtgttctgg      6800
aaactgacat cgcgtcgttt gataaaagtg aggacgacgc catggctctg      6850
accgcgttaa tgattctgga agacttaggt gtggacgcag agctgttgac      6900
gctgattgag gcggctttcg gcgaaatttc atcaatacat ttgcccacta      6950
aaactaaatt taaattcgga gccatgatga aatctggaat gttcctcaca      7000
ctgtttgtga acacagtcat taacattgta atcgcaagca gagtgttgag      7050
agaacgcgcta accggatcac catgtgcagc attcattgga gatgacaata      7100
tcgtgaaagg agtcaaatcg gacaaattaa tggcagacag gtgcgccacc      7150
tggttgaata tggaagtcaa gattatagat gctgtggtgg gcgagaaagc      7200
gccttatttc tgtggagggt ttattttgtg tgactccgtg accggcacag      7250
cgtgccgtgt ggcagacccc ctaaaaaggc tgtttaagct tggcaaacct      7300
ctggcagcag acgatgaaca tgatgatgac aggagaaggg cattgcatga      7350
agagtcaaca cgctggaacc gagtgggtat tctttcagag ctgtgcaagg      7400
cagtagaatc aaggtatgaa accgtaggaa cttccatcat agttatggcc      7450
atgactactc tagctagcag tgttaaatca ttcagctacc tgagaggggc      7500
ccctataact ctctacggct aacctgaatg gactacgaca tagtctagtc      7550
```

```
cgccaagtct agaccatgtc tggtcgtaaa gctcagggaa aaaccctggg      7600
cgtcaatatg gtacgacgag gagttcgctc cttgtcaaac aaaataaaac      7650
aaaaaacaaa acaaattgga aacagacctg gaccttcaag aggtgttcaa      7700
ggatttatct ttttcttttt gttcaacatt ttgactggaa aaaagatcac      7750
agcccaccta agaggttgt ggaaaatgct ggacccaaga caaggcttgg       7800
ctgttctaag gaaagtcaag agagtggtgg ccagtttgat gagaggattg      7850
tcctcaagga aacgccgttc ccatgatgtt ctgactgtgc aattcctaat      7900
tttgggaatg ctgttgatga cgggtggata agggcccta taactctcta       7950 cggctaacct gaatggacta cgacatagtc tagtccgcca agtctagagc      8000
ttaccatgac cgagtacaag cccacggtgc gcctcgccac ccgcgacgac      8050
gtccccaggg ccgtacgcac cctcgccgcc gcgttcgccg actaccccgc      8100
cacgcgccac accgtcgatc cggaccgcca catcgagcgg gtcaccgagc      8150
tgcaagaact cttcctcacg cgcgtcgggc tcgacatcgg caaggtgtgg      8200
gtcgcggacg acgcgccgc ggtggcggtc tggaccacgc cggagagcgt       8250
cgaagcgggg gcggtgttcg ccgagatcgg cccgcgcatg gccgagttga      8300
gcggttcccg gctggccgcg cagcaacaga tggaaggcct cctggcgccg      8350
caccggccca aggagcccgc gtggttcctg gccaccgtcg gcgtctcgcc      8400
cgaccaccag gcaagggtc tgggcagcgc cgtcgtgctc cccggagtgg       8450
aggcggccga gcgcgccggg gtgcccgcct tcctggagac ctccgcgccc      8500
cgcaacctcc ccttctacga gcggctcggc ttcaccgtca ccgccgacgt      8550
cgagtgcccg aaggaccgcg cgacctggtg catgacccgc aagcccggtg      8600
cctgacgccc gccccacgac ccgcagcgcc cgaccgaaag gagcgcacga      8650
ccccatgatc gctagaccat ggggtaccga gtatgttacg tgcaaaggtg      8700
attgtcaccc cccgaaagac catattgtga cacaccctca gtatcacgcc      8750
caaacattta cagccgcggt gtcaaaaacc gcgtggacgt ggttaacatc      8800
cctgctggga ggatcagccg taattattat aattggcttg gtgctggcta      8850
ctattgtggc catgtacgtg ctgaccaacc agaaacataa ttgaatacag      8900
cagcaattgg caagctgctt acatagaact cgcggcgatt ggcatgccgc      8950
cttaaaattt ttatttatt ttttcttttc ttttccgaat cggattttgt       9000
ttttaatatt tcaaaaaaaa aaaaaaaaa aaaaaacgc gtcgagggga       9050 attaattctt gaagacgaaa gggccaggtg gcacttttcg gggaaatgtg      9100
cgcggaaccc ctatttgttt attttttctaa atacattcaa atatgtatcc     9150
gctcatgaga caataaccct gataaatgct tcaataatat tgaaaaagga      9200
agagtatgag tattcaacat ttccgtgtcg cccttattcc cttttttgcg     9250
gcattttgcc ttcctgtttt tgctcaccca gaaacgctgg tgaaagtaaa     9300
agatgctgaa gatcagttgg gtgcacgagt gggttacatc gaactggatc     9350
tcaacagcgg taagatcctt gagagttttc gccccgaaga cgttttcca     9400 atgatgagca cttttaaagt tctgctatgt ggcgcggtat tatcccgtgt     9450
tgacgccggg caagagcaac tcggtcgccg catacactat tctcagaatg     9500
acttggttga gtactcacca gtcacagaaa agcatcttac ggatggcatg     9550
```
acagtaagag aattatgcag tgctgccata accatgagtg ataacactgc 9600
ggccaactta cttctgacaa cgatcggagg accgaaggag ctaaccgctt 9650
ttttgcacaa catgggggat catgtaactc gccttgatcg ttgggaaccg 9700
gagctgaatg aagccatacc aaacgacgag cgtgacacca cgatgcctgt 9750
agcaatggca acaacgttgc gcaaactatt aactggcgaa ctacttactc 9800
tagcttcccg gcaacaatta atagactgga tggaggcgga taaagttgca 9850
ggaccacttc tgcgctcggc ccttccggct ggctggttta ttgctgataa 9900
atctggagcc ggtgagcgtg ggtctcgcgg tatcattgca gcactggggc 9950
cagatggtaa gccctcccgt atcgtagtta tctacacgac ggggagtcag 10000
gcaactatgg atgaacgaaa tagacagatc gctgagatag gtgcctcact 10050
gattaagcat tggtaactgt cagaccaagt ttactcatat atactttaga 10100
ttgatttaaa acttcatttt taatttaaaa ggatctaggt gaagatcctt 10150
tttgataatc tcatgaccaa aatcccttaa cgtgagtttt cgttccactg 10200
agcgtcagac cccgtagaaa agatcaaagg atcttcttga gatccttttt 10250
ttctgcgcgt aatctgctgc ttgcaaacaa aaaaaccacc gctaccagcg 10300
gtggtttgtt tgccggatca agagctacca actctttttc cgaaggtaac 10350
tggcttcagc agagcgcaga taccaaatac tgtccttcta gtgtagccgt 10400
agttaggcca ccacttcaag aactctgtag caccgcctac atacctcgct 10450
ctgctaatcc tgttaccagt ggctgctgcc agtggcgata agtcgtgtct 10500
taccgggttg gactcaagac gatagttacc ggataaggcg cagcggtcgg 10550
gctgaacggg gggttcgtgc acacagccca gcttggagcg aacgacctac 10600
accgaactga gatacctaca gcgtgagcat tgagaaagcg ccacgcttcc 10650
cgaagggaga aaggcggaca ggtatccggt aagcggcagg gtcggaacag 10700
gagagcgcac gagggagctt ccagggggaa acgcctggta tctttatagt 10750
cctgtcgggt ttcgccacct ctgacttgag cgtcgatttt tgtgatgctc 10800
gtcagggggg cggagcctat ggaaaaacgc cagcaacgcg agctcgattt 10850
aggtgacact ata 10863

<210> SEQ ID NO 8
<211> LENGTH: 10796
<212> TYPE: DNA
<213> ORGANISM: artificial sequence
<220> FEATURE:
<223> OTHER INFORMATION: sequence of VEErep/C2/Pac plasmid

<400> SEQUENCE: 8
gatgggcggc gcatgagaga agcccagacc aattacctac ccaaaatgga 50
gaaagttcac gttgacatcg aggaagacag cccattcctc agagctttgc 100
agcggagctt cccgcagttt gaggtagaag ccaagcaggt cactgataat 150
gaccatgcta atgccagagc gttttcgcat ctggcttcaa aactgatcga 200
aacggaggtg gacccatccg acacgatcct tgacattgga agtgcgcccg 250
cccgcagaat gtattctaag cacaagtatc attgtatctg tccgatgaga 300
tgtgcggaag atccggacag attgtataag tatgcaacta agctgaagaa 350
aaactgtaag gaaataactg ataaggaatt ggacaagaaa atgaaggagc 400

```
tggccgccgt catgagcgac cctgacctgg aaactgagac tatgtgcctc        450
cacgacgacg agtcgtgtcg ctacgaaggg caagtcgctg tttaccagga        500
tgtatacgcg gttgacggac cgacaagtct ctatcaccaa gccaataagg        550
gagttagagt cgcctactgg ataggctttg acaccacccc ttttatgttt        600
aagaacttgg ctggagcata tccatcatac tctaccaact gggccgacga        650
aaccgtgtta acggctcgta acataggcct atgcagctct gacgttatgg        700
agcggtcacg tagagggatg tccattctta gaaagaagta tttgaaacca        750
tccaacaatg ttctattctc tgttggctcg accatctacc acgagaagag        800
ggacttactg aggagctggc acctgccgtc tgtatttcac ttacgtggca        850
agcaaaatta cacatgtcgg tgtgagacta tagttagttg cgacgggtac        900
gtcgttaaaa gaatagctat cagtccaggc ctgtatggga agccttcagg        950
ctatgctgct acgatgcacc gcgagggatt cttgtgctgc aaagtgacag       1000
acacattgaa cggggagagg gtctcttttc ccgtgtgcac gtatgtgcca       1050
gctacattgt gtgaccaaat gactggcata ctggcaacag atgtcagtgc       1100
ggacgacgcg caaaaactgc tggttgggct caaccagcgt atagtcgtca       1150 acgtcgcac ccagagaaac accaatacca tgaaaaatta ccttttgccc        1200
gtagtggccc aggcatttgc taggtgggca aggaatatat aggaagatca       1250
agaagatgaa aggccactag gactacgaga tagacagtta gtcatggggt       1300
gttgttgggc ttttagaagg cacaagataa catctattta taagcgcccg       1350
gatacccaaa ccatcatcaa agtgaacagc gatttccact cattcgtgct       1400
gcccaggata ggcagtaaca cattggagat cgggctgaga acaagaatca       1450
ggaaaatgtt agaggagcac aaggagccgt cacctctcat taccgccgag       1500
gacgtacaag aagctaagtg cgcagccgat gaggctaagg aggtgcgtga       1550
agccgaggag ttgcgcgcag ctctaccacc tttggcagct gatgttgagg       1600
agcccactct ggaagccgat gtcgacttga tgttacaaga ggctggggcc       1650
ggctcagtgg agacacctcg tggcttgata aaggttacca gctacgatgg       1700
cgaggacaag atcggctctt acgctgtgct ttctccgcag gctgtactca       1750
agagtgaaaa attatcttgc atccaccctc tcgctgaaca agtcatagtg       1800
ataacacact ctgccgaaa agggcgttat gccgtggaac cataccatgg        1850
taaagtagtg gtgccagagg acatgcaat acccgtccag gactttcaag        1900
ctctgagtga aagtgccacc attgtgtaca acgaacgtga gttcgtaaac       1950
aggtacctgc accatattgc cacacatgga ggagcgctga cactgatga        2000 agaatattac aaaactgtca agcccagcga gcacgacggc gaatacctgt       2050
acgacatcga caggaaacag tgcgtcaaga agaaactagt cactgggcta       2100
gggctcacag gcgagctggt ggatcctccc ttccatgaat cgcctacga        2150 gagtctgaga acacgaccag ccgctcctta ccaagtacca accataggggg      2200 tgtatggcgt gccaggatca ggcaagtctg gcatcattaa aagcgcagtc       2250
accaaaaaag atcagtggt gagcgccaag aaagaaaact gtgcagaaat        2300
tataagggac gtcaagaaaa tgaaagggct ggacgtcaat gccagaactg       2350
tggactcagt gctcttgaat ggatgcaaac accccgtaga gaccctgtat       2400
```

| | |
|---|---|
| attgacgaag cttttgcttg tcatgcaggt actctcagag cgctcatagc | 2450 |
| cattataaga cctaaaaagg cagtgctctg cggggatccc aaacagtgcg | 2500 |
| gttttttttaa catgatgtgc ctgaaagtgc attttaacca cgagatttgc | 2550 |
| acacaagtct tccacaaaag catctctcgc cgttgcacta aatctgtgac | 2600 |
| ttcggtcgtc tcaaccttgt tttacgacaa aaaatgaga acgacgaatc | 2650 |
| cgaaagagac taagattgtg attgacacta ccggcagtac caaacctaag | 2700 |
| caggacgatc tcattctcac ttgtttcaga gggtgggtga agcagttgca | 2750 |
| aatagattac aaaggcaacg aaataatgac ggcagctgcc tctcaagggc | 2800 |
| tgacccgtaa aggtgtgtat gccgttcggt acaaggtgaa tgaaaatcct | 2850 |
| ctgtacgcac ccacctcaga acatgtgaac gtcctactga cccgcacgga | 2900 |
| ggaccgcatc gtgtggaaaa cactagccgg cgacccatgg ataaaaacac | 2950 |
| tgactgccaa gtaccctggg aatttcactg ccacgataga ggagtggcaa | 3000 |
| gcagagcatg atgccatcat gaggcacatc ttggagagac cggaccctac | 3050 |
| cgacgtcttc cagaataagg caaacgtgtg ttgggccaag ctttagtgc | 3100 |
| cggtgctgaa gaccgctggc atagacatga ccactgaaca atggaacact | 3150 |
| gtggattatt ttgaaacgga caaagctcac tcagcagaga tagtattgaa | 3200 |
| ccaactatgc gtgaggttct ttggactcga tctggactcc ggtctatttt | 3250 |
| ctgcacccac tgttccgtta tccattagga ataatcactg gataactcc | 3300 |
| ccgtcgccta acatgtacgg gctgaataaa gaagtggtcc gtcagctctc | 3350 |
| tcgcaggtac ccacaactgc ctcgggcagt tgccactgga agagtctatg | 3400 |
| acatgaacac tggtacactg cgcaattatg atccgcgcat aaacctagta | 3450 |
| cctgtaaaca gaagactgcc tcatgcttta gtcctccacc ataatgaaca | 3500 |
| cccacagagt gacttttctt cattcgtcag caaattgaag ggcagaactg | 3550 |
| tcctggtggt cggggaaaag ttgtccgtcc caggcaaaat ggttgactgg | 3600 |
| ttgtcagacc ggcctgaggc taccttcaga gctcggctgg atttaggcat | 3650 |
| cccaggtgat gtgcccaaat atgacataat atttgttaat gtgaggaccc | 3700 |
| catataaata ccatcactat cagcagtgtg aagaccatgc cattaagctt | 3750 |
| agcatgttga ccaagaaagc ttgtctgcat ctgaatcccg gcggaacctg | 3800 |
| tgtcagcata ggttatggtt acgctgacag ggccagcgaa agcatcattg | 3850 |
| gtgctatagc gcggcagttc aagttttccc gggtatgcaa accgaaatcc | 3900 |
| tcacttgaag agacggaagt tctgtttgta ttcattgggt acgatcgcaa | 3950 |
| ggcccgtacg cacaatcctt acaagctttc atcaaccttg accaacattt | 4000 |
| atacaggttc cagactccac gaagccggat gtgcaccctc atatcatgtg | 4050 |
| gtgcgagggg atattgccac ggccaccgaa ggagtgatta taaatgctgc | 4100 |
| taacagcaaa ggacaacctg gcggagggt gtgcggagcg ctgtataaga | 4150 |
| aattcccgga aagcttcgat ttacagccga tcgaagtagg aaaagcgcga | 4200 |
| ctggtcaaag gtgcagctaa acatatcatt catgccgtag gaccaaactt | 4250 |
| caacaaagtt tcggaggttg aaggtgacaa acagttggca gaggcttatg | 4300 |
| agtccatcgc taagattgtc aacgataaca attacaagtc agtagcgatt | 4350 |
| ccactgttgt ccaccggcat cttttccggg aacaaagatc gactaaccca | 4400 |

```
atcattgaac catttgctga cagctttaga caccactgat gcagatgtag      4450
ccatatactg cagggacaag aaatgggaaa tgactctcaa ggaagcagtg      4500
gctaggagag aagcagtgga ggagatatgc atatccgacg actcttcagt      4550
gacagaacct gatgcagagc tggtgagggt gcatccgaag agttctttgg      4600
ctggaaggaa gggctacagc acaagcgatg gcaaaacttt ctcatatttg      4650
gaagggacca agtttcacca ggcggccaag gatatagcag aaattaatgc      4700
catgtggccc gttgcaacgg aggccaatga gcaggtatgc atgtatatcc      4750
tcggagaaag catgagcagt attaggtcga aatgccccgt cgaagagtcg      4800
gaagcctcca caccacctag cacgctgcct tgcttgtgca tccatgccat      4850
gactccagaa agagtacagc gcctaaaagc ctcacgtcca gaacaaatta      4900
ctgtgtgctc atcctttcca ttgccgaagt atagaatcac tggtgtgcag      4950
aagatccaat gctcccagcc tatattgttc tcaccgaaag tgcctgcgta      5000
tattcatcca aggaagtatc tcgtggaaac accaccggta gacgagactc      5050
cggagccatc ggcagagaac caatccacag aggggacacc tgaacaacca      5100
ccacttataa ccgaggatga gaccaggact agaacgcctg agccgatcat      5150
catcgaagag gaagaagagg atagcataag tttgctgtca gatggcccga      5200
cccaccaggt gctgcaagtc gaggcagaca ttcacgggcc gccctctgta      5250
tctagctcat cctggtccat tcctcatgca tccgactttg atgtggacag      5300 tttatcccata cttgacaccc tggagggagc tagcgtgacc agcggggcaa      5350
cgtcagccga gactaactct tacttcgcaa agagtatgga gtttctggcg      5400
cgaccggtgc ctgcgcctcg aacagtattc aggaaccctc cacatcccgc      5450
tccgcgcaca agaacaccgt cacttgcacc cagcagggcc tgctcgagaa      5500
ccagcctagt ttccaccccg ccaggcgtga ataggggtgat cactagagag      5550 gagctcgagg cgcttacccc gtcacgcact cctagcaggt cggtctcgag      5600
aaccagcctg gtctccaacc cgccaggcgt aaatagggtg attacaagag      5650
aggagtttga ggcgttcgta gcacaacaac aatgacggtt tgatgcgggt      5700
gcatacatct tttcctccga caccggtcaa gggcatttac aacaaaaatc      5750
agtaaggcaa acgtgctat ccgaagtggt gttggagagg accgaattgg      5800
agatttcgta tgccccgcgc ctcgaccaag aaaaagaaga attactacgc      5850
aagaaattac agttaaatcc cacacctgct aacagaagca gataccagtc      5900
caggaaggtg gagaacatga aagccataac agctagacgt attctgcaag      5950
gcctagggca ttatttgaag gcagaaggaa aagtggagtg ctaccgaacc      6000
ctgcatcctg ttcctttgta ttcatctagt gtgaaccgtg cctttcaag      6050 ccccaaggtc gcagtggaag cctgtaacgc catgttgaaa gagaactttc      6100
cgactgtggc ttcttactgt attattccag agtacgatgc ctatttggac      6150
atggttgacg gagcttcatg ctgcttagac actgccagtt tttgccctgc      6200
aaagctgcgc agctttccaa agaaacactc ctatttggaa cccacaatac      6250
gatcggcagt gccttcagcg atccagaaca cgctccagaa cgtcctggca      6300
gctgccacaa aaagaaattg caatgtcacg caaatgagag aattgcccgt      6350
attggattcg gcggccttta atgtggaatg cttcaagaaa tatgcgtgta      6400
```

-continued

| | |
|---|---|
| ataatgaata ttgggaaacg tttaaagaaa accccatcag gcttactgaa | 6450 |
| gaaaacgtgg taaattacat taccaaatta aaaggaccaa aagctgctgc | 6500 |
| tcttttttgcg aagacacata atttgaatat gttgcaggac ataccaatgg | 6550 |
| acaggtttgt aatggactta aagagagacg tgaaagtgac tccaggaaca | 6600 |
| aaacatactg aagaacggcc caaggtacag gtgatccagg ctgccgatcc | 6650 |
| gctagcaaca gcgtatctgt gcggaatcca ccgagagctg gttaggagat | 6700 |
| taaatgcggt cctgcttccg aacattcata cactgtttga tatgtcggct | 6750 |
| gaagactttg acgctattat agccgagcac ttccagcctg gggattgtgt | 6800 |
| tctggaaact gacatcgcgt cgtttgataa aagtgaggac gacgccatgg | 6850 |
| ctctgaccgc gttaatgatt ctggaagact taggtgtgga cgcagagctg | 6900 |
| ttgacgctga ttgaggcggc tttcggcgaa atttcatcaa tacatttgcc | 6950 |
| cactaaaact aaatttaaat tcggagccat gatgaaatct ggaatgttcc | 7000 |
| tcacactgtt tgtgaacaca gtcattaaca ttgtaatcgc aagcagagtg | 7050 |
| ttgagagaac ggctaaccgg atcaccatgt gcagcattca ttggagatga | 7100 |
| caatatcgtg aaaggagtca aatcggacaa attaatggca gacaggtgcg | 7150 |
| ccacctggtt gaatatggaa gtcaagatta tagatgctgt ggtgggcgag | 7200 |
| aaagcgcctt atttctgtgg agggtttatt ttgtgtgact ccgtgaccgg | 7250 |
| cacagcgtgc cgtgtggcag accccctaaa aaggctgttt aagcttggca | 7300 |
| aacctctggc agcagacgat gaacatgatg atgacaggag aagggcattg | 7350 |
| catgaagagt caacacgctg gaaccgagtg ggtattcttt cagagctgtg | 7400 |
| caaggcagta gaatcaaggt atgaaaccgt aggaacttcc atcatagtta | 7450 |
| tggccatgac tactctagct agcagtgtta aatcattcag ctacctgaga | 7500 |
| ggggccccta taactctcta cggctaacct gaatggacta cgacatagtc | 7550 |
| tagtccgcca aagaggtgtt caaggattta tcttttttctt tttgttcaac | 7600 |
| attttgactg gaaaaaagat cacagcccac ctaaagaggt tgtggaaaat | 7650 |
| gctggaccca agacaaggct tggctgttct aaggaaagtc aagagagtgg | 7700 |
| tggccagttt gatgagagga ttgtcctcaa ggaaacgccg ttcccatgat | 7750 |
| gttctgactg tgcaattcct aattttggga atgctgttga tgacgggtgg | 7800 |
| agtgaccttg gtgcggaaaa acagatggtt gctcctaaat gtgacatctg | 7850 |
| aggacctcgg gtaagggccc ctataactct ctacggctaa cctgaatgga | 7900 |
| ctacgacata gtctagtccg ccaagtctag agcttaccat gaccgagtac | 7950 |
| aagcccacgg tgcgcctcgc cacccgcgac gacgtcccca gggccgtacg | 8000 |
| caccctcgcc gccgcgttcg ccgactaccc cgccacgcgc cacaccgtcg | 8050 |
| atccggaccg ccacatcgag cgggtcaccg agctgcaaga actcttcctc | 8100 |
| acgcgcgtcg ggctcgacat cggcaaggtg tgggtcgcgg acgacggcgc | 8150 |
| cgcggtggcg gtctggacca cgccggagag cgtcgaagcg ggggcggtgt | 8200 |
| tcgccgagat cggcccgcgc atggccgagt tgagcggttc ccggctggcc | 8250 |
| gcgcagcaac agatggaagg cctcctggcg ccgcaccggc ccaaggagcc | 8300 |
| cgcgtggttc ctggccaccg tcggcgtctc gcccgaccac cagggcaagg | 8350 |
| gtctgggcag cgccgtcgtg ctccccggag tggaggcggc cgagcgcgcc | 8400 |

| | |
|---|---|
| ggggtgcccg ccttcctgga gacctccgcg ccccgcaacc tccccttcta | 8450 |
| cgagcggctc ggcttcaccg tcaccgccga cgtcgagtgc ccgaaggacc | 8500 |
| gcgcgacctg gtgcatgacc cgcaagcccg gtgcctgacg cccgcccac | 8550 |
| gacccgcagc gcccgaccga aggagcgca cgacccatg atcgctagac | 8600 |
| catggggtac cgagtatgtt acgtgcaaag gtgattgtca ccccccgaaa | 8650 |
| gaccatattg tgacacaccc tcagtatcac gcccaaacat ttacagccgc | 8700 |
| ggtgtcaaaa accgcgtgga cgtggttaac atccctgctg ggaggatcag | 8750 |
| ccgtaattat tataattggc ttggtgctgg ctactattgt ggccatgtac | 8800 |
| gtgctgacca accagaaaca taattgaata cagcagcaat tggcaagctg | 8850 |
| cttacataga actcgcggcg attggcatgc cgccttaaaa tttttatttt | 8900 |
| atttttcctt ttcttttccg aatcggattt tgtttttaat atttcaaaaa | 8950 |
| aaaaaaaaaa aaaaaaaaaa cgcgtcgagg ggaattaatt cttgaagacg | 9000 |
| aaagggccag gtggcacttt tcggggaaat gtgcgcggaa cccctatttg | 9050 |
| tttattttc taaatacatt caaatatgta tccgctcatg agacaataac | 9100 |
| cctgataaat gcttcaataa tattgaaaaa ggaagagtat gagtattcaa | 9150 |
| catttccgtg tcgcccttat ccctttttt gcggcatttt gccttcctgt | 9200 |
| ttttgctcac ccagaaacgc tggtgaaagt aaaagatgct gaagatcagt | 9250 |
| tgggtgcacg agtgggttac atcgaactgg atctcaacag cggtaagatc | 9300 |
| cttgagagtt ttcgccccga agaacgtttt ccaatgatga gcacttttaa | 9350 |
| agttctgcta tgtggcgcgg tattatcccg tgttgacgcc gggcaagagc | 9400 |
| aactcggtcg ccgcatacac tattctcaga atgacttggt tgagtactca | 9450 |
| ccagtcacag aaaagcatct tacgatggc atgacagtaa gagaattatg | 9500 |
| cagtgctgcc ataaccatga gtgataacac tgcggccaac ttacttctga | 9550 |
| caacgatcgg aggaccgaag gagctaaccg ctttttttgca caacatgggg | 9600 |
| gatcatgtaa ctcgccttga tcgttgggaa ccggagctga atgaagccat | 9650 |
| accaaacgac gagcgtgaca ccacgatgcc tgtagcaatg gcaacaacgt | 9700 |
| tgcgcaaact attaactggc gaactactta ctctagcttc ccggcaacaa | 9750 |
| ttaatagact ggatggaggc ggataaagtt gcaggaccac ttctgcgctc | 9800 |
| ggcccttccg gctggctggt ttattgctga taaatctgga gccggtgagc | 9850 |
| gtgggtctcg cggtatcatt gcagcactgg ggccagatgg taagccctcc | 9900 |
| cgtatcgtag ttatctacac gacggggagt caggcaacta tggatgaacg | 9950 |
| aaatagacag atcgctgaga taggtgcctc actgattaag cattggtaac | 10000 |
| tgtcagacca agtttactca tatatacttt agattgattt aaaacttcat | 10050 |
| ttttaattta aaaggatcta ggtgaagatc ctttttgata atctcatgac | 10100 |
| caaaatccct taacgtgagt tttcgttcca ctgagcgtca gaccccgtag | 10150 |
| aaaagatcaa aggatcttct tgagatcctt ttttttctgcg cgtaatctgc | 10200 |
| tgcttgcaaa caaaaaaacc accgctacca gcggtggttt gtttgccgga | 10250 |
| tcaagagcta ccaactcttt ttccgaaggt aactggcttc agcagagcgc | 10300 |
| agataccaaa tactgtcctt ctagtgtagc cgtagttagg ccaccacttc | 10350 |
| aagaactctg tagcaccgcc tacatacctc gctctgctaa tcctgttacc | 10400 |

| | |
|---|---|
| agtggctgct gccagtggcg ataagtcgtg tcttaccggg ttggactcaa | 10450 |
| gacgatagtt accggataag gcgcagcggt cgggctgaac ggggggttcg | 10500 |
| tgcacacagc ccagcttgga gcgaacgacc tacaccgaac tgagatacct | 10550 |
| acagcgtgag cattgagaaa gcgccacgct tcccgaaggg agaaaggcgg | 10600 |
| acaggtatcc ggtaagcggc agggtcggaa caggagagcg cacgagggag | 10650 |
| cttccagggg gaaacgcctg gtatctttat agtcctgtcg ggtttcgcca | 10700 |
| cctctgactt gagcgtcgat ttttgtgatg ctcgtcaggg gggcggagcc | 10750 |
| tatggaaaaa cgccagcaac gcgagctcga tttaggtgac actata | 10796 |

<210> SEQ ID NO 9
<211> LENGTH: 12839
<212> TYPE: DNA
<213> ORGANISM: artificial sequence
<220> FEATURE:
<223> OTHER INFORMATION: sequence of pVEErep/V-prM-E/Pac plasmid

<400> SEQUENCE: 9

| | |
|---|---|
| gatgggcggc gcatgagaga agcccagacc aattacctac ccaaaatgga | 50 |
| gaaagttcac gttgacatcg aggaagacag cccattcctc agagctttgc | 100 |
| agcggagctt cccgcagttt gaggtagaag ccaagcaggt cactgataat | 150 |
| gaccatgcta atgccagagc gttttcgcat ctggcttcaa aactgatcga | 200 |
| aacggaggtg gacccatccg acacgatcct tgacattgga agtgcgcccg | 250 |
| cccgcagaat gtattctaag cacaagtatc attgtatctg tccgatgaga | 300 |
| tgtgcggaag atccggacag attgtataag tatgcaacta gcctgaagaa | 350 |
| aaactgtaag gaaataactg ataaggaatt ggacaagaaa atgaaggagc | 400 |
| tggccgccgt catgagcgac cctgacctgg aaactgagac tatgtgcctc | 450 |
| cacgacgacg agtcgtgtcg ctacgaaggg caagtcgctg tttaccagga | 500 |
| tgtatacgcg gttgacggac cgacaagtct ctatcaccaa gccaataagg | 550 |
| gagttagagt cgcctactgg ataggctttg acaccacccc ttttatgttt | 600 |
| aagaacttgg ctggagcata tccatcatac tctaccaact gggccgacga | 650 |
| aaccgtgtta acggctcgta acataggcct atgcagctct gacgttatgg | 700 |
| agcggtcacg tagagggatg tccattctta gaaagaagta tttgaaacca | 750 |
| tccaacaatg ttctattctc tgttggctcg accatctacc acgagaagag | 800 |
| ggacttactg aggagctggc acctgccgtc tgtatttcac ttacgtggca | 850 |
| agcaaaatta cacatgtcgg tgtgagacta tagttagttg cgacgggtac | 900 |
| gtcgttaaaa gaatagctat cagtccaggc ctgtatggga agccttcagg | 950 |
| ctatgctgct acgatgcacc gcgagggatt cttgtgctgc aaagtgacag | 1000 |
| acacattgaa cggggagagg gtctcttttc ccgtgtgcac gtatgtgcca | 1050 |
| gctacattgt gtgaccaaat gactggcata ctggcaacag atgtcagtgc | 1100 |
| ggacgacgcg caaaaactgc tggttgggct caaccagcgt atagtcgtca | 1150 |
| acggtcgcac ccagagaaac accaatacca tgaaaaatta ccttttgccc | 1200 |
| gtagtggccc aggcatttgc taggtgggca aggaatata aggaagatca | 1250 |
| agaagatgaa aggccactag gactacgaga tagacagtta gtcatggggt | 1300 |
| gttgttgggc ttttagaagg cacaagataa catctattta taagcgcccg | 1350 |

-continued

```
gatacccaaa ccatcatcaa agtgaacagc gatttccact cattcgtgct      1400
gcccaggata ggcagtaaca cattggagat cgggctgaga acaagaatca      1450
ggaaaatgtt agaggagcac aaggagccgt cacctctcat taccgccgag      1500
gacgtacaag aagctaagtg cgcagccgat gaggctaagg aggtgcgtga      1550
agccgaggag ttgcgcgcag ctctaccacc tttggcagct gatgttgagg      1600
agcccactct ggaagccgat gtcgacttga tgttacaaga ggctgggcc       1650
ggctcagtgg agacacctcg tggcttgata aaggttacca gctacgatgg      1700
cgaggacaag atcggctctt acgctgtgct ttctccgcag gctgtactca      1750
agagtgaaaa attatcttgc atccaccctc tcgctgaaca agtcatagtg      1800
ataacacact ctggccgaaa agggcgttat gccgtggaac cataccatgg      1850
taaagtagtg gtgccagagg acatgcaat acccgtccag gactttcaag       1900
ctctgagtga agtgccacc attgtgtaca acgaacgtga gttcgtaaac       1950
aggtacctgc accatattgc cacacatgga ggagcgctga acactgatga      2000
agaatattac aaaactgtca agcccagcga gcacgacggc gaatacctgt      2050
acgacatcga caggaaacag tgcgtcaaga agaactagt cactgggcta       2100
gggctcacag gcgagctggt ggatcctccc ttccatgaat tcgcctacga      2150
gagtctgaga acacgaccag ccgctcctta ccaagtacca accataggg       2200
tgtatggcgt gccaggatca ggcaagtctg gcatcattaa aagcgcagtc      2250
accaaaaaag atctagtggt gagcgccaag aaagaaaact gtgcagaaat      2300
tataagggac gtcaagaaaa tgaaagggct ggacgtcaat gccagaactg      2350
tggactcagt gctcttgaat ggatgcaaac accccgtaga gaccctgtat      2400
attgacgaag cttttgcttg tcatgcaggt actctcagag cgctcatagc      2450
cattataaga cctaaaaagg cagtgctctg cggggatccc aaacagtgcg      2500
gttttttaa catgatgtgc ctgaaagtgc atttttaacca cgagatttgc       2550
acacaagtct tccacaaaag catctctcgc cgttgcacta aatctgtgac      2600
ttcggtcgtc tcaaccttgt tttacgacaa aaaaatgaga acgacgaatc      2650
cgaaagagac taagattgtg attgacacta ccggcagtac caaacctaag      2700
caggacgatc tcattctcac ttgtttcaga gggtgggtga agcagttgca      2750
aatagattac aaaggcaacg aaataatgac ggcagctgcc tctcaagggc      2800
tgacccgtaa aggtgtgtat gccgttcggt acaaggtgaa tgaaaatcct      2850
ctgtacgcac ccacctcaga acatgtgaac gtcctactga cccgcacgga      2900
ggaccgcatc gtgtggaaaa cactagccgg cgacccatgg ataaaaacac      2950
tgactgccaa gtaccctggg aatttcactg ccacgataga ggagtggcaa      3000
gcagagcatg atgccatcat gaggcacatc ttggagagac cggaccctac      3050
cgacgtcttc cagaataagg caaacgtgtg ttgggccaag gctttagtgc      3100
cggtgctgaa gaccgctggc atagacatga ccactgaaca atggaacact      3150
gtggattatt ttgaaacgga caaagctcac tcagcagaga tagtattgaa      3200
ccaactatgc gtgaggttct ttggactcga tctggactcc ggtctatttt      3250
ctgcacccac tgttccgtta tccattagga ataatcactg gataactcc       3300
ccgtcgccta acatgtacgg gctgaataaa gaagtggtcc gtcagctctc      3350
```

```
tcgcaggtac ccacaactgc ctcgggcagt tgccactgga agagtctatg      3400
acatgaacac tggtacactg cgcaattatg atccgcgcat aaacctagta      3450
cctgtaaaca gaagactgcc tcatgcttta gtcctccacc ataatgaaca      3500
cccacagagt gacttttctt cattcgtcag caaattgaag ggcagaactg      3550
tcctggtggt cggggaaaag ttgtccgtcc caggcaaaat ggttgactgg      3600
ttgtcagacc ggcctgaggc taccttcaga gctcggctgg atttaggcat      3650
cccaggtgat gtgcccaaat atgacataat atttgttaat gtgaggaccc      3700
catataaata ccatcactat cagcagtgtg aagaccatgc cattaagctt      3750
agcatgttga ccaagaaagc ttgtctgcat ctgaatcccg gcggaacctg      3800
tgtcagcata ggttatggtt acgctgacag ggccagcgaa agcatcattg      3850
gtgctatagc gcggcagttc aagttttccc gggtatgcaa accgaaatcc      3900
tcacttgaag agacggaagt tctgtttgta ttcattgggt acgatcgcaa      3950
ggcccgtacg cacaatcctt acaagctttc atcaaccttg accaacattt      4000
atacaggttc cagactccac gaagccggat gtgcaccctc atatcatgtg      4050
gtgcgagggg atattgccac ggccaccgaa ggagtgatta taaatgctgc      4100
taacagcaaa ggacaacctg cggaggggt gtgcggagcg ctgtataaga      4150
aattcccgga aagcttcgat ttacagccga tcgaagtagg aaaagcgcga      4200
ctggtcaaag gtgcagctaa acatatcatt catgccgtag gaccaaactt      4250
caacaaagtt tcggaggttg aaggtgacaa acagttggca gaggcttatg      4300
agtccatcgc taagattgtc aacgataaca attacaagtc agtagcgatt      4350
ccactgttgt ccaccggcat ctttccgggg aacaaagatc gactaaccca      4400
atcattgaac catttgctga cagctttaga caccactgat gcagatgtag      4450
ccatatactg cagggacaag aaatgggaaa tgactctcaa ggaagcagtg      4500
gctaggagag aagcagtgga ggagatatgc atatccgacg actcttcagt      4550
gacagaacct gatgcagagc tggtgagggt gcatccgaag agttctttgg      4600
ctggaaggaa gggctacagc acaagcgatg gcaaaacttt ctcatatttg      4650
gaagggacca agtttcacca ggcggccaag gatatagcag aaattaatgc      4700
catgtggccc gttgcaacgg aggccaatga gcaggtatgc atgtatatcc      4750
tcggagaaag catgagcagt attaggtcga aatgccccgt cgaagagtcg      4800
gaagcctcca caccacctag cacgctgcct tgcttgtgca tccatgccat      4850
gactccagaa agagtacagc gcctaaaagc ctcacgtcca gaacaaatta      4900
ctgtgtgctc atcctttcca ttgccgaagt atagaatcac tggtgtgcag      4950
aagatccaat gctcccagcc tatattgttc tcaccgaaag tgcctgcgta      5000
tattcatcca aggaagtatc tcgtggaaac accaccggta gacgagactc      5050
cggagccatc ggcagagaac caatccacag aggggacacc tgaacaacca      5100
ccacttataa ccgaggatga gaccaggact agaacgcctg agccgatcat      5150
catcgaagag gaagaagagg atagcataag tttgctgtca gatggcccga      5200
cccaccaggt gctgcaagtc gaggcagaca ttcacgggcc gccctctgta      5250
tctagctcat cctggtccat tcctcatgca tccgactttg atgtggacag      5300
tttatccata cttgacaccc tggagggagc tagcgtgacc agcggggcaa      5350
```

| | |
|---|---|
| cgtcagccga gactaactct tacttcgcaa agagtatgga gtttctggcg | 5400 |
| cgaccggtgc ctgcgcctcg aacagtattc aggaaccctc acatcccgc | 5450 |
| tccgcgcaca agaacaccgt cacttgcacc cagcagggcc tgctcgagaa | 5500 |
| ccagcctagt ttccaccccg ccaggcgtga atagggtgat cactagagag | 5550 |
| gagctcgagg cgcttacccc gtcacgcact cctagcaggt cggtctcgag | 5600 |
| aaccagcctg gtctccaacc cgccaggcgt aaatagggtg attacaagag | 5650 |
| aggagtttga ggcgttcgta gcacaacaac aatgacggtt tgatgcgggt | 5700 |
| gcatacatct tttcctccga caccggtcaa gggcatttac aacaaaaatc | 5750 |
| agtaaggcaa acggtgctat ccgaagtggt gttggagagg accgaattgg | 5800 |
| agatttcgta tgccccgcgc ctcgaccaag aaaaagaaga attactacgc | 5850 |
| aagaaattac agttaaatcc cacacctgct aacagaagca gataccagtc | 5900 |
| caggaaggtg gagaacatga aagccataac agctagacgt attctgcaag | 5950 |
| gcctagggca ttatttgaag gcagaaggaa aagtggagtg ctaccgaacc | 6000 |
| ctgcatcctg ttcctttgta ttcatctagt gtgaaccgtg cctttcaag | 6050 |
| ccccaaggtc gcagtggaag cctgtaacgc catgttgaaa gagaactttc | 6100 |
| cgactgtggc ttcttactgt attattccag agtacgatgc ctatttggac | 6150 |
| atggttgacg gagcttcatg ctgcttagac actgccagtt tttgccctgc | 6200 |
| aaagctgcgc agcttttccaa agaaacactc ctatttggaa cccacaatac | 6250 |
| gatcggcagt gccttcagcg atccagaaca cgctccagaa cgtcctggca | 6300 |
| gctgccacaa aaagaaattg caatgtcacg caaatgagag aattgcccgt | 6350 |
| attggattcg gcggccttta atgtggaatg cttcaagaaa tatgcgtgta | 6400 |
| ataatgaata ttgggaaacg tttaaagaaa accccatcag gcttactgaa | 6450 |
| gaaaacgtgg taaattacat taccaaatta aaaggaccaa aagctgctgc | 6500 |
| tcttttttgcg aagacacata atttgaatat gttgcaggac ataccaatgg | 6550 |
| acaggttgt aatggactta agagagacg tgaaagtgac tccaggaaca | 6600 |
| aaacatactg aagaacggcc caaggtacag gtgatccagg ctgccgatcc | 6650 |
| gctagcaaca gcgtatctgt gcggaatcca ccgagagctg gttaggagat | 6700 |
| taaatgcggt cctgcttccg aacattcata cactgtttga tatgtcggct | 6750 |
| gaaagactttg acgctattat agccgagcac ttccagcctg gggattgtgt | 6800 |
| tctggaaact gacatcgcgt cgtttgataa aagtgaggac gacgccatgg | 6850 |
| ctctgaccgc gttaatgatt ctggaagact taggtgtgga cgcagagctg | 6900 |
| ttgacgctga ttgaggcggc tttcggcgaa atttcatcaa tacatttgcc | 6950 |
| cactaaaact aaatttaaat tcggagccat gatgaaatct ggaatgttcc | 7000 |
| tcacactgtt tgtgaacaca gtcattaaca ttgtaatcgc aagcagagtg | 7050 |
| ttgagagaac ggctaaccgg atcaccatgt gcagcattca ttggagatga | 7100 |
| caatatcgtg aaaggagtca atcggacaa attaatggca gacaggtgcg | 7150 |
| ccacctggtt gaatatggaa gtcaagatta tagatgctgt ggtgggcgag | 7200 |
| aaagcgcctt atttctgtgg agggtttatt ttgtgtgact ccgtgaccgg | 7250 |
| cacagcgtgc cgtgtggcag accccctaaa aaggctgttt aagcttggca | 7300 |
| aacctctggc agcagacgat gaacatgatg atgacaggag aagggcattg | 7350 |

```
catgaagagt caacacgctg gaaccgagtg ggtattcttt cagagctgtg      7400
caaggcagta gaatcaaggt atgaaaccgt aggaacttcc atcatagtta      7450
tggccatgac tactctagct agcagtgtta aatcattcag ctacctgaga      7500
gggcccccta taactctcta cggctaacct gaatggacta cgacatagtc      7550
tagtccgcca agtctagacc atgtctggtc gtaaagctca gggaaaaacc      7600
ctgggcgtca atatggtacg acgaggagtt cgctccttgt caaacaaaat      7650
aaaacaaaaa acaaaacaaa ttggaaacag acctggacct tcaagaggtg      7700
ttcaaggatt tatcttttc tttttgttca acattttgac tggaaaaaag       7750
atcacagccc acctaaagag gttgtggaaa atgctggacc caagacaagg      7800
cttggctgtt ctaaggaaag tcaagagagt ggtggccagt ttgatgagag      7850
gattgtcctc aaggaaacgc cgttcccatg atgttctgac tgtgcaattc      7900
ctaattttgg gaatgctgtt gatgacgggg ggagtgacct tggtgcggaa      7950
aaacagatgg ttgctcctaa atgtgacatc tgaggacctc gggaaaacat      8000
tctctgtggg cacaggcaac tgcacaacaa acattttgga agccaagtac      8050
tggtgcccag actcaatgga atacaactgt cccaatctca gtccaagaga      8100
ggagccagat gacattgatt gctggtgcta tggggtggaa aacgttagag      8150
tcgcatatgg taagtgtgac tcagcaggca ggtctaggag gtcaagaagg      8200
gccattgact tgcctacgca tgaaaaccat ggtttgaaga cccggcaaga      8250
aaaatggatg actggaagaa tgggtgaaag gcaactccaa aagattgaga      8300
gatggttcgt gaggaacccc ttttttgcag tgacggctct gaccattgcc      8350
taccttgtgg aagcaacat gacgcaacga gtcgtgattg ccctactggt       8400
cttggctgtt ggtccggcct actcagctca ctgcattgga attactgaca      8450
gggatttcat tgagggggtg catggaggaa cttgggtttc agctaccctg      8500
gagcaagaca agtgtgtcac tgttatggcc cctgacaagc cttcattgga      8550
catctcacta gagacagtag ccattgatag acctgctgag gtgaggaaag      8600
tgtgttacaa tgcagttctc actcatgtga agattaatga caagtgcccc      8650
agcactggag aggcccacct agctgaagag aacgaagggg acaatgcgtg      8700
caagcgcact tattctgata gaggctgggg caatggctgt ggcctatttg      8750
ggaaagggag cattgtggca tgcgccaaat tcacttgtgc caaatccatg      8800
agtttgtttg aggttgatca gaccaaaatt cagtatgtca tcagagcaca      8850
attgcatgta ggggccaagc aggaaaattg gaataccgac attaagactc      8900
tcaagtttga tgccctgtca ggctcccagg aagtcgagtt cattgggtat      8950
ggaaaagcta cactgaatg ccaggtgcaa actgcggtgg actttggtaa       9000
cagttacatc gctgagatgg aaacagagag ctggatagtg gacagacagt      9050
gggcccagga cttgaccctg ccatggcaga gtggaagtgg cggggtgtgg      9100
agagagatgc atcatcttgt cgaatttgaa cctccgcatg ccgccactat      9150
cagagtactg gccctgggaa accaggaagg ctccttgaaa acagctctta      9200
ctggcgcaat gagggttaca aaggacacaa atgacaacaa cctttacaaa      9250
ctacatggtg gacatgtttc ttgcagagtg aaattgtcag cttttgacact     9300
caaggggaca tcctacaaaa tatgcactga caaaatgttt tttgtcaaga     9350
```

| | |
|---|---|
| acccaactga cactggccat ggcactgttg tgatgcaggt gaaagtgtca | 9400 |
| aaaggagccc cctgcaggat tccagtgata gtagctgatg atcttacagc | 9450 |
| ggcaatcaat aaaggcattt tggttacagt taaccccatc gcctcaacca | 9500 |
| atgatgatga agtgctgatt gaggtgaacc caccttttgg agacagctac | 9550 |
| attatcgttg ggagaggaga ttcacgtctc acttaccagt ggcacaaaga | 9600 |
| gggaagctca ataggaaagt tgttcactca gaccatgaaa ggcgtggaac | 9650 |
| gcctggccgt catgggagac accgcctggg atttcagctc cgctggaggg | 9700 |
| ttcttcactt cggttgggaa aggaattcat acggtgtttg gctctgcctt | 9750 |
| tcagggcta tttggcggct tgaactggat aacaaaggtc atcatggggg | 9800 |
| cggtacttat atgggttggc atcaacacaa gaaacatgac aatgtccatg | 9850 |
| agcatgatct tggtaggagt gatcatgatg tttttgtctc taggagttgg | 9900 |
| ggcgtaagcg gcccctataa ctctctacgg ctaacctgaa tggactacga | 9950 |
| catagtctag tccgccaagt ctagagctta ccatgaccga gtacaagccc | 10000 |
| acggtgcgcc tcgccacccg cgacgacgtc cccagggccg tacgcaccct | 10050 |
| cgccgccgcg ttcgccgact accccgccac gcgccacacc gtcgatccgg | 10100 |
| accgccacat cgagcgggtc accgagctgc aagaactctt cctcacgcgc | 10150 |
| gtcgggctcg acatcggcaa ggtgtgggtc gcggacgacg gcgccgcggt | 10200 |
| ggcggtctgg accacgccgg agagcgtcga agcgggggcg gtgttcgccg | 10250 |
| agatcggccc gcgcatggcc gagttgagcg gttcccggct ggccgcgcag | 10300 |
| caacagatgg aaggcctcct ggcgccgcac cggcccaagg agcccgcgtg | 10350 |
| gttcctggcc accgtcggcg tctcgcccga ccaccagggc aagggtctgg | 10400 |
| gcagcgccgt cgtgctcccc ggagtggagg cggccgagcg cgccggggtg | 10450 |
| cccgccttcc tggagacctc cgcgcccgc aacctcccct tctacgagcg | 10500 |
| gctcggcttc accgtcaccg ccgacgtcga gtgcccgaag accgcgcga | 10550 |
| cctggtgcat gacccgcaag cccggtgcct gacgcccgcc ccacgacccg | 10600 |
| cagcgcccga ccgaaaggag cgcacgaccc catgatcgct agaccatggg | 10650 |
| gtaccgagta tgttacgtgc aaaggtgatt gtcaccccc gaaagaccat | 10700 |
| attgtgacac accctcagta tcacgcccaa acatttacag ccgcggtgtc | 10750 |
| aaaaaccgcg tggacgtggt taacatccct gctggggaga tcagccgtaa | 10800 |
| ttattataat tggcttggtg ctggctacta ttgtggccat gtacgtgctg | 10850 |
| accaaccaga aacataattg aatacagcag caattggcaa gctgcttaca | 10900 |
| tagaactcgc ggcgattggc atgccgcctt aaaatttta tttattttt | 10950 |
| tcttttcttt tccgaatcgg attttgtttt taatatttca aaaaaaaaa | 11000 |
| aaaaaaaaa aaacgcgtc gagggaatt aattcttgaa gacgaaaggg | 11050 |
| ccaggtggca cttttcgggg aaatgtgcgc ggaaccccta tttgtttatt | 11100 |
| tttctaaata cattcaaata tgtatccgct catgagacaa taaccctgat | 11150 |
| aaatgcttca ataatattga aaaggaaga gtatgagtat tcaacatttc | 11200 |
| cgtgtcgccc ttattccctt ttttgcggca ttttgccttc ctgttttgc | 11250 |
| tcacccagaa acgctggtga agtaaaaga tgctgaagat cagttgggtg | 11300 |
| cacgagtggg ttacatcgac tggatctcaa cagcggtaag atccttgaga | 11350 |

| | |
|---|---:|
| gttttcgccc cgaagaacgt tttccaatga tgagcacttt taaagttctg | 11400 |
| ctatgtggcg cggtattatc ccgtgttgac gccgggcaag agcaactcgg | 11450 |
| tcgccgcata cactattctc agaatgactt ggttgagtac tcaccagtca | 11500 |
| cagaaaagca tcttacggat ggcatgacag taagagaatt atgcagtgct | 11550 |
| gccataacca tgagtgataa cactgcggcc aacttacttc tgacaacgat | 11600 |
| cggaggaccg aaggagctaa ccgcttttt gcacaacatg ggggatcatg | 11650 |
| taactcgcct tgatcgttgg aaccggagc tgaatgaagc cataccaaac | 11700 |
| gacgagcgtg acaccacgat gcctgtagca atggcaacaa cgttgcgcaa | 11750 |
| actattaact ggcgaactac ttactctagc ttcccggcaa caattaatag | 11800 |
| actggatgga ggcggataaa gttgcaggac cacttctgcg ctcggccctt | 11850 |
| ccggctggct ggtttattgc tgataaatct ggagccggtg agcgtgggtc | 11900 |
| tcgcggtatc attgcagcac tggggccaga tggtaagccc tcccgtatcg | 11950 |
| tagttatcta cacgacgggg agtcaggcaa ctatggatga acgaaataga | 12000 |
| cagatcgctg agataggtgc ctcactgatt aagcattggt aactgtcaga | 12050 |
| ccaagtttac tcatatatac tttagattga tttaaaactt cattttaat | 12100 |
| ttaaaaggat ctaggtgaag atcctttttg ataatctcat gaccaaaatc | 12150 |
| ccttaacgtg agttttcgtt ccactgagcg tcagaccccg tagaaaagat | 12200 |
| caaaggatct tcttgagatc ctttttttct gcgcgtaatc tgctgcttgc | 12250 |
| aaacaaaaaa accaccgcta ccagcggtgg tttgtttgcc ggatcaagag | 12300 |
| ctaccaactc tttttccgaa ggtaactggc ttcagcagag cgcagatacc | 12350 |
| aaatactgtc cttctagtgt agccgtagtt aggccaccac ttcaagaact | 12400 |
| ctgtagcacc gcctacatac ctcgctctgc taatcctgtt accagtggct | 12450 |
| gctgccagtg gcgataagtc gtgtcttacc gggttggact caagacgata | 12500 |
| gttaccggat aaggcgcagc ggtcgggctg aacggggggt tcgtgcacac | 12550 |
| agcccagctt ggagcgaacg acctacaccg aactgagata cctacagcgt | 12600 |
| gagcattgag aaagcgccac gcttcccgaa gggagaaagg cggacaggta | 12650 |
| tccggtaagc ggcagggtcg gaacaggaga gcgcacgagg gagcttccag | 12700 |
| ggggaaacgc ctggtatctt tatagtcctg tcgggtttcg ccacctctga | 12750 |
| cttgagcgtc gatttttgtg atgctcgtca ggggggcgga gcctatggaa | 12800 |
| aaacgccagc aacgcgagct cgatttaggt gacactata | 12839 |

<210> SEQ ID NO 10
<211> LENGTH: 10926
<212> TYPE: DNA
<213> ORGANISM: artificial sequence
<220> FEATURE:
<223> OTHER INFORMATION: sequence of VEErep/C2opt/pac plasmid

<400> SEQUENCE: 10

| | |
|---|---:|
| gatgggcggc gcatgagaga agcccagacc aattacctac ccaaaatgga | 50 |
| gaaagttcac gttgacatcg aggaagacag cccattcctc agagctttgc | 100 |
| agcggagctt cccgcagttt gaggtagaag ccaagcaggt cactgataat | 150 |
| gaccatgcta atgccagagc gttttcgcat ctggcttcaa aactgatcga | 200 |
| aacggaggtg gacccatccg acacgatcct tgacattgga agtgcgcccg | 250 |

| | |
|---|---|
| cccgcagaat gtattctaag cacaagtatc attgtatctg tccgatgaga | 300 |
| tgtgcggaag atccggacag attgtataag tatgcaacta agctgaagaa | 350 |
| aaactgtaag gaaataactg ataaggaatt ggacaagaaa atgaaggagc | 400 |
| tggccgccgt catgagcgac cctgacctgg aaactgagac tatgtgcctc | 450 |
| cacgacgacg agtcgtgtcg ctacgaaggg caagtcgctg tttaccagga | 500 |
| tgtatacgcg gttgacggac cgacaagtct ctatcaccaa gccaataagg | 550 |
| gagttagagt cgcctactgg ataggctttg acaccacccc ttttatgttt | 600 |
| aagaacttgg ctggagcata tccatcatac tctaccaact gggccgacga | 650 |
| aaccgtgtta acggctcgta acataggcct atgcagctct gacgttatgg | 700 |
| agcggtcacg tagagggatg tccattctta gaaagaagta tttgaaacca | 750 |
| tccaacaatg ttctattctc tgttggctcg accatctacc acgagaagag | 800 |
| ggacttactg aggagctggc acctgccgtc tgtatttcac ttacgtggca | 850 |
| agcaaaatta cacatgtcgg tgtgagacta tagttagttg cgacgggtac | 900 |
| gtcgttaaaa gaatagctat cagtccaggc ctgtatggga agccttcagg | 950 |
| ctatgctgct acgatgcacc gcgagggatt cttgtgctgc aaagtgacag | 1000 |
| acacattgaa cggggagagg gtctcttttc ccgtgtgcac gtatgtgcca | 1050 |
| gctacattgt gtgaccaaat gactggcata ctggcaacag atgtcagtgc | 1100 |
| ggacgacgcg caaaaactgc tggttgggct caaccagcgt atagtcgtca | 1150 |
| acggtcgcac ccagagaaac accaatacca tgaaaaatta cctttttgccc | 1200 |
| gtagtggccc aggcatttgc taggtgggca aggaatatata aggaagatca | 1250 |
| agaagatgaa aggccactag gactacgaga tagacagtta gtcatggggt | 1300 |
| gttgttgggc ttttagaagg cacaagataa catctattta taagcgcccg | 1350 |
| gatacccaaa ccatcatcaa agtgaacagc gatttccact cattcgtgct | 1400 |
| gcccaggata ggcagtaaca cattggagat cgggctgaga acaagaatca | 1450 |
| ggaaaatgtt agaggagcac aaggagccgt cacctctcat taccgccgag | 1500 |
| gacgtacaag aagctaagtg cgcagccgat gaggctaagg aggtgcgtga | 1550 |
| agccgaggag ttgcgcgcag ctctaccacc tttggcagct gatgttgagg | 1600 |
| agcccactct ggaagccgat gtcgacttga tgttacaaga ggctggggcc | 1650 |
| ggctcagtgg agacacctcg tggcttgata aaggttacca gctacgatgg | 1700 |
| cgaggacaag atcggctctt acgctgtgct ttctccgcag gctgtactca | 1750 |
| agagtgaaaa attatcttgc atccaccctc tcgctgaaca agtcatagtg | 1800 |
| ataacacact ctggccgaaa agggcgttat gccgtggaac cataccatgg | 1850 |
| taaagtagtg gtgccagagg gacatgcaat acccgtccag gactttcaag | 1900 |
| ctctgagtga agtgccacc attgtgtaca acgaacgtga gttcgtaaac | 1950 |
| aggtacctgc accatattgc cacacatgga ggagcgctga acactgatga | 2000 |
| agaatattac aaaactgtca agcccagcga gcacgacggc gaatacctgt | 2050 |
| acgacatcga caggaaacag tgcgtcaaga aagaactagt cactgggcta | 2100 |
| gggctcacag gcgagctggt ggatcctccc ttccatgaat tcgcctacga | 2150 |
| gagtctgaga acacgaccag ccgctcctta ccaagtacca accataggg | 2200 |
| tgtatggcgt gccaggatca ggcaagtctg gcatcattaa aagcgcagtc | 2250 |

```
accaaaaaag atctagtggt gagcgccaag aaagaaaact gtgcagaaat    2300
tataagggac gtcaagaaaa tgaaagggct ggacgtcaat gccagaactg    2350
tggactcagt gctcttgaat ggatgcaaac accccgtaga gaccctgtat    2400
attgacgaag cttttgcttg tcatgcaggt actctcagag cgctcatagc    2450
cattataaga cctaaaaagg cagtgctctg cggggatccc aaacagtgcg    2500 gttttttaa catgatgtgc ctgaaagtgc attttaacca cgagatttgc     2550
acacaagtct tccacaaaag catctctcgc cgttgcacta aatctgtgac    2600
ttcggtcgtc tcaaccttgt tttacgacaa aaaaatgaga acgacgaatc    2650
cgaaagagac taagattgtg attgacacta ccggcagtac caaacctaag    2700
caggacgatc tcattctcac ttgttttcaga gggtgggtga agcagttgca   2750
aatagattac aaaggcaacg aaataatgac ggcagctgcc tctcaagggc    2800
tgacccgtaa aggtgtgtat gccgttcggt acaaggtgaa tgaaaatcct    2850
ctgtacgcac ccacctcaga acatgtgaac gtcctactga cccgcacgga    2900
ggaccgcatc gtgtggaaaa cactagccgg cgacccatgg ataaaaacac    2950
tgactgccaa gtaccctggg aatttcactg ccacgataga ggagtggcaa    3000
gcagagcatg atgccatcat gaggcacatc ttggagagac cggaccctac    3050
cgacgtcttc cagaataagg caaacgtgtg ttgggccaag gctttagtgc    3100
cggtgctgaa gaccgctggc atagacatga ccactgaaca atggaacact    3150
gtggattatt ttgaaacgga caaagctcac tcagcagaga tagtattgaa    3200
ccaactatgc gtgaggttct ttggactcga tctggactcc ggtctatttt    3250
ctgcacccac tgttccgtta tccattagga ataatcactg ggataactcc    3300
ccgtcgccta acatgtacgg gctgaataaa gaagtggtcc gtcagctctc    3350
tcgcaggtac ccacaactgc ctcgggcagt tgccactgga agagtctatg    3400
acatgaacac tggtacactg cgcaattatg atccgcgcat aaacctagta    3450
cctgtaaaca gaagactgcc tcatgcttta gtcctccacc ataatgaaca    3500
cccacagagt gacttttctt cattcgtcag caaattgaag ggcagaactg    3550
tcctggtggt cggggaaaag ttgtccgtcc caggcaaaat ggttgactgg    3600
ttgtcagacc ggcctgaggc taccttcaga gctcggctgg atttaggcat    3650
cccaggtgat gtgcccaaat atgacataat atttgttaat gtgaggaccc    3700
catataaata ccatcactat cagcagtgtg aagaccatgc cattaagctt    3750
agcatgttga ccaagaaagc ttgtctgcat ctgaatcccg gcggaacctg    3800
tgtcagcata ggttatggtt acgctgacag ggccagcgaa agcatcattg    3850
gtgctatagc gcggcagttc aagttttccc gggtatgcaa accgaaatcc    3900
tcacttgaag agacggaagt tctgtttgta ttcattgggt acgatcgcaa    3950
ggcccgtacg cacaatcctt acaagctttc atcaaccttg accaacattt    4000
atacaggttc cagactccac gaagccggat gtgcaccctc atatcatgtg    4050
gtgcgagggg atattgccac ggccaccgaa ggagtgatta taaatgctgc    4100
taacagcaaa ggacaacctg gcggagggt gtgcggagcg ctgtataaga    4150
aattcccgga aagcttcgat ttacagccga tcgaagtagg aaaagcgcga    4200
ctggtcaaag gtgcagctaa acatatcatt catgccgtag gaccaaactt    4250
```

```
caacaaagtt tcggaggttg aaggtgacaa acagttggca gaggcttatg        4300
agtccatcgc taagattgtc aacgataaca attacaagtc agtagcgatt        4350
ccactgttgt ccaccggcat ttttccggga acaaagatcg actaacccaa        4400
tcattgaacc atttgctgac agctttagac accactgatg cagatgtagc        4450
catatactgc agggacaaga aatgggaaat gactctcaag gaagcagtgg        4500
ctaggagaga agcagtggag gagatatgca tatccgacga ctcttcagtg        4550
acagaacctg atgcagagct ggtgagggtg catccgaaga gttctttggc        4600
tggaaggaag ggctacagca caagcgatgg caaaactttc tcatatttgg        4650
aagggaccaa gtttcaccag gcggccaagg atatagcaga aattaatgcc        4700
atgtggcccg ttgcaacgga ggccaatgag caggtatgca tgtatatcct        4750
cggagaaagc atgagcagta ttaggtcgaa atgccccgtc gaagagtcgg        4800
aagcctccac accacctagc acgctgcctt gcttgtgcat ccatgccatg        4850
actccagaaa gagtacagcg cctaaaagcc tcacgtccag aacaaattac        4900
tgtgtgctca tcctttccat tgccgaagta tagaatcact ggtgtgcaga        4950
agatccaatg ctcccagcct atattgttct caccgaaagt gcctgcgtat        5000
attcatccaa ggaagtatct cgtggaaaca ccaccggtag acgagactcc        5050
ggagccatcg gcagagaacc aatccacaga ggggacacct gaacaaccac        5100
cacttataac cgaggatgag accaggacta gaacgcctga gccgatcatc        5150
atcgaagagg aagaagagga tagcataagt ttgctgtcag atggcccgac        5200
ccaccaggtg ctgcaagtcg aggcagacat tcacgggccg ccctctgtat        5250
ctagctcatc ctggtccatt cctcatgcat ccgactttga tgtggacagt        5300
ttatccatac ttgacaccct ggagggagct agcgtgacca gcggggcaac        5350
gtcagccgag actaactctt acttcgcaaa gagtatggag tttctggcgc        5400
gaccggtgcc tgcgcctcga acagtattca ggaaccctcc acatcccgct        5450
ccgcgcacaa gaacaccgtc acttgcaccc agcagggcct gctcgagaac        5500
cagcctagtt tccacccccgc caggcgtgaa tagggtgatc actagagagg        5550
agctcgaggc gcttaccccg tcacgcactc ctagcaggtc ggtctcgaga        5600
accagcctgg tctccaaccc gccaggcgta aatagggtga ttacaagaga        5650
ggagtttgag gcgttcgtag cacaacaaca atgacggttt gatgcgggtg        5700
catacatctt ttcctccgac accggtcaag ggcatttaca acaaaaatca        5750
gtaaggcaaa cggtgctatc cgaagtggtg ttggagagga ccgaattgga        5800
gatttcgtat gccccgcgcc tcgaccaaga aaaagaagaa ttactacgca        5850
agaaattaca gttaaatccc acacctgcta acagaagcag ataccagtcc        5900
aggaaggtgg agaacatgaa agccataaca gctagacgta ttctgcaagg        5950
cctagggcat tatttgaagg cagaaggaaa agtggagtgc taccgaaccc        6000
tgcatcctgt tcctttgtat tcatctagtg tgaaccgtgc cttttcaagc        6050
cccaaggtcg cagtggaagc ctgtaacgcc atgttgaaag agaactttcc        6100
gactgtggct tcttactgta ttattccaga gtacgatgcc tatttggaca        6150
tggttgacgg agcttcatgc tgcttagaca ctgccagttt ttgccctgca        6200
aagctgcgca gctttccaaa gaaacactcc tatttggaac ccacaatacg        6250
```

```
atcggcagtg ccttcagcga tccagaacac gctccagaac gtcctggcag      6300
ctgccacaaa aagaaattgc aatgtcacgc aaatgagaga attgcccgta      6350
ttggattcgg cggcctttaa tgtggaatgc ttcaagaaat atgcgtgtaa      6400
taatgaatat tgggaaacgt ttaaagaaaa ccccatcagg cttactgaag      6450
aaaacgtggt aaattacatt accaaattaa aaggaccaaa agctgctgct      6500 cttttttgcga agacacataa tttgaatatg ttgcaggaca taccaatgga      6550
caggtttgta atggacttaa agagagacgt gaaagtgact ccaggaacaa      6600
aacatactga agaacggccc aaggtacagg tgatccaggc tgccgatccg      6650
ctagcaacag cgtatctgtg cggaatccac cgagagctgg ttaggagatt      6700
aaatgcggtc ctgcttccga acattcatac actgtttgat atgtcggctg      6750
aagactttga cgctattata gccgagcact ccagcctggg ggattgtgtt      6800
ctggaaactg acatcgcgtc gtttgataaa agtgaggacg acgccatggc      6850
tctgaccgcg ttaatgattc tggaagactt aggtgtggac gcagagctgt      6900
tgacgctgat tgaggcggct ttcggcgaaa tttcatcaat acatttgccc      6950
actaaaacta aatttaaatt cggagccatg atgaaatctg gaatgttcct      7000
cacactgttt gtgaacacag tcattaacat tgtaatcgca agcagagtgt      7050
tgagagaacg gctaaccgga tcaccatgtg cagcattcat tggagatgac      7100
aatatcgtga aaggagtcaa atcggacaaa ttaatggcag acaggtgcgc      7150
cacctggttg aatatggaag tcaagattat agatgctgtg gtgggcgaga      7200
aagcgcctta tttctgtgga gggttttattt tgtgtgactc cgtgaccggc      7250
acagcgtgcc gtgtggcaga ccccctaaaa aggctgttta agcttggcaa      7300
acctctggca gcagacgatg aacatgatga tgacaggaga agggcattgc      7350
atgaagagtc aacacgctgg aaccgagtgg gtattctttc agagctgtgc      7400
aaggcagtag aatcaaggta tgaaaccgta ggaacttcca tcatagttat      7450
ggccatgact actctagcta gcagtgttaa atcattcagc tacctgagag      7500
gggcccctat aactctctac ggctaacctg aatggactac gacatagtct      7550
agtccgccaa gtctagacca tgagcggccg gaaggctcag ggcaagaccc      7600
tgggcgtgaa catggtgagg cgcggcgtgc gcagcctctc caacaagatc      7650
aagcagaaga ccaagcagat cggcaacaga cccggaccga gccggggcgt      7700
ccaggggttc atcttcttct tcctgttcaa catcctcaca ggtaagaaga      7750
tcacggctca cctgaagagg ctctggaaga tgctggaccc tcgccagggg      7800
ctcgcggtgc tcagaaaggt gaagcgggtc gtcgcctccc tgatgcgcgg      7850
cctgtcctct cgcaagaggc gctcccacga tgtgctcacc gtccaattcc      7900
tcattctgga atgctgctga tgactggcgg cgtgaccctg gtgcgcaaga      7950
accgctggct gctgctgaat gtgaccagtg aggacctcgg gtaagggccc      8000
ctataactct ctacggctaa cctgaatgga ctacgacata gtctagtccg      8050
ccaagtctag agcttaccat gaccgagtac aagcccacgg tgcgcctcgc      8100
cacccgcgac gacgtcccca gggccgtacg caccctcgcc gccgcgttcg      8150
ccgactaccc cgccacgcgc cacaccgtcg atcggaccg ccacatcgag      8200 cgggtcaccg agctgcaaga actcttcctc acgcgcgtcg ggctcgacat      8250
```

```
cggcaaggtg tgggtcgcgg acgacggcgc cgcggtggcg gtctggacca      8300
cgccggagag cgtcgaagcg ggggcggtgt tcgccgagat cggcccgcgc      8350
atggccgagt tgagcggttc ccggctggcc gcgcagcaac agatggaagg      8400
cctcctggcg ccgcaccggc ccaaggagcc cgcgtggttc ctggccaccg      8450
tcggcgtctc gcccgaccac cagggcaagg gtctgggcag cgccgtcgtg      8500
ctccccggag tggaggcggc cgagcgcgcc ggggtgcccg ccttcctgga      8550
gacctccgcg ccccgcaacc tcccttccta cgagcggctc ggcttcaccg      8600
tcaccgccga cgtcgaggtg cccgaaggac cgcgcacctg gtgcatgacc      8650
cgcaagcccg gtgcctgacg cccgccccac gacccgcagc gcccgaccga      8700
aaggagcgca cgaccccatg atcgctagac catggggtac cgagtatgtt      8750
acgtgcaaag gtgattgtca ccccccgaaa gaccatattg tgacacaccc      8800
tcagtatcac gcccaaacat ttacagccgc ggtgtcaaaa accgcgtgga      8850
cgtggttaac atccctgctg ggaggatcag ccgtaattat tataattggc      8900
ttggtgctgg ctactattgt ggccatgtac gtgctgacca accagaaaca      8950
taattgaata cagcagcaat tggcaagctg cttacataga actcgcggcg      9000
attggcatgc cgccttaaaa ttttttatttt atttttttctt ttcttttccg     9050
aatcggattt tgttttttaat atttcaaaaa aaaaaaaaa aaaaaaaaa       9100
cgcgtcgagg ggaattaatt cttgaagacg aaagggccag gtggcacttt      9150
tcggggaaat gtgcgcggaa cccctatttg tttatttttc taaatacatt      9200
caaatatgta tccgctcatg agacaataac cctgataaat gcttcaataa      9250
tattgaaaaa ggaagagtat gagtattcaa catttccgtg tcgcccttat      9300
tcccttttttt gcggcatttt gccttcctgt ttttgctcac ccagaaacgc     9350
tggtgaaagt aaaagatgct gaagatcagt tgggtgcacg agtgggttac      9400
atcgaactgg atctcaacag cggtaagatc cttgagagtt ttcgccccga      9450
agaacgtttt ccaatgatga gcacttttaa agttctgcta tgtggcgcgg      9500
tattatcccg tgttgacgcc gggcaagagc aactcggtcg ccgcatacac      9550
tattctcaga atgacttggt tgagtactca ccagtcacag aaaagcatct      9600
tacggatggc atgacagtaa gagaattatg cagtgctgcc ataaccatga      9650
gtgataaacac tgcggccaac ttacttctga caacgatcgg aggaccgaag     9700
gagctaaccg cttttttgca caacatgggg gatcatgtaa ctcgccttga     9750
tcgttgggaa ccggagctga atgaagccat accaaacgac gagcgtgaca     9800
ccacgatgcc tgtagcaatg gcaacaacgt tgcgcaaact attaactggc     9850
gaactactta ctctagcttc ccggcaacaa ttaatagact ggatggaggc      9900
ggataaagtt gcaggaccac ttctgcgctc ggcccttccg gctggctggt     9950
ttattgctga taaatctgga gccggtgagc gtgggtctcg cggtatcatt      10000
gcagcactgg ggccagatgg taagccctcc cgtatcgtag ttatctacac      10050
gacgggagt caggcaacta tggatgaacg aaatagacag atcgctgaga       10100
taggtgcctc actgattaag cattggtaac tgtcagacca agtttactca      10150
tatatacttt agattgattt aaaacttcat ttttaattta aaaggatcta      10200
ggtgaagatc cttttttgata atctcatgac caaaatccct taacgtgagt      10250
```

| | |
|---|---|
| tttcgttcca ctgagcgtca gaccccgtag aaaagatcaa aggatcttct | 10300 |
| tgagatcctt tttttctgcg cgtaatctgc tgcttgcaaa caaaaaaacc | 10350 |
| accgctacca gcggtggttt gtttgccgga tcaagagcta ccaactcttt | 10400 |
| ttccgaaggt aactggcttc agcagagcgc agataccaaa tactgtcctt | 10450 |
| ctagtgtagc cgtagttagg ccaccacttc aagaactctg tagcaccgcc | 10500 |
| tacataccct gctctgctaa tcctgttacc agtggctgct gccagtggcg | 10550 |
| ataagtcgtg tcttaccggg ttggactcaa gacgatagtt accggataag | 10600 |
| gcgcagcggt cgggctgaac ggggggttcg tgcacacagc ccagcttgga | 10650 |
| gcgaacgacc tacaccgaac tgagatacct acagcgtgag cattgagaaa | 10700 |
| gcgccacgct tcccgaaggg agaaaggcgg acaggtatcc ggtaagcggc | 10750 |
| agggtcggaa caggagagcg cacgagggag cttccagggg gaaacgcctg | 10800 |
| gtatctttat agtcctgtcg ggtttcgcca cctctgactt gagcgtcgat | 10850 |
| ttttgtgatg ctcgtcaggg gggcggagcc tatggaaaaa cgccagcaac | 10900 |
| gcgagctcga tttaggtgac actata | 10926 |

<210> SEQ ID NO 11
<211> LENGTH: 12836
<212> TYPE: DNA
<213> ORGANISM: artificial sequence
<220> FEATURE:
<223> OTHER INFORMATION: sequence of VEErep/Copt-prM-E/Pac plasmid

<400> SEQUENCE: 11

```
gatgggcggc gcatgagaga agcccagacc aattacctac ccaaaatgga            50
gaaagttcac gttgacatcg aggaagacag cccattcctc aagagctttg           100
cagcggagct tcccgcagtt tgaggtagaa gccaagcagg tcactgataa           150
tgaccatgct aatgccagag cgttttcgca tctggcttca aaactgatcg           200
aaacggaggt ggacccatcc gacacgatcc ttgacattgg aagtgcgccc           250
gcccgcagaa tgtattctaa gcacaagtat cattgtatct gtccgatgag           300
atgtgcggaa gatccggaca gattgtataa gtatgcaact aagctgaaga           350
aaaactgtaa ggaaataact gataaggaat tggacaagaa aatgaaggag           400
ctggccgccg tcatgagcga ccctgacctg gaaactgaga ctatgtgcct           450
ccacgacgac gagtcgtgtc gctacgaagg gcaagtcgct gtttaccagg           500
atgtatacgc ggttgacgga ccgacaagtc tctatcacca agccaataag           550
ggagttagag tcgcctactg gataggcttt gacaccaccc cttttatgtt           600
taagaacttg gctggagcat atccatcata ctctaccaac tgggccgacg           650
aaaccgtgtt aacggctcgt aacataggcc tatgcagctc tgacgttatg           700
gagcggtcac gtagagggat gtccattctt agaaagaagt atttgaaacc           750
atccaacaat gttctattct ctgttggctc gaccatctac cacgagaaga           800
gggacttact gaggagctgg cacctgccgt ctgtatttca cttacgtggc           850
aagcaaaatt acacatgtcg gtgtgagact atagttagtt gcgacgggta           900
cgtcgttaaa agaatagcta tcagtccagg cctgtatggg aagccttcag           950
gctatgctgc tacgatgcac cgcgagggat tcttgtgctg caaagtgaca          1000
gacacattga acggggagag ggtctctttt cccgtgtgca cgtatgtgcc          1050
```

```
agctacattg tgtgaccaaa tgactggcat actggcaaca gatgtcagtg        1100
cggacgacgc gcaaaaactg ctggttgggc tcaaccagcg tatagtcgtc        1150
aacggtcgca cccagagaaa caccaatacc atgaaaaatt accttttgcc        1200
cgtagtggcc caggcatttg ctaggtgggc aaaggaatat aaggaagatc        1250
aagaagatga aaggccacta ggactacgag atagacagtt agtcatgggg        1300
tgttgttggg cttttagaag gcacaagata acatctattt ataagcgccc        1350
ggatacccaa accatcatca aagtgaacag cgatttccac tcattcgtgc        1400
tgcccaggat aggcagtaac acattggaga tcgggctgag aacaagaatc        1450
aggaaaatgt tagaggagca caaggagccg tcacctctca ttaccgccga        1500
ggacgtacaa gaagctaagt gcgcagccga tgaggctaag gaggtgcgtg        1550
aagccgagga gttgcgcgca gctctaccac ctttggcagc tgatgttgag        1600
gagcccactc tggaagccga tgtcgacttg atgttacaag aggctggggc        1650
cggctcagtg gagacacctc gtggcttgat aaaggttacc agctacgatg        1700
gcgaggacaa gatcggctct tacgctgtgc tttctccgca ggctgtactc        1750
aagagtgaaa aattatcttg catccaccct ctcgctgaac aagtcatagt        1800
gataacacac tctggccgaa aagggcgtta tgccgtggaa ccataccatg        1850
gtaaagtagt ggtgccagag ggacatgcaa tacccgtcca ggactttcaa        1900
gctctgagtg aaagtgccac cattgtgtac aacgaacgtg agttcgtaaa        1950
caggtacctg caccatattg ccacacatgg aggagcgctg aacactgatg        2000
aagaatatta caaaactgtc aagcccagcg agcacgacgg cgaataccTg        2050
tacgacatcg acaggaaaca gtgcgtcaag aaagaactag tcactgggct        2100
agggctcaca ggcgagctgg tggatcctcc cttccatgaa ttcgcctacg        2150
agagtctgag aacacgacca gccgctcctt accaagtacc aaccataggg        2200
gtgtatggcg tgccaggatc aggcaagtct ggcatcatta aaagcgcagt        2250
caccaaaaaa gatctagtgg tgagcgccaa gaaagaaaac tgtgcagaaa        2300
ttataaggga cgtcaagaaa atgaaagggc tggacgtcaa tgccagaact        2350
gtggactcag tgctccttga tggatgcaaa caccccgtag agaccctgta        2400
tattgacgaa gcttttgctt gtcatgcagg tactctcaga gcgctcatag        2450
ccattataag acctaaaaag gcagtgctct gcggggatcc caaacagtgc        2500
ggttttttta acatgatgtg cctgaaagtg cattttaacc acgagatttg        2550
cacacaagtc ttccacaaaa gcatctctcg ccgttgcact aaatctgtga        2600
cttcggtcgt ctcaaccttg ttttacgaca aaaaaatgag aacgacgaat        2650
ccgaaagaga ctaagattgt gattgacact accggcagta ccaaacctaa        2700
gcaggacgat ctcattctca cttgtttcag agggtgggtg aagcagttgc        2750
aaatagatta caaggcaac gatatgacgg cagctgcctc tcaagggctg        2800
acccgtaaag gtgtgtatgc cgttcggtac aaggtgaatg aaaatcctct        2850
gtacgcaccc acctcagaac atgtgaacgt cctactgacc cgcacggagg        2900
accgcatcgt gtggaaaaca ctagccggcg acccatggat aaaaacactg        2950
actgccaagt accctgggaa tttcactgcc acgatagagg agtggcaagc        3000
agagcatgat gccatcatga ggcacatctt ggagagaccg gaccctaccg        3050
```

```
acgtcttcca gaataaggca aacgtgtgtt gggccaaggc tttagtgccg      3100
gtgctgaaga ccgctggcat agacatgacc actgaacaat ggaacactgt      3150
ggattatttt gaaacggaca aagctcactc agcagagata gtattgaacc      3200
aactatgcgt gaggttcttt ggactcgatc tggactccgg tctatttcct      3250
gcacccactg ttccgttatc cattaggaat aatcactggg ataactcccc      3300
gtcgcctaac atgtacgggc tgaataaaga agtggtccgt cagctctctc      3350
gcaggtaccc acaactgcct cgggcagttg ccactggaag agtctatgac      3400
atgaacactg gtacactgcg caattatgat ccgcgcataa acctagtacc      3450
tgtaaacaga agactgcctc atgctttagt cctccaccat aatgaacacc      3500
cacagagtga cttttcttca ttcgtcagca aattgaaggg cagaactgtc      3550
ctggtggtcg gggaaaagtt gtccgtccca ggcaaaatgg ttgactggtt      3600
gtcagaccgg cctgaggcta ccttcagagc tcggctggat ttaggcatcc      3650
caggtgatgt gcccaaatat gacataatat tgttaatgt gaggacccca      3700
tataaatacc atcactatca gcagtgtgaa gaccatgcca ttaagcttag      3750
catgttgacc aagaaagctt gtctgcatct gaatcccggc ggaacctgtg      3800
tcagcatagg ttatggttac gctgacaggg ccagcgaaag catcattggt      3850
gctatagcgc ggcagttcaa gttttcccgg gtatgcaaac cgaaatcctc      3900
acttgaagag acggaagttc tgtttgtatt cattgggtac gatcgcaagg      3950
cccgtacgca caatccttac aagctttcat caaccttgac caacatttat      4000
acaggttcca gactccacga agccggatgt gcaccctcat atcatgtggt      4050
gcgagggat attgccacgg ccaccgaagg agtgattata aatgctgcta       4100
acagcaaagg acaacctggc ggaggggtgt gcggagcgct gtataagaaa      4150
ttcccggaaa gcttcgattt acagccgatc gaagtaggaa aagcgcgact      4200
ggtcaaaggt gcagctaaac atatcattca tgccgtagga ccaaacttca      4250
acaaagtttc ggaggttgaa ggtgacaaac agttggcaga ggcttatgag      4300
tccatcgcta agattgtcaa cgataacaat tacaagtcag tagcgattcc      4350
actgttgtcc accggcatct tttccgggaa caaagatcga ctaacccaat      4400
cattgaacca tttgctgaca gctttagaca ccactgatgc agatgtagcc      4450
atatactgca gggacaagaa atgggaaatg actctcaagg aagcagtggc      4500
taggagagaa gcagtggagg agatatgcat atccgacgac tcttcagtga      4550
cagaacctga tgcagagctg gtgagggtgc atccgaagag ttctttggct      4600
ggaaggaagg gctacagcac aagcgatggc aaaactttct catatttgga      4650
agggaccaag tttcaccagg cggccaagga tatagcagaa attaatgcca      4700
tgtggccgt tgcaacggag gccaatgagc aggtatgcat gtatatcctc       4750
ggagaaagca tgagcagtat taggtcgaaa tgccccgtcg aagagtcgga      4800
agcctccaca ccacctagca cgctgccttg cttgtgcatc catgccatga      4850
ctccagaaag agtacagcgc ctaaaagcct cacgtccaga acaaattact      4900
gtgtgctcat ccttttccatt gccgaagtat agaatcactg gtgtgcagaa      4950
gatccaatgc tccagccta tattgttctc accgaaagtg cctgcgtata       5000
ttcatccaag gaagtatctc gtggaaacac caccggtaga cgagactccg      5050
```

```
gagccatcgg cagagaacca atccacagag gggacacctg aacaaccacc      5100
acttataacc gaggatgaga ccaggactag aacgcctgag ccgatcatca      5150
tcgaagagga agaagaggat agcataagtt tgctgtcaga tggcccgacc      5200
caccaggtgc tgcaagtcga ggcagacatt cacgggccgc cctctgtatc      5250
tagctcatcc tggtccattc ctcatgcatc cgactttgat gtggacagtt      5300
tatccatact tgacaccctg gagggagcta gcgtgaccag cggggcaacg      5350
tcagccgaga ctaactctta cttcgcaaag agtatggagt ttctggcgcg      5400
accggtgcct gcgcctcgaa cagtattcag gaaccctcca catcccgctc      5450
cgcgcacaag aacaccgtca cttgcaccca gcagggcctg ctcgagaacc      5500
agcctagttt ccaccccgcc aggcgtgaat agggtgatca ctagagagga      5550
gctcgaggcg cttaccccgt cacgcactcc tagcaggtcg gtctcgagaa      5600
ccagctggtc tccaacccgc caggcgtaaa tagggtgatt acaagagagg      5650
agtttgaggc gttcgtagca caacaacaat gacggtttga tgcgggtgca      5700
tacatctttt cctccgacac cggtcaaggg catttacaac aaaaatcagt      5750
aaggcaaacg gtgctatccg aagtggtgtt ggagaggacc gaattggaga      5800
tttcgtatgc cccgcgcctc gaccaagaaa aagaagaatt actacgcaag      5850
aaattacagt taaatcccac acctgctaac agaagcagat accagtccag      5900
gaaggtggag aacatgaaag ccataacagc tagacgtatt ctgcaaggcc      5950
tagggcatta tttgaaggca gaaggaaaag tggagtgcta ccgaaccctg      6000
catcctgttc ctttgtattc atctagtgtg aaccgtgcct tttcaagccc      6050
caaggtcgca gtggaagcct gtaacgccat gttgaaagag aactttccga      6100
ctgtggcttc ttactgtatt attccagagt acgatgccta tttggacatg      6150
gttgacggag cttcatgctg cttagacact gccagttttt gccctgcaaa      6200
gctgcgcagc tttccaaaga aacactccta tttggaaccc acaatacgat      6250
cggcagtgcc ttcagcgatc cagaacacgc tccagaacgt cctggcagct      6300
gccacaaaaa gaaattgcaa tgtcacgcaa atgagagaat tgcccgtatt      6350
ggattcggcg gcctttaatg tggaatgctt caagaaatat gcgtgtaata      6400
atgaatattg ggaaacgttt aaagaaaacc ccatcaggct tactgaagaa      6450
aacgtggtaa attacattac caaattaaaa ggaccaaaag ctgctgctct      6500
ttttgcgaag acacataatt tgaatatgtt gcaggacata ccaatggaca      6550
ggtttgtaat ggacttaaag agagacgtga aagtgactcc aggaacaaaa      6600
catactgaag aacggcccaa ggtacaggtg atccaggctg ccgatccgct      6650
agcaacagcg tatctgtgcg gaatccaccg agagctggtt aggagattaa      6700
atgcggtcct gcttccgaac attcatacac tgtttgatat gtcggctgaa      6750
gactttgacg ctattatagc cgagcacttc cagcctgggg attgtgttct      6800
ggaaactgac atcgcgtcgt ttgataaaag tgaggacgac gccatggctc      6850
tgaccgcgtt aatgattctg gaagacttag gtgtggacgc agagctgttg      6900
acgctgattg aggcggcttt cggcgaaatt tcatcaatac atttgcccac      6950
taaaactaaa tttaaattcg gagccatgat gaaatctgga atgttcctca      7000
cactgtttgt gaacacagtc attaacattg taatcgcaag cagagtgttg      7050
```

```
agagaacggc taaccggatc accatgtgca gcattcattg gagatgacaa      7100
tatcgtgaaa ggagtcaaat cggacaaatt aatggcagac aggtgcgcca      7150
cctggttgaa tatggaagtc aagattatag atgctgtggt gggcgagaaa      7200
gcgccttatt tctgtggagg gtttattttg tgtgactccg tgaccggcac      7250
agcgtgccgt gtggcagacc ccctaaaaag gctgtttaag cttggcaaac      7300
ctctggcaga gacgatgaa catgatgatg acaggagaag ggcattgcat       7350
gaagagtcaa cacgctggaa ccgagtgggt attctttcag agctgtgcaa      7400
ggcagtagaa tcaaggtatg aaaccgtagg aacttccatc atagttatgg      7450
ccatgactac tctagctagc agtgttaaat cattcagcta cctgagaggg      7500
gcccctataa ctctctacgg ctaacctgaa tggactacga catagtctag      7550
tccgccaagt ctagaccatg agcggccgga aggctcaggg caagaccctg      7600
ggcgtgaaca tggtgaggcg cggcgtgcgc agcctctcca acaagatcaa      7650
gcagaagacc aagcagatcg gcaacagacc cggaccgagc cggggcgtcc      7700
aggggttcat cttcttcttc ctgttcaaca tcctcacagg taagaagatc      7750
acggctcacc tgaagaggct ctggaagatg ctggaccctc gccaggggct      7800
cgcggtgctc agaaaggtga agcgggtcgt cgcctccctg atgcgcggcc      7850
tgtcctctcg caagaggcgc tcccacgatg tgctcaccgt ccaattcctc      7900
attctgggaa tgctgttgat gacggtgga gtgaccttgg tgcggaaaaa       7950
cagatggttg ctcctaaatg tgacatctga ggacctcggg aaaacattct      8000
ctgtgggcac aggcaactgc acaacaaaca ttttggaagc caagtactgg      8050
tgcccagact caatggaata caactgtccc aatctcagtc aagagagga      8100
gccagatgac attgattgct ggtgctatgg ggtggaaaac gttagagtcg      8150
catatggtaa gtgtgactca gcaggcaggt ctaggaggtc aagaagggcc      8200
attgacttgc ctacgcatga aaaccatggt ttgaagaccc ggcaagaaaa      8250
atggatgact ggaagaatgg gtgaaaggca actccaaaag attgagagat      8300
ggttcgtgag gaacccgttt tttgcagtga cggctctgac cattgcctac      8350
cttgtgggaa gcaacatgac gcaacgagtc gtgattgccc tactggtctt      8400
ggctgttggt ccggcctact cagctcactg cattggaatt actgacaggg      8450
atttcattga gggggtgcat ggaggaactt gggtttcagc taccctggag      8500
caagacaagt gtgtcactgt tatggcccct gacaagcctt cattggacat      8550
ctcactagag acagtagcca ttgatagacc tgctgaggtg aggaaagtgt      8600
gttacaatgc agttctcact catgtgaaga ttaatgacaa gtgccccagc      8650
actggagagg cccacctagc tgaagagaac gaagggaca atgcgtgcaa       8700
gcgcacttat tctgatagag gctggggcaa tggctgtggc ctatttggga      8750
aagggagcat tgtggcatgc gccaaattca cttgtgccaa atccatgagt      8800
ttgtttgagg ttgatcagac caaaattcag tatgtcatca gagcacaatt      8850
gcatgtaggg gccaagcagg aaaattggaa taccgacatt aagactctca      8900
agtttgatgc cctgtcaggc tcccaggaag tcgagttcat tgggtatgga      8950
aaagctacac tggaatgcca ggtgcaaact gcggtggact tggtaacag       9000
ttacatcgct gagatggaaa cagagagctg gatagtggac agacagtggg      9050
```

-continued

```
cccaggactt gaccctgcca tggcagagtg gaagtggcgg ggtgtggaga      9100
gagatgcatc atcttgtcga atttgaacct ccgcatgccg ccactatcag      9150
agtactggcc ctgggaaacc aggaaggctc cttgaaaaca gctcttactg      9200
gcgcaatgag ggttacaaag gacacaaatg acaacaacct ttacaaacta      9250
catggtggac atgtttcttg cagagtgaaa ttgtcagctt tgacactcaa      9300
ggggacatcc tacaaaatat gcactgacaa aatgttttttt gtcaagaacc     9350
caactgacac tggccatggc actgttgtga tgcaggtgaa agtgtcaaaa      9400
ggagccccct gcaggattcc agtgatagta gctgatgatc ttacagcggc      9450
aatcaataaa ggcattttgg ttacagttaa ccccatcgcc tcaaccaatg      9500
atgatgaagt gctgattgag gtgaacccac cttttggaga cagctacatt      9550
atcgttggga gaggagattc acgtctcact taccagtggc acaaagaggg      9600
aagctcaata ggaaagttgt tcactcagac catgaaaggc gtggaacgcc      9650
tggccgtcat gggagacacc gcctgggatt tcagctccgc tggagggttc      9700
ttcacttcgg ttgggaaagg aattcatacg gtgtttggct ctgcctttca      9750
ggggctattt ggcggcttga actggataac aaaggtcatc atggggcgg      9800
tacttatatg ggttggcatc aacacaagaa acatgacaat gtccatgagc      9850
atgatcttgg taggagtgat catgatgttt ttgtctctag gagttggggc      9900
gtaagcggcc cctataactc tctacggcta acctgaatgg actacgacat      9950
agtctagtcc gccaagtcta gagcttacca tgaccgagta caagcccacg      10000
gtgcgcctcg ccacccgcga cgacgtcccc agggccgtac gcaccctcgc      10050
cgccgcgttc gccgactacc ccgccacgcg ccacaccgtc gatccggacc      10100
gccacatcga gcgggtcacc gagctgcaag aactcttcct cacgcgcgtc      10150
gggctcgaca tcggcaaggt gtgggtcgcg gacgacggcg ccgcggtggc      10200
ggtctggacc acgccggaga gcgtcgaagc ggggcggtg ttcgccgaga      10250
tcggcccgcg catggccgag ttgagcggtt cccggctggc cgcgcagcaa      10300
cagatggaag gcctcctggc gccgcaccgg cccaaggagc ccgcgtggtt      10350
cctggccacc gtcggcgtct cgcccgacca ccagggcaag ggtctgggca      10400
gcgccgtcgt gctccccgga gtggaggcgg ccgagcgcgc cggggtgccc      10450
gccttcctgg agacctccgc gccccgcaac ctccccttct acgagcggct      10500
cggcttcacc gtcaccgccg acgtcgaggt gcccgaagga ccgcgcacct      10550
gatgcatgac ccgcaagccc ggtgcctgac gcccgcccca cgacccgcag      10600
cgcccgaccg aaaggagcgc acgaccccat gatcgctaga ccatggggta      10650
ccgagtatgt tacgtgcaaa ggtgattgtc accccccgaa agaccatatt      10700
gtgacacacc ctcagtatca cgcccaaaca tttacagccg cggtgtcaaa      10750
aaccgcgtgg acgtggttaa catccctgct gggaggatca gccgtaatta      10800
ttataattgg cttggtgctg gctactattg tggccatgta cgtgctgacc      10850
aaccagaaac ataattgaat acagcagcaa ttggcaagct gcttacatag      10900
aactcgcggc gattgcatgc cgccttaaaa ttttttatttt attttttctt     10950
ttcttttccg aatcggattt tgttttttaat atttcaaaaa aaaaaaaaaa      11000
aaaaaaaaaa cgcgtcgagg ggaattaatt cttgaagacg aaagggccag     11050
```

-continued

| | |
|---|---|
| gtggcacttt tcggggaaat gtgcgcggaa cccctatttg tttatttttc | 11100 |
| taaatacatt caaatatgta tccgctcatg agacaataac cctgataaat | 11150 |
| gcttcaataa tattgaaaaa ggaagagtat gagtattcaa catttccgtg | 11200 |
| tcgcccttat tccctttttt gcggcatttt gccttcctgt ttttgctcac | 11250 |
| ccagaaacgc tggtgaaagt aaaagatgct gaagatcagt tgggtgcacg | 11300 |
| agtgggttac atcgaactgg atctcaacag cggtaagatc cttgagagtt | 11350 |
| ttcgccccga agaacgtttt ccaatgatga gcacttttaa agttctgcta | 11400 |
| tgtggcgcgg tattatcccg tgttgacgcc gggcaagagc aactcggtcg | 11450 |
| ccgcatacac tattctcaga atgacttggt tgagtactca ccagtcacag | 11500 |
| aaaagcatct tacggatggc atgacagtaa gagaattatg cagtgctgcc | 11550 |
| ataaccatga gtgataacac tgcggccaac ttacttctga caacgatcgg | 11600 |
| aggaccgaag gagctaaccg cttttttgca caacatgggg gatcatgtaa | 11650 |
| ctcgccttga tcgttgggaa ccggagctga atgaagccat accaaacgac | 11700 |
| gagcgtgaca ccacgatgcc tgtagcaatg gcaacaacgt tgcgcaaact | 11750 |
| attaactggc gaactactta ctctagcttc ccggcaacaa ttaatagact | 11800 |
| ggatggaggc ggataaagtt gcaggaccac ttctgcgctc ggcccttccg | 11850 |
| gctggctggt ttattgctga taaatctgga gccggtgagc gtgggtctcg | 11900 |
| cggtatcatt gcagcactgg ggccagatgg taagccctcc cgtatcgtag | 11950 |
| ttatctacac gacggggagt caggcaacta tggatgaacg aaatagacag | 12000 |
| atcgctgaga taggtgcctc actgattaag cattggtaac tgtcagacca | 12050 |
| agtttactca tatatacttt agattgattt aaaacttcat ttttaattta | 12100 |
| aaaggatcta ggtgaagatc ctttttgata atctcatgac caaaatccct | 12150 |
| taacgtgagt tttcgttcca ctgagcgtca gaccccgtag aaaagatcaa | 12200 |
| aggatcttct tgagatcctt ttttctgcg cgtaatctgc tgcttgcaaa | 12250 |
| caaaaaaacc accgctacca gcggtggttt gtttgccgga tcaagagcta | 12300 |
| ccaactcttt ttccgaaggt aactggcttc agcagagcgc agataccaaa | 12350 |
| tactgtcctt ctagtgtagc cgtagttagg ccaccacttc aagaactctg | 12400 |
| tagcaccgcc tacatacctc gctctgctaa tcctgttacc agtggctgct | 12450 |
| gccagtggcg ataagtcgtg tcttaccggg ttggactcaa gacgatagtt | 12500 |
| accggataag gcgcagcggt cgggctgaac ggggggttcg tgcacacagc | 12550 |
| ccagcttgga gcgaacgacc tacaccgaac tgagatacct acagcgtgag | 12600 |
| cattgagaaa gcgccacgct tcccgaaggg agaaaggcgg acaggtatcc | 12650 |
| ggtaagcggc agggtcggaa caggagagcg cacgagggag cttccagggg | 12700 |
| gaaacgcctg gtatctttat agtcctgtcg ggtttcgcca cctctgactt | 12750 |
| gagcgtcgat ttttgtgatg ctcgtcaggg gggcggagcc tatggaaaaa | 12800 |
| cgccagcaac gcgagctcga tttaggtgac actata | 12836 |

<210> SEQ ID NO 12
<211> LENGTH: 93
<212> TYPE: RNA
<213> ORGANISM: artificial sequence
<220> FEATURE:
<223> OTHER INFORMATION: partial sequence of the C gene of VEE replicon

<400> SEQUENCE: 12
augagcaaaa agccuggugg accuggaaaa uccagagcag ugaacauguu          50
gaagagaggc augccaaggg uccucagucu gaucggccuu aag                 93

<210> SEQ ID NO 13
<211> LENGTH: 21
<212> TYPE: RNA
<213> ORGANISM: artificial sequence
<220> FEATURE:
<223> OTHER INFORMATION: partial sequence of the C gene of VEE replicon

<400> SEQUENCE: 13
ucaaaacaaa agaaaagaua a                                         21

<210> SEQ ID NO 14
<211> LENGTH: 31
<212> TYPE: PRT
<213> ORGANISM: artificial sequence
<220> FEATURE:
<223> OTHER INFORMATION: partial amino acid sequence of the C gene of
      VEE replicon

<400> SEQUENCE: 14

Met Ser Lys Lys Pro Gly Gly Pro Gly Lys Ser Arg Ala Val Asn
                 5                  10                  15

Met Leu Lys Arg Gly Met Pro Arg Val Leu Ser Leu Ile Gly Leu
             20                  25                  30

Lys

<210> SEQ ID NO 15
<211> LENGTH: 6
<212> TYPE: PRT
<213> ORGANISM: artificial sequence
<220> FEATURE:
<223> OTHER INFORMATION: partial amino acid sequence of the C gene of
      VEE replicon

<400> SEQUENCE: 15

Ser Lys Gln Lys Lys Arg
                 5

<210> SEQ ID NO 16
<211> LENGTH: 90
<212> TYPE: RNA
<213> ORGANISM: artificial sequence
<220> FEATURE:
<223> OTHER INFORMATION: sequence of the West Nile RepliVax genome
      that overlaps with sequence of VEErep

<400> SEQUENCE: 16
augucuaaga aaccaggagg gcccggcaag agccgggcug ucaauaugcu          50
aaaacgcgga augccccgcg uguguccuu gauuggacuu                      90

<210> SEQ ID NO 17
<211> LENGTH: 33
<212> TYPE: PRT
<213> ORGANISM: artificial sequence
<220> FEATURE:
<223> OTHER INFORMATION: sequence of the West Nile RepliVax genome
      that overlaps with sequence of VEErep

<400> SEQUENCE: 17

Met Ser Lys Lys Pro Gly Gly Pro Gly Gly Pro Gly Lys Ser Arg
                 5                  10                  15

```
Ala Val Asn Met Leu Lys Arg Gly Met Pro Arg Val Leu Ser Leu
            20                  25                  30

Ile Gly Leu

<210> SEQ ID NO 18
<211> LENGTH: 18
<212> TYPE: RNA
<213> ORGANISM: artificial sequence
<220> FEATURE:
<223> OTHER INFORMATION: sequence of the West Nile RepliVax genome
      overlaps with sequence of VEErep

<400> SEQUENCE: 18
aagcaaaaga aaagagga                                                 18

<210> SEQ ID NO 19
<211> LENGTH: 6
<212> TYPE: PRT
<213> ORGANISM: artificial sequence
<220> FEATURE:
<223> OTHER INFORMATION: sequence of the West Nile RepliVax genome
      overlaps with sequence of VEErep

<400> SEQUENCE: 19

Lys Gln Lys Lys Arg Gly
                5

<210> SEQ ID NO 20
<211> LENGTH: 11
<212> TYPE: RNA
<213> ORGANISM: artificial sequence
<220> FEATURE:
<223> OTHER INFORMATION: sequence of cyclization mutant 7

<400> SEQUENCE: 20
cucaauaugc u                                                        11

<210> SEQ ID NO 21
<211> LENGTH: 11
<212> TYPE: RNA
<213> ORGANISM: artificial sequence
<220> FEATURE:
<223> OTHER INFORMATION: sequence of cyclization mutant 8

<400> SEQUENCE: 21
gacaauaugc u                                                        11

<210> SEQ ID NO 22
<211> LENGTH: 11
<212> TYPE: RNA
<213> ORGANISM: artificial sequence
<220> FEATURE:
<223> OTHER INFORMATION: sequence of cyclization mutant 9

<400> SEQUENCE: 22
gugaauaugc u                                                        11

<210> SEQ ID NO 23
<211> LENGTH: 11
<212> TYPE: RNA
<213> ORGANISM: artificial sequence
<220> FEATURE:
<223> OTHER INFORMATION: sequence of cyclization mutant 10

<400> SEQUENCE: 23
gucuauaugc u                                                        11
```

```
<210> SEQ ID NO 24
<211> LENGTH: 11
<212> TYPE: RNA
<213> ORGANISM: artificial sequence
<220> FEATURE:
<223> OTHER INFORMATION: sequence of cyclization mutant 11

<400> SEQUENCE: 24
gucauuaugc u                                                          11

<210> SEQ ID NO 25
<211> LENGTH: 11
<212> TYPE: RNA
<213> ORGANISM: artificial sequence
<220> FEATURE:
<223> OTHER INFORMATION: sequence of cyclization mutant 12

<400> SEQUENCE: 25
gucaaaaugc u                                                          11

<210> SEQ ID NO 26
<211> LENGTH: 11
<212> TYPE: RNA
<213> ORGANISM: artificial sequence
<220> FEATURE:
<223> OTHER INFORMATION: sequence of cyclization mutant 13

<400> SEQUENCE: 26
gucaauuugc u                                                          11

<210> SEQ ID NO 27
<211> LENGTH: 11
<212> TYPE: RNA
<213> ORGANISM: artificial sequence
<220> FEATURE:
<223> OTHER INFORMATION: sequence of cyclization mutant 14

<400> SEQUENCE: 27
gucaauaucc u                                                          11

<210> SEQ ID NO 28
<211> LENGTH: 11
<212> TYPE: RNA
<213> ORGANISM: artificial sequence
<220> FEATURE:
<223> OTHER INFORMATION: sequence of cyclization mutant 15

<400> SEQUENCE: 28
gucaauaugg u                                                          11

<210> SEQ ID NO 29
<211> LENGTH: 11
<212> TYPE: RNA
<213> ORGANISM: artificial sequence
<220> FEATURE:
<223> OTHER INFORMATION: sequence of cyclization mutant 16

<400> SEQUENCE: 29
gucaauaugc a                                                          11

<210> SEQ ID NO 30
<211> LENGTH: 11
<212> TYPE: RNA
<213> ORGANISM: artificial sequence
<220> FEATURE:
<223> OTHER INFORMATION: wild type cyclization signal sequence
```

```
<400> SEQUENCE: 30
agcauauuga c                                                        11

<210> SEQ ID NO 31
<211> LENGTH: 11
<212> TYPE: RNA
<213> ORGANISM: artificial sequence
<220> FEATURE:
<223> OTHER INFORMATION: sequence of cyclization mutant 7

<400> SEQUENCE: 31
agcauauuga g                                                        11

<210> SEQ ID NO 32
<211> LENGTH: 11
<212> TYPE: RNA
<213> ORGANISM: artificial sequence
<220> FEATURE:
<223> OTHER INFORMATION: sequence of cyclization mutant 8

<400> SEQUENCE: 32
agcauauugu c                                                        11

<210> SEQ ID NO 33
<211> LENGTH: 11
<212> TYPE: RNA
<213> ORGANISM: artificial sequence
<220> FEATURE:
<223> OTHER INFORMATION: sequence of cyclization mutant 9

<400> SEQUENCE: 33
agcauauuca c                                                        11

<210> SEQ ID NO 34
<211> LENGTH: 11
<212> TYPE: RNA
<213> ORGANISM: artificial sequence
<220> FEATURE:
<223> OTHER INFORMATION: sequence of cyclization mutant 10

<400> SEQUENCE: 34
agcauauaga c                                                        11

<210> SEQ ID NO 35
<211> LENGTH: 11
<212> TYPE: RNA
<213> ORGANISM: artificial sequence
<220> FEATURE:
<223> OTHER INFORMATION: sequence of cyclization mutant 11

<400> SEQUENCE: 35
agcauaauga c                                                        11

<210> SEQ ID NO 36
<211> LENGTH: 11
<212> TYPE: RNA
<213> ORGANISM: artificial sequence
<220> FEATURE:
<223> OTHER INFORMATION: sequence of cyclization mutant 12

<400> SEQUENCE: 36
agcauuuuga c                                                        11

<210> SEQ ID NO 37
<211> LENGTH: 11
<212> TYPE: RNA
```

-continued

```
<213> ORGANISM: artificial sequence
<220> FEATURE:
<223> OTHER INFORMATION: sequence of cyclization mutant 13

<400> SEQUENCE: 37
agcaaauuga c                                                          11

<210> SEQ ID NO 38
<211> LENGTH: 11
<212> TYPE: RNA
<213> ORGANISM: artificial sequence
<220> FEATURE:
<223> OTHER INFORMATION: sequence of cyclization mutant 14

<400> SEQUENCE: 38
aggauauuga c                                                          11

<210> SEQ ID NO 39
<211> LENGTH: 11
<212> TYPE: RNA
<213> ORGANISM: artificial sequence
<220> FEATURE:
<223> OTHER INFORMATION: sequence of cyclization mutant 15

<400> SEQUENCE: 39
accauauuga c                                                          11

<210> SEQ ID NO 40
<211> LENGTH: 11
<212> TYPE: RNA
<213> ORGANISM: artificial sequence
<220> FEATURE:
<223> OTHER INFORMATION: sequence of cyclization mutant 16

<400> SEQUENCE: 40
ugcauauuga c                                                          11

<210> SEQ ID NO 41
<211> LENGTH: 11
<212> TYPE: RNA
<213> ORGANISM: artificial sequence
<220> FEATURE:
<223> OTHER INFORMATION: sequence of cyclization mutant 17

<400> SEQUENCE: 41
gucuauuugc u                                                          11

<210> SEQ ID NO 42
<211> LENGTH: 11
<212> TYPE: RNA
<213> ORGANISM: artificial sequence
<220> FEATURE:
<223> OTHER INFORMATION: sequence of cyclization mutant 17

<400> SEQUENCE: 42
agcaaauaga c                                                          11
```

PSEUDOINFECTIOUS *FLAVIVIRUS* AND USES THEREOF

CROSS REFERENCE TO RELATED APPLICATION

This non-provisional application claims benefit of provisional application U.S. Ser. No. 60/777,189 filed on Feb. 27, 2006, now abandoned.

FEDERAL FUNDING LEGEND

This invention was produced in part using funds obtained through National Institute of Health grants (R01AI053135 and 1U54AI057156-010004). Consequently, the federal government has certain rights in this invention.

BACKGROUND OF THE INVENTION

1. Field of the Invention

The present invention relates to the fields of molecular biology, virology and immunology. In general, the present invention discloses construction of replication-deficient viruses belonging to the Flaviviridae family and their use as vaccine in prevention of diseases caused by viruses belonging to this family. More specifically, the present invention provides replication-deficient flaviviruses or pseudoinfectious flaviviruses (PIV aka RepliVAX) and discloses its use as preventive vaccines against flavivirus-associated diseases.

2. Description of the Related Art

The Flavivirus genus of the Flaviviridae family contains a variety of important human and animal pathogens and have been classified into four distinct antigenic complexes based on differences in reactivity in immunological tests. Generally, the flaviviruses circulate between avian or mammalian amplifying hosts and mosquito or tick vectors.

The flavivirus genome is a single-stranded capped RNA of positive polarity lacking a 3' terminal poly(A) sequence. It encodes a single polypeptide that is co- and post-translationally processed into viral structural proteins, C, prM/M, and E, forming viral particles, and the nonstructural proteins, NS1, NS2A, NS2B, NS3, NS4A, NS4B and NS5, required for replication of viral genome and its packaging into infectious virions (Chambers, 1990). Virions contain a single copy of viral genomic RNA packaged into a C protein-containing nucleocapsid, surrounded by lipid envelope holding heterodimers of M and E proteins. In contrast to many other enveloped viruses, interaction between nucleocapsid and envelope spikes is not very specific and M/E-containing envelope can efficiently form around nucleocapsid derived from heterologous flavivirus, demonstrating limited level of homology in capsid sequence (Lorenz, 2002). Alternatively, expression of prM and E in the absence of C can lead to formation of subviral particles (SVPs), containing no RNA or C protein (Mason, 1991).

PrM/M-E cassettes producing subviral particles have been the basis of several vaccine candidates that are known in the art. These vaccine candidates include subunit (Konishi, 1992; 2001; 2002; Qiao, 2004), DNA (Phillpotts, 1996; Kochel, 1997; Schmaljohn, 1997; Colombage, 1998; Aberle, 1999; Konishi, 2000; Konishi, 2000; Kochel, 2000; Davis, 2001), and live-vectored (Mason, 1991; Konishi, 1992; Pincus, 1992; Fonseca, 1994; Pugachev, 1995; Colombage, 1998; Kanesa, 2000; Minke, 2004) vaccines. However, these vaccines have serious disadvantages. For instance, the subunit vaccines are safe to use but difficult to produce large quantities; the DNA vaccines are poorly immunogenic, and the viral vectored vaccines suffer from lack of potency in the presence of vector immunity.

Therefore, in spite of a great concern about flavivirus-associated diseases and continuing spread of the flaviviruses into the new areas, antiviral therapeutics have not yet been developed for these infections, and a very limited number of approved vaccines have been produced to-date. Inactivated viral vaccines (INVs) have been licensed to prevent tick-borne encephalitis (TBEV) and Japanese encephalitis (JEV). However, like other inactivated viral vaccines, these vaccines have low limited potency and require multiple vaccinations. Despite these drawbacks the Japanese encephalitis and tick-borne encephalitis INVs have an advantage of good safety records. The only licensed live-attenuated vaccine (LAV) for a flavivirus is the widely utilized live-attenuated vaccine based on the yellow fever virus (YFV) 17D strain that was developed by serial passaging of the wild type Asibi strain of yellow fever virus in chicken embryo tissues. Although this live-attenuated vaccine is considered very safe and effective, cases of yellow fever in vaccinees have been reported, including a recent case in a US military recruit (Gerasimon, 2005). Furthermore, this vaccine is not recommended for use in infants, pregnant women or the immunocompromised individuals due to adverse effects, including vaccine-associated encephalitis.

However, the development of the reverse genetics systems for flaviviruses has led to the production and designing of new types of live-attenuated vaccine, based on rational attenuation of these viruses. This new class of vaccines includes yellow fever virus 17D-based chimeras, in which the yellow fever virus prM-E-encoding genome fragment cassette has been replaced with the prM-E-cassette derived from heterologous flaviviruses (Chambers, 1999). Similar chimeric virus-based approach was applied for dengue- and TBE-based backbones (Pletnev, 2002; Huang, 2003). In most cases, chimeric flaviviruses demonstrate a highly attenuated phenotype and are capable of eliciting efficient protective immune response and protect against following infection with viruses, whose structural proteins are expressed by the chimeras (Monath, 2002). Effective vaccination with these chimeric vaccine candidates appears not to be prevented by pre-existing "vector" immunity (Monath, 2002), which has interfered with potency of recombinant viral vaccines based on other viral vectors. Further, although chimeric flaviviruses might provide a reasonably universal approach to producing new vaccines, there are concerns that the chimeras themselves might be pathogenic (Chambers, 1999) at least in the immunocompromised individuals, or that pathogenic chimeras might arise, since mutations have been detected during the process of propagation of these viruses (Pugachev, 2004).

Another promising direction in vaccine development is based on creating of irreparable deletions in flavivirus genome that make productive virus replication in the vaccinated host either a less efficient or an impossible event. In the latter case, viral genomes encoding the entire replicative machinery, but lacking, for instance, the C-coding region, can be delivered for in vivo immunization either as in vitro-synthesized RNA, capable of self-replication (Kofler, 2004; Aberle, 2005), or, probably, in DNA form (under control of the RNA polymerase II promoters or as in vitro-synthesized RNA, capable of self-replication (Kofler, 2004; Aberle, 2005). Direct immunization with in vitro synthesized defective RNA genomes, which specifies the production of SVPs in the absence of a complete viral replication cycle, has been demonstrated to be safe and effective in producing protective immunity (Kofler, 2004; Aberle, 2005). However, there may be significant obstacles in producing an RNA-based vaccine candidate, due to synthesis, stability, and delivery issues.

Thus, prior art is deficient is deficient in a safe, potent and effective type of vaccine that can be used against diseases caused by infection with viruses belonging to the Flaviviridae family. The present invention fulfills this long-standing need and desire in the art.

SUMMARY OF THE INVENTION

In one embodiment of the present invention, there is provided a replication-deficient pseudoinfectious virus of Flaviviridae family. Such a replication-deficient pseudoinfectious virus comprises: a deletion in the nucleotide sequence encoding capsid (C) protein such that the deletion does not disrupt the RNA sequence required for genome cyclization, the signal sequence for prM protein that is required for the proper maturation of prM/M or a combination thereof, where the replication-deficient pseudoinfectious virus replicates only in cells expressing C protein or C, prM, envelope protein, mutated C protein, mutated prM, mutated envelope protein or combinations thereof of the virus of the Flaviviridae family.

In another related embodiment of the present invention, there is provided a cell culture system expressing C protein or C, prM, envelope protein, mutated C protein, mutated prM, mutated envelope protein or combinations thereof of the virus of the Flaviviridae family effective to enable propagation of the above-described replication-deficient pseudoinfectious virus of the Flaviviridae family under suitable conditions.

In yet another embodiment of the present invention, there is provided a method of producing the replication-deficient pseudoinfectious virus of the Flaviviridae family described above. Such a method comprises generating a replication-deficient pseudoinfectious virus of the Flaviviridae family that comprises deletion in the capsid gene such that the deletion does not disrupt the RNA sequence required for genome cyclization, the signal sequence for prM protein that is required for the proper maturation of prM/M or a combination thereof; generating a cell line that expresses C protein or C, prM, envelope protein, mutated C protein, mutated prM, mutated envelope protein or combinations thereof of the virus of the Flaviviridae family, where the cell line provides high levels of the proteins of the Flaviviridae needed for propagation of the replication-deficient pseudoinfectious virus of the Flaviviridae family; and infecting the cell line with the pseudoinfectious virus of the Flaviviridae family, thereby producing the replication-deficient pseudoinfectious virus of the Flaviviridae family.

In another related embodiment of the present invention, there is provided a pharmaceutical composition, comprising the replication-deficient pseudoinfectious virus of the Flaviviridae family produced by the method described herein.

In a further related embodiment of the present invention, there is provided a method of protecting a subject from infections resulting from exposure to Flaviviridae. Such a method comprises administering to the subject an immunologically effective amount of the pharmaceutical composition produced by the method described herein, that elicits an immune response against the Flaviviridae in the subject, thereby protecting the subject from the infections.

BRIEF DESCRIPTION OF THE DRAWINGS

FIG. 1 is a schematic representation of flavivirus PIV replication in the cells producing C or all of the viral structural proteins for trans-complementation of the defect. Replication of PIVs in normal cells in vivo or in vitro leads to release SVPs having no nucleocapsid.

FIGS. 2A-2C show that YFV C and YFV C, prM and E-expressing cell lines can complement replication of YF PIV. FIG. 2A is a schematic representation of YFV and GFP-expressing YF PIV genome. FIG. 2B is a schematic representation of VEEV replicons expressing Pac gene and YFV C with the signal peptide of prM (anchored C; VEErep/C1/Pac), or anchored C with 20 a. a. of prM (VEErep/C2/Pac), or all of the YFV structural proteins (VEErep/C-prM-E/Pac). FIG. 2C shows the release of YF PIV by the cell lines transfected with in vitro-synthesized PIV genome. Media was replaced at the indicated time points, and titers of PIVs were determined. Arrows indicate time points when cells were subpassaged at a 1:5 ratio.

FIG. 3A shows growth curve at MOI 10 inf.u/cell and FIG. 3B shows growth curve at MOI 0.1 inf.u/cell.

FIGS. 4A-4C show that cells expressing codon-optimized C gene produced YF PIV. FIG. 4A shows the nucleotide sequence of synthetic gene. The introduced mutations are indicated by lowercase letters (SEQ ID NO: 1). FIG. 4B shows growth curves of YF PIV on the packaging cell lines. BHK-21 cells containing VEErep/C2/Pac, VEErep/C-prM-E/Pac, VEErep/C2opt/Pac and VEErep/Copt-prM-E/Pac replicons were infected with YF PIV at indicated MOIs in infectious units per cell. At the indicated times, media was replaced and titers of released PIV were determined. FIG. 4C shows plaques developed in VEErep/C2opt/Pac-containing cell line by YFV and YF PIV after 4 days of incubation at 37° C.

FIGS. 5A-5C show that WN PIV develops spreading infection in packaging cells. FIG. 5A is a schematic representation of WN PIV genome and VEEV replicon expressing WNV structural genes. FIG. 5B shows that WN PIV produced foci of WNV antigen-positive cells (revealed with an antibody to NS1-upon infection of BHK(VEErep/C*-E*-Pac) cells after 70 hours of incubation. FIG. 5C shows the same WN PIV preparations produced only single infected cells (revealed at 70 hours post infection with the same tragacanth staining method used in FIG. 5B) upon infection of Vero cell monolayers.

FIGS. 6A-6C show detection of E protein upon release from cells infected with YF and WN PIVs. In FIG. 6A, BHK-21 cells were infected with YF PIV at an MOI of 5 inf.u/cell. The released SVPs were harvested and purified by ultracentrifugation. Samples were resolved by SDS PAGE, transferred to filters, E protein was detected by D1-4G2 MAB. Media harvested from uninfected cells, lane 1; media harvested from the cells infected with YF PIV at 48 h post infection, lane 2; media harvested from the cells infected with YF PIVs at 72 h post infection, lane 3; YFV ($2 \times 10^7$ PFU), lane 4. In FIG. 6B, vero cells were infected with WN PIV for 24 hrs, and then portions of the clarified culture fluid (collected before any cell lysis was detected), were resolved by SDS PAGE, transferred to filters, and reacted with an E-specific MAB (7H2; Bioreliance). Reaction of the same samples with polyclonal sera failed to reveal any cell-associated non-structural proteins in this preparation (results not shown) confirming that the E protein was actively secreted. Sample of WNV, lane 1; media harvested from uninfected cells, lane 2; media harvested from the cells infected with WN PIV at 48 h post infection, lane 3. In FIG. 6C, a western blot showing E protein content of fractions prepared form a sucrose density gradient obtained from SVPs harvested from normal (non-packaging) BHK cells electroporated with YFV PIV RNA. The peak of E protein reactivity (at 32% sucrose) corresponded to the density of SVPs and in agreement with this fact, migrated more slowly than YFV run in a side-by-side analyses (42%).

FIGS. 7A-7F show schematic representation of plasmids used for Yellow fever (YF) and West Nile (WN) pseudoinfectious virus (PIV) production. FIG. 7A shows pYFPIV, FIG. 7B shows pWNPIV, FIG. 7C shows pVEErep/C1/Pac, FIG. 7D shows pVEErep/C2/Pac, FIG. 7E shows pVEErep/C3/PAc, FIG. 7F shows pVEErep/C*-E*-Pac.

FIGS. 8A-8V show the sequences of the plasmids used herein. FIGS. 8A-8D shows sequence of pYFPIV (SEQ ID NO: 6), FIGS. 8E-8H shows sequence of pVEErep/C1/Pac (SEQ ID NO: 7), FIGS. 8I-8K shows sequence of pVEErep/C2/Pac (SEQ ID NO: 8), FIGS. 8L-8O shows sequence of pVEErep/C-prM-E/Pac (SEQ ID NO: 9), FIGS. 8P-8R shows sequence of pVEErep/C2opt/pac (SEQ ID NO: 10), FIGS. 8S-8V shows sequence of pVEErep/Copt-prM-E/Pac (SEQ ID NO:11).

FIG. 10 shows side by side comparison of infectious foci produced in the C-expressing cell line {BHK(VEErep/Pac-Ubi-C*)} by WN RepliVAX at passage 0 (from electroporation) and passage 10 reveals that better-growing variants are readily selected.

FIG. 11 shows titration of RepliVAX PIV produced in WHO-certified Vero cells containing a C-expression cassette (VEErep/Pac-Ubi-C*). Although the resulting PIV is of a slightly lower titer than that produced in BHK cells, the Vero cells multiple harvests of high titer PIV, which is not possible with BHK cells.

FIG. 12A shows replication of WNV/IRES-RLuc replicon with single-base, matching CS mutations demonstrates that some single-base mutations replicate at WT levels. Left part of panel shows the test genome above the 5' and 3'CS sequences. Right side shows replication levels detected using Rluc reporter, as a percentage of the WT replication levels. Underlined bases denotes mutated bases. FIG. 12B shows replication of WNV/IRES-RLuc replicon with matching the double-base changes (m17) derived by combining m10 and m13 (Panel A), compared to replication levels detected with mutants that combine the WT and mutated CS in either possible format, along with a mutant designed to produce an inactive polymerase (negative control). Left part of panel shows the test genome above the 5' and 3' CS sequences. Right side shows replication levels detected using Rluc reporter, as a percentage of the WT replication levels. Underlined bases denotes mutated bases. * denotes no replication detected.

DETAILED DESCRIPTION OF THE INVENTION

Figure 3A:
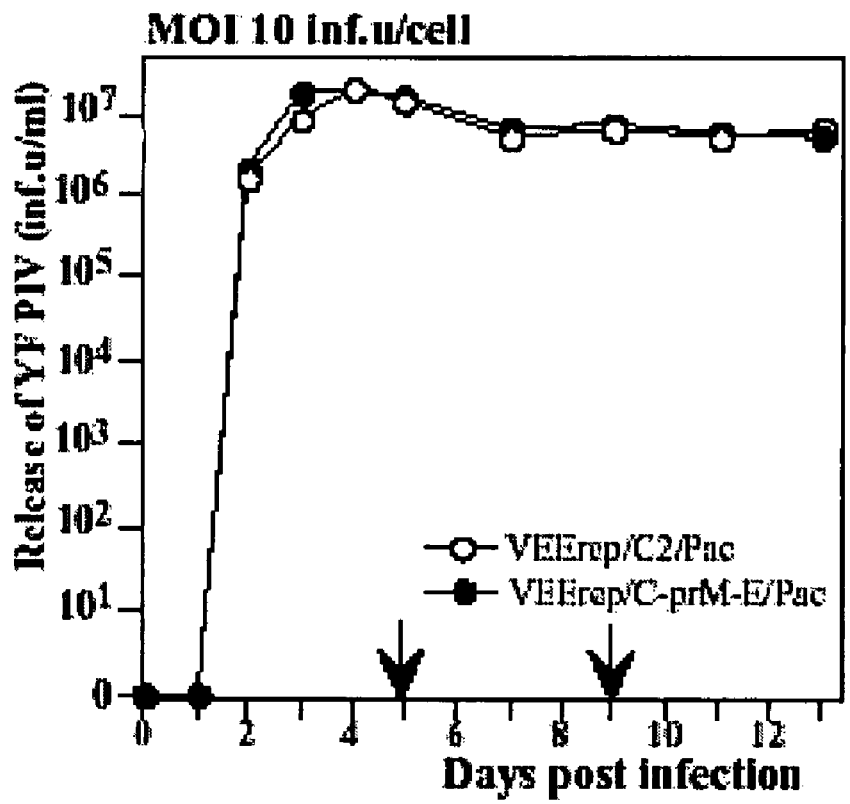
FIGS. 3A-3B show growth curves of YF PIV on the packaging cell lines. BHK-21 cells containing VEErep/C2/Pac and VEErep/C-prM-E/Pac replicons were infected with YF PIV at indicated MOIs in infectious units per cell. At the indicated times, media was replaced and titers of released PIV were determined. Arrows indicate time points when cells were subpassaged at 1:5 ratio.

Safe and effective vaccines have only been produced for a handful of diseases caused by flaviviruses. The classical inactivated viral vaccine (INV) and live-attenuated vaccine (LAV) methods that have been used to produce vaccines to YF, JE, and TBEV have not yet yielded licensed products to prevent diseases caused by other flaviviruses, notably dengue and West Nile encephalitis (WNE). There remain safety concerns about existing LAVs (residual virulence or reversion to virulence) and INV products (reactogenicity due to antigen load and adventitious antigens). Additionally, INVs usually require multiple vaccinations. Further, both types of vaccines are subject to production concerns, including the need to avoid reversion to virulence during propagation of live-attenuated vaccine, and due to the amounts of material needed to produce strong immune responses to the inactivated viral vaccine products and the need for high containment facilities to propagate the virulent viruses used to produce INV products. Although there are promising candidates for new types of flavivirus vaccines, the road to their development will need to overcome these problems.

The present invention in general, is drawn to construction and utilization of replication-deficient pseudoinfective viruses belonging to the Flaviviridae family. In this regard, the present invention describes the development a new type of replication-deficient flaviviruses also referred to as RepliVAX that combines the safety of inactivated vaccines with the efficacy and scalability of live attenuated vaccines. These flaviviruses also identified as pseudo-infectious viruses (PIVs) in the present invention contain genetically engineered flavivirus genomes with a deletion of most of the capsid (C)-encoding region, thereby preventing this genome from producing infectious progeny in normal cell lines or vaccinated animals. However, these pseudo-infectious viruses can be propagated in cell lines expressing either C, or a C-prM-E cassette, where they replicate to high levels. Thus, these pseudoinfectious flaviviruses cannot develop spreading infection in normal cells in vitro or in vivo due to lack of trans-complementation by C protein, and therefore are incapable of causing disease in animals.

In contrast to the vaccines and the methods to generate these vaccines that are known in the art, the present invention provides a system for industrial-scale production of pseudo-infectious flaviviruses that would make such vaccines cheaper to produce than inactivated vaccines at the same time making it safer to use than live-attenuated vaccines. It does so by providing a new type of recombinant vaccine that is capable of only single round of replication in the immunized animals or humans leading to release of subviral particles (SVPs) lacking the genetic material but serving as efficient immunogens.

The present invention has demonstrated that pseudoinfectious flaviviruses can be generated for either yellow fever virus (YFV) or West Nile virus (WNV). Based on this, the present invention contemplates that the method described herein could be broadly applicable to the development of vaccines against other flaviviruses. Further, infection of normal cell lines with such pseudoinfectious flaviviruses produced SVPs that lacked nucleocapsid and a genetic material. The pseudoinfectious flaviviruses described herein demonstrated inability to cause any disease and thus were safe. Additionally, these pseudoinfectious flaviviruses were immunogenic in mice due to competency for single round of replication and release of SVPs, presenting viral antigens. WN PIVs also protected mice from a lethal encephalitis following challenge with WNV.

The PIVs described herein could be produced in a manner that allows for high-yield production in cell culture, and inability to cause disease in animals. These products could be delivered to animals where their defective replication process prevents spread and disease, but permitted the production of SVPs, a flavivirus subunit immunogen that has been shown to be effective in eliciting an efficacious immune response against disease caused by several flaviviruses.

The present invention also demonstrated that the pseudo-infectious flaviviruses approach could be applied to two distantly related mosquito-borne flaviviruses. The applicability of a similar technology to the development of RNA-based vaccines for a tick-borne flavivirus (Kofler, 2004) indicates that the PIV-based technology will be applicable to more distantly related flaviviruses. Additionally, the work with TBEV RNA-based vaccines indicates that in addition to antibody responses to the SVPs (similar to that described herein), the introduction of replicationally active flavivirus genomes into the cells of the vaccinated hosts will produce T-cell responses as well (Kofler, 2004; Aberle, 2005). Although the T cell responses were not measured herein, it is contemplated that the PIVs are capable of inducing T cell response that mimics those produced by viral infection.

Although the PIV vaccines described herein rely on the same flavivirus replication and SVP production strategy that was utilized by the RNA-based vaccines prepared for TBEV (Kofler, 2004; Aberle, 2005), these PIV vaccines do not require gene-gun delivery to animals, can be readily grown in cell cultures, and can subjected to the same types of stabilization and storage (freeze drying) conditions currently being applied to the commercially produced YFV 17D vaccine, thus providing a scalable, storable, and marketable vaccine product. Preliminary studies on stability of WN RepliVAX have shown that freeze-dried preparations show no detectable loss in titer when stored for 30 days at 4 C.

To develop the high-level growth conditions required for efficient trans-complementation (and hence yield) of pseudo-infectious flaviviruses, the present invention utilized cells expressing high levels of C (or C-prM-E) from VEEV replicons. VEEV replicons are less cytopathic than the replicons derived from other alphaviruses and readily establish persistent replications in some cell lines of vertebrate and insect origin. This system appears to be suitable for production of pseudoinfectious flaviviruses, since i) VEEV replicons are highly efficient in synthesis of heterologous proteins and, in the present invention synthesized C to the level required for flavivirus genome incapsidation. ii) VEEV replicons do not detectably interfere with flavivirus replication (Petrakova, 2005). Moreover, VEE replicons and the YF PIV genomes can replicate together in BHK-21 cells without causing CPE. iii) VEEV replicons can be packaged at high-titers into VEE virions that can be used for rapid establishment of the packaging cell lines producing flavivirus structural protein(s).

Furthermore, examination of the effect of context of C expression on yield of PIV indicated that the packaging cells expressing anchored form of C with an additional 20 a.a. of prM produced more particles than cells expressing anchored C alone, suggesting the importance of the proper sequence of processing events in virions formation. The basis for the enhanced packaging efficiency by the construct containing the first 20 amino acids of prM is unclear but this phenomenon might be explained by a requirement of specific order of cleavage at the two nearby cleavage sites (NS2B/NS3- and signal peptidase-specific) (Yamshchikov and Compans, 1994) and/or differences in distribution/stability of C protein products in these two different contexts. In addition, it was observed that co-expression of C with prM and E (VEErep/C-prM-E/Pac) caused only minor increase in PIV yield compared to VEErep/C2/Pac, which expressed anchor C with the fragment of prM.

When the codon-optimization of the VEEV replicon-encoded C genes was examined to determine if this alteration of the C gene sequence enhanced yield of PIV, it did not reveal a strong difference in YFV PIV release from the cells not expressing a codon-optimized C gene. This observation suggested that even with the non-optimized gene VEEV replicons appear to produce C at a saturating level. These results were consistent with other studies demonstrating that the cell lines that expressed VEEV replicons encoding the WNV C-E cassette produced level of E greater than those detected in WNV-infected cells. Despite the inability of the trans-expressed optimized C gene to increase yield of YF PIV, the cells harboring the VEEV replicon expressing Copt developed CPE and produced plaques when infected with YF PIV. This made a PIV infection in the Copt cells even more similar to infection developed by replication-competent virus. An additional advantage of the use of VEEV replicons encoding a YFV Copt gene in pseudoinfectious flavivirus production was the level of safety, since the changes in the codons reduced the chance of homologous recombination with the pseudoinfectious flavivirus genome. Furthermore, the Copt gene was also altered in its cyclization sequence (as described herein for the WNV C coding region in the BHK(VEErep/C*-E*-Pac) cells), to reduce the chance of the recombination producing a replicationally active C-encoding flavivirus. To date, neither the WN nor YF PIV systems described herein have produced replicationally active flaviviruses that could be detected in either cell culture, or in highly susceptible animals. Additionally, in vivo experiments demonstrated that both YF and WN PIVs were safe and could not cause any disease even after i.c. inoculation of 3- to 4-day-old mice with the highest dose of the PIVs. Nevertheless, WN PIVs were capable of inducing high levels of neutralizing antibodies and protected mice against infection with replication competent WNV.

Furthermore, Hepatitis C ranks with AIDS as a major infectious cause of morbidity and mortality for which no vaccine is currently available. In Japan and Korea, HCV now exceeds hepatitis B in contributing to the development of hepatocellular carcinoma, one of the most common types of cancer and a common mode of death due to liver disease. This pattern is likely to become increasingly common in other Asian countries and elsewhere in the developing world, due to the increasing prevalence of HCV coupled with effective immunization against hepatitis B. In some communities in Egypt and elsewhere, the prevalence of hepatitis C infection is spectacularly high, likely due at least in part to traditional health care practices and/or the introduction of dangerous Western technologies in the past (e.g., needle-borne transmission of the virus during public health campaigns directed against schistosomiasis).

In many developing countries, where rates of liver cancer and cirrhosis are high, there is little effective control of hepatitis C during blood transfusion. Hepatitis C is also a major public health problem within the United States, where there are approximately 4 million carriers of HCV, many of whom are at risk of death due to end-stage liver disease or liver cancer. Currently it is estimated that there are between 8,000 and 10,000 deaths annually due to hepatitis C in the United States. This number is likely to triple over the next 10-20 years, potentially exceeding the number of deaths due to AIDS, in the absence of new therapeutic or preventive measures.

Yet, no vaccine is available for prevention of this infection, and efforts (both national and international) to develop a vaccine are severely limited due to perceived technical difficulties, little interest in vaccine development generally on the part of big pharma, and the inertia of major funding agencies. And, as with many infectious diseases, it is the disadvantaged who are at greatest risk of serious liver disease or death due to hepatitis C.

To date attempts to create an effective vaccine against HCV infection have been unsuccessful. However, within last few years, the HCV field started to rapidly develop, and now this virus replicates in tissue culture to reasonably high titers, approaching $10^6$ inf.u/ml. There is a number of obvious similarities between the HCV genome and the genomes of other flaviviruses, like YF, JEV, TBE and others. Therefore, the strategy of designing replication-deficient flaviviruses can be applied not only to the members of the Flavivirus genus, but to Hepacivirus genus (that include HCV) as well. The HCV capsid protein can produced by recombinant alphavirus replicons (based on SINV, VEEV EEEV and others) in a number of cell lines, including Huh-7 and Huh-7.5 cells that are currently known to be susceptible to HCV infection. Replication-deficient HCV genomes, lacking the capsid gene can be transfected into the capsid-producing cell lines and will be packaged into infectious, capsid-containing particles. The successive rounds of infection required for the large-scale production, can be performed on these cells as well. However, in vivo, in the naïve hepatocytes (and possibly other cell types), the HCV genomes lacking the complete capsid gene or no capsid gene at all, will produce only the nonstructural viral proteins, and glycoproteins E1 and E2. These proteins will be presented to immune system i) after proteasome degradation; ii) on the cell surface and iii) in the form of virus-like particles with E1- and E2-containing envelope. Capsid deficiency will make virus incapable of spreading, and thus limited to the cells infected by the vaccinating dose.

In summary, the present invention demonstrated that capsid-deficient, pseudoinfectious flaviviruses i) could produce a spreading infection in the cell lines expressing capsid or all of the flavivirus structural genes; ii) PIVs were incapable of producing spreading infection in normal cells, (iii) PIVs produced E protein containing SVPs when they infected normal cells; (iv) PIVs displayed a high level of safety in the animals; (v) PIVs protected the mice from subsequent flavivirus infection. Taken together, the present invention demonstrated that flavivirus PIVs might be a safe, potent, and efficacious platform for development of vaccines against flavivirus infections and infections caused by viruses similar to Favivirus.

The present invention is directed to a replication-deficient pseudoinfectious Flaviviridae, comprising: a deletion in the nucleotide sequence encoding capsid (C) protein such that the deletion does not disrupt the RNA sequence required for genome cyclization, the signal sequence for prM protein that is required for the proper maturation of prM/M or a combination thereof, where the Flaviviridae replicate only in cells expressing Cprotein or C, prM, envelope protein, mutated C protein, mutated prM, mutated envelope protein or combinations thereof of a virus of the Flaviviridae family. Generally, the Flaviviridae comprises a virus belonging to the genus flavivirus, Hepacivirus or Pestivirus or other chimeras of said viruses created by exchanging the prM-E cassettes of other viruses with the prM-E cassettes of the pseudoinfectious Flaviviridae. The examples of the viruses belonging to the genus Flavivirus are not limited to but may include yellow fever virus, West Nile virus, dengue virus, tick-borne encephalitis virus, Saint Louis encephalitis virus, Japanese encephalitis virus, Murray Valley encephalitis virus. Furthermore, the example of the virus belonging to the genus Hepacivirus includes but is not limited to Hepatitis C virus and those belonging to the genus Pestivirus include but are not limited to Bovine virus diarrhea, a swine fever virus or a hog cholera virus.

In case of flavivirus, the nucleotide sequence encoding the C protein of the Flavivirus that is deleted may encode amino acids 26 to 100 or a combination of amino acids within amino acids 26 to 100 of the C protein. Such combinations may include but are not limited to amino acids 26-93, 31-100 or 31-93. One of ordinary skill in the art can use the same guidelines to delete nucleotide sequence of C protein from other viruses belonging to the Flaviviridae family or other viruses having the same genetic makeup as these viruses. In general and applicable to all the viruses, the deleted gene is replaced by a gene encoding a marker protein or an antigen. The example of a marker protein may include but is not limited to a green fluorescent protein.

The present invention is also directed to a cell culture system expressing C protein or C, prM, envelope protein, mutated C protein, mutated prM, mutated envelope protein or combinations thereof of a virus of the Flaviviridae family, effective to enable propagation of the above-described replication-deficient Flaviviridae under suitable conditions. For this purpose, the cells expressing wild type or mutated proteins of the Flaviviridae may be generated using genetically engineered replicons derived from viral vectors.

In general, the gene encoding the protein(s) of the virus of the virus Flaviviridae family in the replicon is replaced by a codon-optimized version of the gene encoding the protein(s) of the virus such that the replacement reduces the ability of the cell line-encoded genes to recombine with the genome of the pseudoinfectious virus of the Flaviviridae family and/or increases the production of the pseudoinfectious virus of the Flaviviridae family.

For instance, such replicons may express a C protein that comprises mutations in at least 36 nucleotide positions of the gene encoding C protein of the virus of the Flaviviridae family. The replicon may express a C protein in the replicon that comprises unnatural cyclization sequences such that presence of the cyclization sequences reduces the chances of productive recombination of the replication-deficient pseudoinfective virus with natural viruses. Further, the replicon may express proteins comprising altered nucleotide sequences encoding truncated C-prM junction such that presence of such altered sequences enhances yield of the replication-deficient pseudoinfective virus in cell culture, prM/E containing SVP yield in vivo or a combination thereof.

Furthermore, the replicons expressing the proteins of Flaviviridae are introduced into the cells by transfection with in vitro synthesized replicon RNAs, by transfection with plasmid DNAs designed to synthesize functional alphaviral replicons from cellular RNA-polymerase II-specific promoters or by infection with alphaviral replicons packaged inside the alphaviral structural proteins. The viral vectors used herein may be alphaviruses. Representative examples of such alphaviruses are not limited but may include Venezuelan Equine Encephalitis Virus (VEEV), Sindbis virus, Eastern Equine Encephalitis virus (EEEV), Western Equine Encephalitis virus (WEEV) or Ross River virus.

The present invention is further directed to a method of producing a replication-deficient pseudoinfectious virus of the Flaviviridae family, comprising; generating a replication-deficient pseudoinfectious virus of the Flaviviridae family that comprises a deletion in the capsid gene such that the deletion does not disrupt the RNA sequence required for genome cyclization, the signal sequence for prM protein that is required for the proper maturation of prM/M or a combination thereof; generating a cell line that expresses C protein or C, prM, envelope protein, mutated C protein, mutated prM, mutated envelope protein or combinations thereof of a virus of the Flaviviridae family, where the cell line provides high levels of the proteins needed for propagation of the replication-deficient pseudoinfectious virus of the Flaviviridae family; and infecting the cell line with the pseudoinfectious virus of the Flaviviridae family, thereby producing the replication-deficient pseudoinfectious virus of the Flaviviridae family. All other aspects regarding the types of viruses, the position of deletions in the capsid gene, the method of generation of the cell line expressing the mutated and wild type proteins of the Flaviviridae, the type of replicons and the mutations within the replicons and the modifications in the gene encoding the mutated and wild type proteins of the Flaviviridae in the replicons are the same as discussed supra.

The present invention is also directed to a pharmaceutical composition, comprising the replication-deficient pseudoinfectious virus of the Flaviviridae family produced by the method described supra. The present invention is further directed to a method of protecting a subject from infections resulting from exposure to Flaviviridae, comprising administering to the subject an immunologically effective amount of the pharmaceutical composition described herein, where the composition elicits an immune response against the Flaviviridae in the subject, thereby protecting the subject from the infections. Such a composition may be administered via intraperitoneal, intradermal, subcutaneous, intramuscular, oral, or intranasal route. Furthermore, the subject benefiting from use of this composition may be a human, or an animal.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. As used herein, the term, "Flaviviridae" includes the genera Flavivirus, Hepacivirus and Pestivirus. The examples of virus belonging to the genus Flavivirus include but are not limited to yellow fever virus, West Nile virus, dengue virusm a tick borne encephalitis virusm a Saint Louis encephalitis virus, a Japanese encephalitis virus or a Murray Valley encephalitis virus, Similarly, the example of virus belonging to the genus Hepacivirus includes but is not limited to Hepatitis C virus and those belonging to the genus Pestivirus include but are not limited to Bovine virus diarrhea, a swine fever virus or a hog cholera virus.

Furthermore, although the present invention discloses the construction and utility of a replication-deficient pseudoinfectious Flaviviridae belonging to the genus Flavivirus, one of ordinary skill in the art can use the same guidelines to construct chimeras comprising other viruses belonging to the Flaviviridae or to construct chimeras by exchanging the prM-E cassettes of viruses within the Flaviviridae or other similar viruses and the viruses within the Falviviridae.

The pharmaceutical compositions comprising the pseudoinfectious viruses belonging to the Flaviviridae family discussed herein may be administered concurrently or sequentially with each other or with other pharmaceutical composition(s). The effect of co-administration of such compositions is to protect an individual from the infections caused by such viruses and other vaccine-treatable disease. The composition described herein, the other pharmaceutical composition, or combination thereof can be administered independently, either systemically or locally, by any method standard in the art, for example, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration and are well known to an individual having ordinary skill in this art.

The composition described herein, the other pharmaceutical composition or combination thereof may be administered independently one or more times to achieve, maintain or improve upon a therapeutic effect. It is well within the skill of an artisan to determine dosage or whether a suitable dosage of either or both of the compositions comprises a single administered dose or multiple administered doses. An appropriate dosage depends on the subject's health, the protection of the individual from flaviviral infections, the route of administration and the formulation used.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Cell Cultures

The BHK-21 cells were provided by Paul Olivo (Washington University, St. Louis, Mo.). They were maintained at 37° C. in alpha minimum essential medium (aMEM) supplemented with 10% fetal bovine serum (FBS) and vitamins. WHO-certified Vero cells, originally prepared for use in human vaccine manufacture were provided by Dr. Steve Whitehead of the NIH. Vero cells were maintained in MEM containing 6% FBS.

Example 2

Plasmid Constructs

Standard recombinant DNA techniques were used for all plasmid constructions. A schematic representation of the plasmids used are shown in FIGS. 7A-7F. Maps and sequences are shown in FIGS. 8A-8F. The parental low-copy number plasmid pACNR/FLYF-17Dx containing infectious cDNA of YFV 17D strain genome was described elsewhere (Bredenbeek et al., 2003) and provided by Dr. Charles M. Rice (Rockefeller University, New York, N.Y.). pYFPIV contained defective YFV genome (YF PIV), in which fragment encoding amino acid. 26-93 of YF capsid gene was replaced by codon-optimized GFP gene derived from pEGFP-N1 (Clontech). The WN PIV genome (pWNPIV) was derived from a Texas 2002 infectious cDNA (Rossi et al., 2005), by fusion of codon 30 of C to codon 101 of C (see FIG. 5A). The plasmids pVEErep/C1/Pac, pVEErep/C2/Pac and pVEErep/C-prM-E/Pac (FIG. 2A) encoded double subgenomic VEEV replicons, in which the first subgenomic promoter was driving transcription of the RNAs containing 5'UTR of VEEV 26S RNA followed by sequences, corresponding to nt 119-481, 119-541 and 119-2452 of YFV genome, respectively. The second subgenomic promoter was driving the expression of puromycin acetyltransferase (Pac) gene, whose product was making cells resistant to translational arrest caused by puromycin (Pur). Non-cytopathic VEEV replicons expressing the C-prM-E cassette of WNV {derived from a Sindbis virus replicon (Scholle et al., 2004)} fused to the Pac gene (designated pVEErep/C*-E*-Pac) was created from a VEE non-cytopathic replicon (Petrakova et al., 2005); E-coding sequence was fused with Pac gene through a linker consisting of the first 9 codons of NS1 and the last 25 codons of NS2B, followed by 2 codons of NS3 fused directly to FMDV 2A (see FIG. 5A). The codon-optimized sequence encoding YFV 17D capsid and first 20 amino acid of prM was designed using the codon frequency data described elsewhere (Haas et al., 1996). This gene was synthesized by PCR from the overlapping synthetic oligonucleotides. The amplified fragment was sequenced before cloning into expression cassettes VEErep/C2opt/Pac and VEErep/Copt-prM-E/Pac. The latter replicons had essentially the same design as pVEErep/C2/Pac and pVEErep/C-prM-E/Pac, but contained codon-optimized sequence presented in FIG. 4A.

Additionally, a chimeric WN-RepliVAX expressing the JEV prM-E has also been generated. This was constructed by substituting the prM and E genes of Nakayama strain of JEV in A RepliVAX encoding the WNV genome. The gene exchange was achieved by direct fusion of the last codon of the truncated WNV C protein to the first codon of the prM coding sequence of JEV (Nakayama strain). The same fusion strategy was employed at the 3' end of the cassette, with the final codon of the JEV E protein fused directly to the first codon of NS1 of WNV. These fusions were introduced into a BAC plasmid encoding the entire WN RepliVAX cDNA bounded by a T7 promoter and a ribozyme, and RNA recovered from this BAC DNA was introduced into BHK(VEErep/Pac-Ubi-C*) cells. The resulting RepliVAX (designated JE RepliVAX) formed spreading infectious foci on BHK (VEErep/Pac-Ubi-C*). As for WN RepliVAX, the foci formed on this cell line are smaller than those produced by a fully infectious WNV-JEV chimera. JE RepliVAX grows to titers approximately 10 times lower than WN RepliVAX, achieving titers of over $10^6$ U/ml in BHK(VEErep/Pac-Ubi-C*). As expected, JE RepliVAX reacts with JE-specific MAbs, and it is anticipated that like chimeric flaviviruses, JE RepliVAX will induce high levels of JEV-neutralizing antibodies, and protect against JE.

Example 3

RNA Transciptions

Plasmids were purified by centrifugation in CsCl gradients. Before the transcription reaction, the plasmids were linearized by XhoI (for pYFPIV) or MhuI (for VEE replicon and VEE helper encoding plasmids) or SwaI (for pWNPIV). RNAs were synthesized by SP6 or T7 RNA polymerase in the presence of cap analog. The yield and integrity of transcripts were analyzed by gel electrophoresis under non-denaturing conditions. Aliquots of transcription reactions were used for electroporation without additional purification.

Example 4

RNA Transfections and PIV Replication Analysis

Electroporation of BHK-21 cells was performed under previously described conditions (Liljestrom et al., 1991). For establishing packaging cell cultures, Pur was added to the media to a concentration of 10 g/ml 24 h post electroporation of the VEEV replicons. Transfection of in vitro-synthesized YF PIV genome was performed 5 days later, when replicon-containing cells resumed efficient growth. Samples were harvested at the time points indicated in the figures by replacing the media with the same media, containing Pur. In many experiments, PIV-secreting cells were split upon reaching the confluency.

VEEV replicons were packaged into VEEV infectious virions by co-electroporation of the in virto synthesized replicon and 2 helper RNAs (Volkova et al., 2006) into BHK-21 cells. Replicon-containing viral particles were harvested 24 h post transfection and used for infecting of naïve BHK-21 cells, followed by Pur selection. In the case of WN PIV, the in vitro-synthesized PIV RNA was transfected into BHK cells containing VEErep/C*-E*-Pac replicon expressing WN C, prM and E and Pac [BHK(VEErep/C*-E*-PAC) cells]. THE scheme of the VEErep/C*-E*-PAC genome is presented in FIG. 5A. Harvested PIVs were passaged on these cells using standard methods (Rossi et al., 2005).

Example 5

Measuring the Titers of YF PIV

For measuring the titers of released YF PIV, BHK-21 cells were seeded into six-well Costar dishes at a concentration of $5 \times 10^5$ cells/well. Four hours later, cells were infected with different dilutions of packaged replicons, and after 1 h incubation at 37° C. in an 5% $CO_2$ incubator, they were overlaid with 2 ml of MEM supplemented with 10% FBS. The numbers of infected cells were estimated by counting GFP-positive cells under an inverted UV microscope. The fraction of infected cells from the seed quantity was determined via counting of fluorescence-producing cells in a defined area of microscopic field. Counts for 5 different fields were averaged and recalculated for the titer corresponding to each serial dilution.

In the later experiments, titers were also measured by plaque assay on the monolayers of BHK-21 cells, carrying VEErep/Copt-prM-E/Pac replicon, using previously described conditions (Lemm et al., 1990), except cells were incubated under agarose for plaque development for 5 days, then fixed by 2.5% formaldehyde and stained with crystal violet.

Example 6

Passaging of YF PIVs

Packaging cell lines were established either by transfection of the in vitro-synthesized VEEV replicon RNAs or by infecting cells with the same replicons packaged into VEEV structural proteins at a multiplicity of infection (MOI) of 10 inf.u/cell. After Pur selection, they were infected with YF PIV at different MOIs. Samples were harvested at the time points indicated in the figures by replacing the media.

Example 7

Analysis of YF SVP Production

BHK-21 cells were seeded at a concentration of $2 \times 10^6$ per 100-mm dish. After 4 h incubation at 37° C., cells were infected with YF PIV at an MOI of 10 inf.u/cell, and then incubated for 24 h in 10 ml of MEM supplemented with 10% FBS. Then the medium was replaced by 10 ml of serum-free medium VP-SF (Invitrogen) that was replaced every 24 h to analyze SVP release. The collected VP-SF samples were clarified by low-speed centrifugation (5,000 r.p.m, 10 min, 4° C.), and then concentrated by ultracentrifugation through 2 ml of 10% sucrose, prepared on PBS, in SW-41 rotor at 39,000 r.p.m, 4° C. for 6 h. Pellet material was dissolved in the loading buffer for SDS-polyacrylamide gel electrophoresis, lacking b-mercaptoethanol (to preserve binding to D1-4G2 MAB) and further analyzed by Western blotting. After protein transfer, the nitrocellulose membranes were processed by D1-4G2 MAB, and horseradish peroxidase (HRP)-conjugated secondary donkey anti-mouse antibodies purchased from Santa Cruz Biotechology. HRP was detected using the Western Blotting Luminol Reagent according to the manufacurer's recommendations (Santa Cruz Biotechnology). To obtain positive control sample, YFV ($2 \times 10^8$ PFU) was subjected to ultracentrifugation through 10% sucrose cushion as described above for SVPs.

For sucrose density gradient analysis of YFV SVPs, BHK-21 cells were electroporated with the in vitro synthesized YF PIV genome RNA. At 24 hours post-transfection, the complete MEM was replaced by VP-SF medium, which was harvested 24 hours later. At this time, more than 95% of the cells were GFP-positive and did not exhibit any signs of CPE. The harvested sample was clarified by low-speed centrifugation (5000 rpm, 10 min, 4° C.) and then concentrated by overnight centrifugation in a SW-28 rotor at 25,000 rpm, 4° C. The resulting pellet was suspended in TN buffer (10 nm Tris HCl (pH 7.5), 100 mM NaCl, 0.1% BSA) and further analysis was performed as described (Schalich et al., 1996).

Briefly, 0.5 ml samples were loaded in to the discontinuous sucrose gradient (1.5 ml of 50%, 1.5 ml of 35% and 1.5 ml of 10% sucrose prepared in PBS buffer). Centrifugation was performed in SW-55 rotor at 45,000 rpm at 4° C. for 1 h in Optima MAX Ultracentrifuge (Beckman). Pellets were dissolved in the loading buffer for SDS polyacrylamide gel electrophoresis, lacking b-mercaptoethanol (to preserve binding to D1-4G2 MAB) and further analyzed by Western blotting. After protein transfer, the nitrocellulose membranes were processed by D1-4G2 MAB and horseradish peroxidase (HRP)-conjugated secondary donkey anti-mouse antibodies purchased from Santa Cruz Biotechnology. HRP was detected using Western Blotting Luminol Reagebbr according to the manufacturer's recommendation (SantaCruz Biotechnology). Side by side gradient analyses were performed with YFV ($2 \times 10^8$ PFU), subjected to the same procedures as described above for YFV-PIV derived SVPs.

Example 8

Analyses of WN PIV

Titers of WN PIV were determined by infecting Vero cell monolayers with serial dilutions of virus, and then fixing 24 hours later and immunohistochemically staining with a polyclonal hyperimmune mouse ascite fluid specific for WNV, as previously described (Rossi et al., 2005). Infected cells were enumerated and used to determine the titer. To evaluate the ability of WN PIV for foci formation on Vero cells or the BHK(VEErep/C*-E*-PAC) cells, monolayers were infected with dilutions of WN PIV, overlaid with a semisolid tragacanth overlay, incubated at 37 C, and then fixed and stained with a MAB specific for WNV NS1 (provided by E. Konishi, Kobe, Japan), as described above.

Example 9

PIV Safety Studies

PIV safety was established by inoculation of different doses of virus (YFV 17D or WNV TX02 recovered from parental infectious cDNAs) or PIV into 3- to 4-day-old mice (outbred Swiss Webster, Harlan) by the intracranial (i.c.) route (20 ml volume), or 4-5 week old female mice (outbred Swiss Webster, Harlan) by the intraperitoneal (i.p.) route (100 ml volume). Mice were monitored for 14 days for signs of disease and death, animals that were moribund, and appeared to be unable to survive until the next day were humanely euthanized and scored as "dead" the following day.

Example 10

WN PIV Potency and Efficacy Studies

Selected animals inoculated with WN PIV as described above were euthanized and bled at 21 days post inoculation. Sera were harvested from the animals, pooled, and tested for their ability to reduce WNV focus formation on Vero cell monolayers using the methods described above. The remaining animals were inoculated with 1,000 inf.u (determined by focus-forming assay on Vero cells), corresponding to approximately 100 $LD_{50}$ of the NY99 strain of WNV (Xiao et al., 2001), and animals were then observed for an additional 14 days as described above.

Example 11

Figure 1:
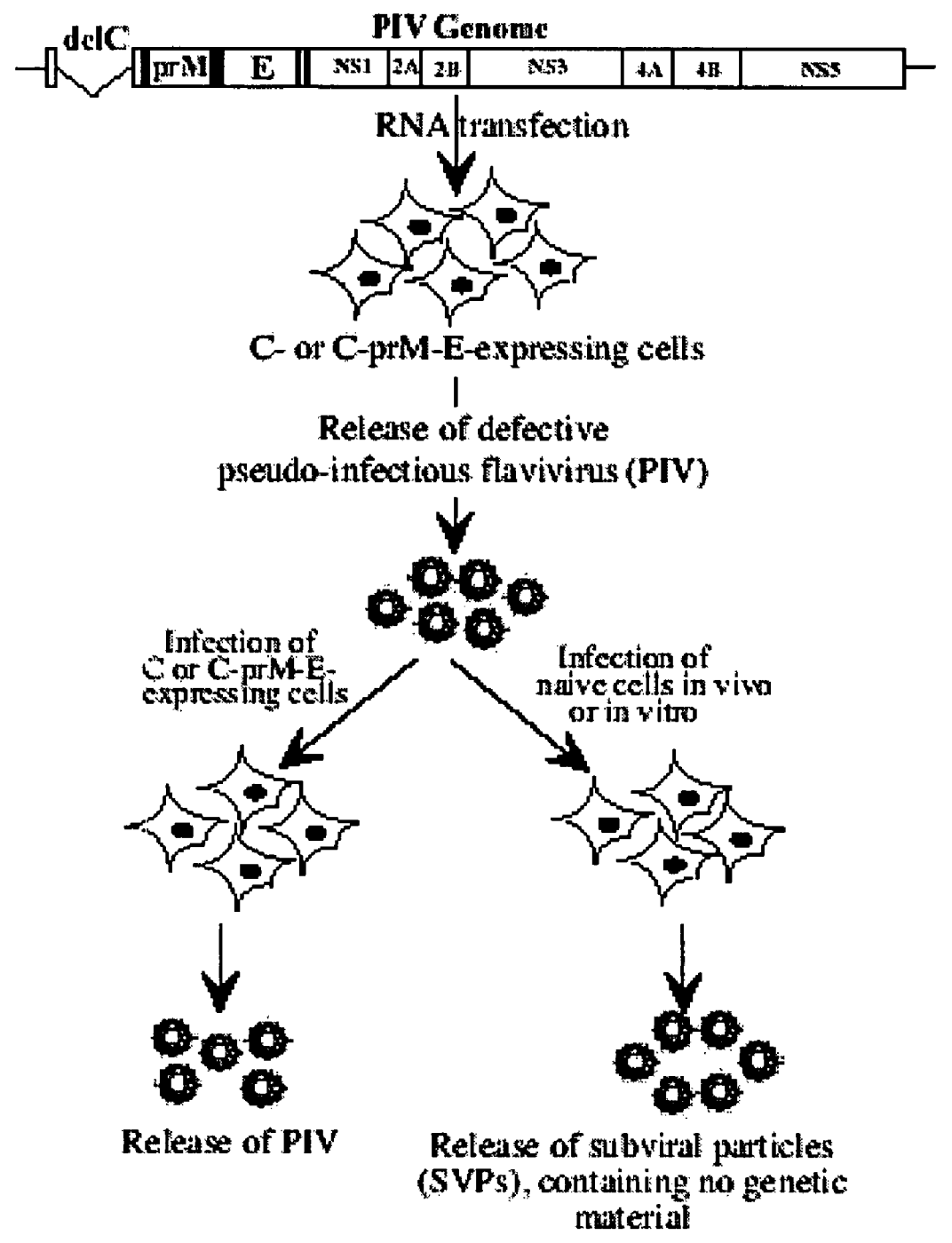

Both YFV C- and YFV C-prM-E-Expressing Cassettes can Complement Replication of YFV PIV The general strategy for complementation of a C deletion defect in the flavivirus genome is presented FIG. 1. It is based on development of genomes lacking the C gene, and propagation of these pseudoinfectious viral genomes (PIV genomes) in cells expressing C (or all of the viral structural proteins), but not in normal cells. Replication in the latter cells, producing no viral structural proteins required for trans-complementation of the defect in PIV genome, leads to release of SVPs containing the critical protective immunogen E, but lacking the nucleocapsid containing C and the viral genetic material.

A recombinant YFV genome (YF PIV genome) was engineered to contain GFP in place of amino acid 26-93 of C, cloned in-frame with the rest of the polypeptide (FIG. 2A). The expression of GFP provided a convenient way of determining the titers of genome-containing PIVs in the experiments. The deletion in the C-coding sequence from this PIV genome was expected to destroy the ability of C to form a functional nucleocapsid, but it was not expected to affect production of functional forms of prM and E. Thus, cells expressing this genome, which produced GFP fluorescence could not release infectious virus. However, infectious progeny was expected to be produced from "packaging" cells expressing high levels of C.

For rapid development of the cell lines for efficient PIV production, the Venezuelan equine encephalitis virus (VEEV) genome-based expression system (replicons) (Petrakova et al., 2005) was used. VEEV replicons are less cytopathic than replicons derived from other alphaviruses and readily establish persistent replication in some cell lines of vertebrate and insect origin. The expression cassettes were designed as double subgenomic constructs (FIG. 2B), in which one of the subgenomic promoters was driving the expression of Pac, providing an efficient means to eliminate cells in the transfected cultures that do not contain the Pac-expressing VEEV replicon. The second subgenomic promoter was driving the transcription of subgenomic RNA encoding YFV structural proteins. To identify the most efficient packaging cassettes, VEEV replicons encoding either i)

YFV C with the signal peptide of prM, also known as anchored C (Lindenbach and Rice, 2001), (VEErep/C1/Pac), or ii) C with the signal peptide and 20 amino acid of prM (VEErep/C2/Pac), or iii) all of the YFV structural proteins (VEErep/C-prM-E/Pac). The rationale of the design was to retain the signal peptide in the C-coding cassettes that was expected to be essential for targeting C into proper cellular compartment.

The in vitro-synthesized VEEV replicon RNAs were transfected into BHK-21 cells and the Pur$^R$ stable cell lines were selected over the next 4-5 days in the Pur-containing medium. During the first 2-3 days post transfection, replication of VEEV-derived RNAs caused growth-arrest, then, as described our previously (Petrakova et al., 2005), replication became less efficient and cells resumed their growth. The resulting Pur$^R$ cultures were transfected with the in vitro-synthesized YF PIV RNAs, and at different times post transfection, titers of the released infectious particles, containing GFP-expressing genomes were determined (FIG. 2C). Surprisingly, the presence of two different replicating RNAs (YFV- and VEEV-specific) in BHK-21 cells did not result in cytopathic effect (CPE), and maintained both resistance to Pur and expression of high level of GFP, indicating replication of both the VEEV replicon and YF PIV RNA. As shown in FIG. 2C, cultures expressing both of these marker genes were capable of growing and required subpassaging (at ~1:5 ratio every 4 days) to prevent the cultures from reaching confluency. The experiments shown in FIG. 2 demonstrated that all three VEEV replicons were capable of supplying YFV C at levels sufficient for formation of infectious PIVs; no infectious particles were released from the naive BHK-21 cells transfected with the YF PIV RNA in the absence of VEEV replicons (data not shown). However, cells expressing these packaging cassettes differed in their ability to produce PIV. Constructs expressing YFV C followed by the prM signal peptide (anchored C; VEErep/C1/Pac) demonstrated the lowest level of YF PIV RNA packaging, compared to cassettes expressing longer protein sequences. The basis for the lower packaging efficiency is by the C1 construct is unclear, but this phenomenon might be explained by a requirement for a specific ordering of cleavage at the two nearby cleagage sties (NS2B/NS3 and signal peptidase) (Yamshchikov and Compans, 1994), and/or differences in distribution/stability of the C protein produced in these two different contexts. of the stability of this protein. Thus, after these experiments, VEErep/C1/Pac was eliminated from all further experiments. Both VEErep/C2/Pac and VEErep/C-prM-E/Pac replicons packaged YF PIV to the similar titers approaching above $10^7$ inf.u/ml. Moreover, the release of PIV particles continued until the experiments were terminated, with each cell releasing ~20 infectious YF PIV per 24 h time period. The same cells were probably also releasing prM/E-containing SVPs lacking the nucleocapsid and genome, but this possibility was not further investigated.

Example 12

YF PIVs with Defective Genomes can be Produced at a Large Scale

The ultimate utility of PIV as vaccine candidates is dependent upon the ability to produce these particles at the scales needed, for instance, for commercial production. Reliance on an RNA-based trans-complementation system (VEEV replicons) for vaccine manufacture requires further standardization since there is a possibility of accumulation of mutations in the heterologous genes cloned into genomes of RNA viruses. The use of low-passage cell lines, is one of the solutions for overcoming this limitation. Alternatively, accumulation of mutations in the VEErep genomes can be minimized by repeated transfection of the replicon into naïve cells, or by production of packaged VEEV replicons followed by infection of naïve cells. The use of packaged VEE replicons was considered to be one simple and efficient means for establishing the packaging cell lines.

Figure 3B:
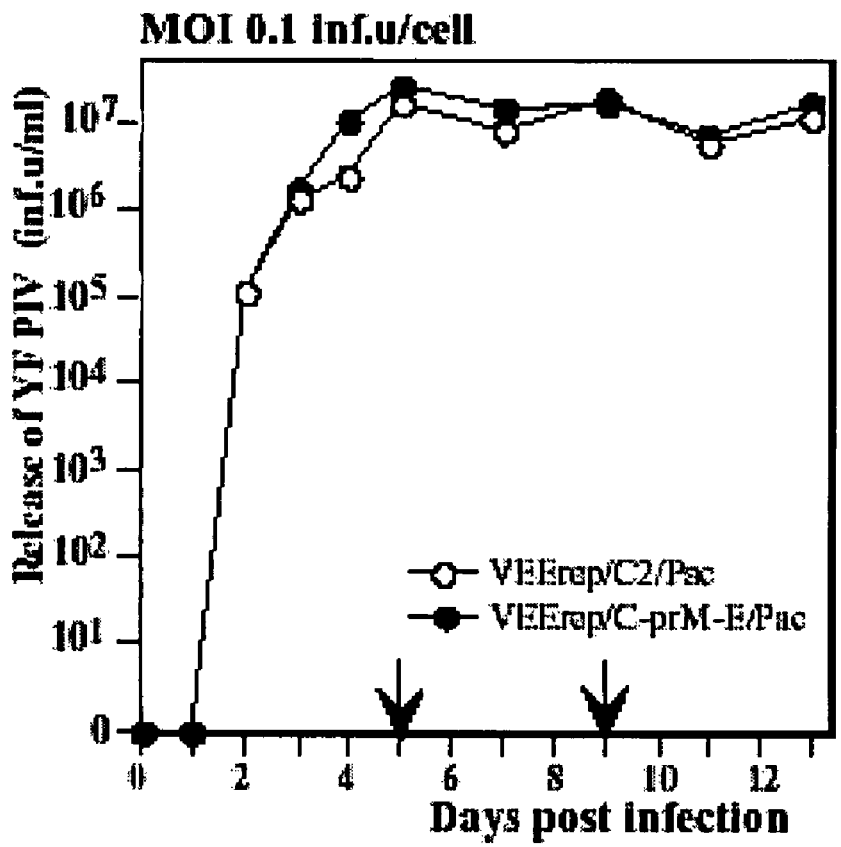

To efficiently produce PIVs, a technology that permits production of alpha virus replicon expressing cell cultures in previously packaged VEEV replicons was used. Briefly, VEEV replicons were packaged into VEEV infectious virions using previously described two-helper system (Volkova et al., 2006), into preparations that contained titers approaching $10^9$ inf.u/ml. BHK-21 cells infected with these particles and selected in the presence of Pur could be used to obtain YFV structural protein-encoding cell cultures in 3-5 days. Following establishment, the VEErep/C2/Pac- and VEErep/C-prM-E/Pac-containing cell lines were infected with previously generated samples of YF PIVs at high (10 inf.u/cell) and low (0.1 inf.u/cell) MOIs. In all cases, the defective YFVs replicated productively (see FIG. 3) and infected all of cells in the monolayers producing high titers of PIVs. Thus, rapid establishment of packaging cell lines by infecting cells with packaged VEEV replicons, followed by infection with PIVs appears to be a simple and efficient system a for large-scale production of PIVs with the deleted C sequence in the genome.

Example 13

Production of YF PIVs Using VEE Replicons Expressing Codon-Optimized Form of YFV C Gene Another possible problem in using the packaging systems to support replication of defective viruses is recombination between the defective viral genomes and the RNAs encoding the trans-complementing gene(s). Such recombination might lead to generation of the infectious viruses. In the experiments described herein, infectious YFV using a plaque assay were never detected, but it was necessary to rule out the possibility that live virus can be formed in these cells.

In addition, the proteins encoded by many arthropod-borne viruses are expected to have evolved to utilize the translational machinery in two very different hosts. Thus, their codon usage is not expected to be optimal for expression in either host. Therefore, the C-coding sequence in the expression cassettes was modified to achieve two goals: i) to enhance the yield of C production and ii) to reduce possibility of homologous recombination between YF PIV genome and C-coding subgenomic RNA of VEE replicons. YFV C was synthesized using the codon frequency found in the most efficiently translated mammalian genes (FIG. 4A). These silent mutations also disrupted the cyclization sequence required for flavivirus genome replication, thus, reducing the possibility of generating replication competent YFV in an event of recombination between YF PIV genome and YFV C-coding RNA of VEEV replicon.

The Copt gene was cloned into VEErep constructs, VEErep/Copt/Pac and VEErep/Copt-prM-E/Pac, using the same strategy as VEErep/C2/Pac and VEErep/C-prM-E/Pac, and trans-complementing Pur$^R$ cell lines were established either by RNA transfection or by infecting the cells with packaged RNAs. Transfection of these cells with the in vitro-synthesized PIV genome RNA produced PIV with efficiencies that were similar to those selected with the cells expressing VEEV replicons expressing the non-optimized YFV C gene (FIG. 4B). However, the cells expressing the codon-optimized C proved to be a useful reagent in that they were capable of developing CPE and forming clearly visible plaques when infected with YF PIV and overlaid with agarose containing media with low concentration of FBS (FIG. 4C). Thus, although codon optimization of YFV C gene did not alter PIV production from these cells, the cells expressing the codon-optimized YFV C represent a very useful system for evaluation of YF PIVs, particularly those expressing no fluorescent markers. In additional tests, a very good correlation was observed between the titers of the same samples determined in plaque-forming assays and GFP-foci assays.

Plaques formed by YF PIV were smaller than those of YFV indicating that structural proteins were most likely produced in cis finctio more efficiently in viral particle formation. The reason for attaining the ability to form plaques is not completely understood yet. However, it is speculated that YFV C has some level of cytotoxicity because of cell lines containing VEEV replicons expressing the codon-optimized version of this protein demonstrated lower growth rates (data not shown) than corresponding counterparts with replicon encoding natural C gene. Thus, YF PIV genome replication might lead to additional changes in the intracellular environment that were sufficient to cause CPE.

Example 14

PIVs can be Generated for Other Flaviviruses

To prove that PIVs can be easily generated for other flaviviruses, the strategy described above was applied to WNV. To this end, a WN PIV genome with a 35-amino acid-long C protein was created (FIG. 5A). To package this WN PIV genome, a packaging cell line generated by transfection of BHK cells with a non-cytopathic VEEV replicon expressing WNV C/prM/E and Pac [BHK(VEErep/C*-E*-Pac) was used. To minimize the chance that recombination between WN PIV genomes replicating in this cell line and the VEErep RNA-encoded C protein could lead to generation of the infectious WNV, the WNV C-coding gene in the VEEV replicon was modified to contain clustered silent mutations in the WNV cyclization domain.

Media harvested from BHK (VEErep/C*-E*-Pac) cells transfected with the synthetic WN PIV genome were capable of producing antigen-positive foci in the packaging cells (FIG. 5B) indicating that infectious WN PIV had been produced. However, only antigen-positive cells were detected upon infection of Vero cell monolayers with same samples (FIG. 5C). Titers of up to $1\times10^8$ inf.u/ml of WN PIV were produced on the packaging cells, and as expected, WN PIV could be repeatedly passed on this cell line. Thus, using an established cell line, high titer stocks of WN PIV could be readily obtained using the same complementation system described above for YFV. Interestingly, in the case of the WNV packaging cell line and WN PIV, it was observed that the virus yields plateaued late in infection, simultaneously with the appearance of CPE (results not shown), whereas the cells co-replicating YF PIV genome and VEEV replicons continued to produce PIV for many days (FIG. 2).

Example 15

Cells Infected with YF or WN PIVs Produce SVPs

To demonstrate that cells infected with PIVs produced SVPs, BHK-21 cells were either transfected with the in vitro-synthesized YF PIV RNA or infected with YF PIVs produced in C-expressing cells. The particles released from the BHK-21 cells were purified by ultracentrifugation, and analyzed by western blotting using a mouse monoclonal antibody (MAB) specific for E, D1-4G2 (Gentry et al., 1982). Both RNA-transfected and PIV-infected cells produced E protein that could be pelleted from the media (FIG. 6A), indicating that it was present in a particulate form. Since these cells did not exhibit any CPE, and the samples were clarified at low-speed centrifugation prior to ultracentrifugation, it is unlikely that the E protein detected in the pelleted fraction represented cellular debris. Similarly, western blot analyses demonstrated that Vero cells infected with the WN PIV produced (before development of any signs of CPE) extracellular forms of E that were indistinguishable in size from those produced by WNV-infected Vero cells (FIG. 6B).

To further evaluate the physical nature of the E protein released by PIV-infected cells, media collected from cells containing replicating PIV genomes only were subjected to sucrose density gradient analysis in agreement with published data (Schalich et al., 1996). SVPs were found in the fraction having 2% sucrose (FIG. 6C). In the same experiment, YFV virions demonstrated high density and were detected in the fraction with 42% sucrose. E protein-containing particles that migrate at the expected size of WNV SVPs have also been detected in cultures infected with WNV PIVs. The presence of E in the media of PIV-infected cells was consistent with the production of SVPs by cells expressing only prM/E or TBEV RNA vaccines lacking a functional C gene.

Example 16

PIV Safety Potency, and Efficacy in Animals

Safety of WN and YF PIVs was established by i.c. inoculation of litters of 3 to 4-day-old mice. These studies showed that mice inoculated with WT YFV or WNV were quickly killed, and these viruses displayed a 50-percent lethal dose ($LD_{50}$) of approximately 1 PFU in these animals (Table 1). However, WN and YF PIVs inoculated into suckling mice at a dose of $2\times10^6$ inf.u failed to kill any mice (Table 1). Safety was further documented by i.p. inoculation of adult mice with wild type (wt) viruses and WN PIVs. These studies showed that the WN PIVs were completely safe in adult mice (Table 2). Furthermore, wt WNV killed a significant portion of adult mice, with an $LD_{50}$ of less than 1 PFU, and doses of up to $3\times10^6$ inf.u of WN PIV failed to cause any death (Table 2). Most interestingly, however, is the finding that the WN PIVs were very potent immunogens (NEUT titers were detected with inoculation of as few as 30,000 inf.u), and 100% of the animals vaccinated with $3\times10^4$, $3\times10^5$, or $3\times10^6$ inf.u were protected from a $100LD_{50}$ challenge of the NY99 strain of WNV (Table 2).

TABLE 1

Safety of PIVs in suckling mice.

| Inoculum[a] | Dose (inf.u)[b] | % Survival[c] | Average survival time[d] |
|---|---|---|---|
| WN PIV | 2,000,000 | 100 (9/9) | NA[e] |
| WNV TX02 | 0.2 | 56 (5/9) | 8.5 (+/−2.9) |
| WNV TX02 | 2 | 0 (0/9) | 5.4 (+/−0.5) |
| WNV TX02 | 20 | 0 (0/8) | 6 (+/−0) |
| WNV TX02 | 200 | 0 (0/10) | 4.9 (+/−0.3) |
| YF PIV | 2,000,000 | 100 (10/10) | NA[e] |
| YFV 17D | 0.2 | 89 (8/9) | 8 (+/−0) |
| YFV 17D | 2 | 56 (5/9) | 7 (+/−0) |

TABLE 1-continued

Safety of PIVs in suckling mice.

| Inoculum[a] | Dose (inf.u)[b] | % Survival[c] | Average survival time[d] |
|---|---|---|---|
| YFV 17D | 20 | 11 (1/9) | 6.9 (+/−2.4) |
| YFV 17D | 200 | 0 (0/12) | 6 (+/−0) |

[a]Inoculated preparation, diluted in culture media with 10% FBS
[b]Delivered by i.c. route in a volume of 20 ml/animal
[c]Survival at 14 days postinoculation (live/dead)
[d]Average survival time from animals that died from infection (standard deviation)
[e]Not applicable

TABLE 2

Safety, potency and efficacy of PIV in adult mice

| Inoculum[a] | Dose (inf.u)[b] | % Survival[c] | Average survival time[d] | NEUT titer[e] | % Protection[f] |
|---|---|---|---|---|---|
| none (diluent) | 0 | 100 (8/8) | NA[g] | <1:40[h] | 14 (1/7) |
| WN PIV | 30,000 | 100 (10/10) | NA[g] | 1:40 | 100 (8/8) |
| WN PIV | 300,000 | 100 (10/10) | NA[g] | 1:160 | 100 (8/8) |
| WN PIV | 3,000,000 | 100 (10/10) | NA[g] | 1:160 | 100 (8/8) |
| WNV TX02 | 1 | 40 (4/10) | 8.5 (+/−1.4) | | |
| WNV TX02 | 10 | 30 (3/10) | 8 (+/−1.2) | | |
| WNV TX02 | 100 | 10 (1/10) | 7.8 (+/−1.4) | | |

[a]Inoculated preparation, diluted in culture media with 10% FBS.
[b]Delivered by i.p. route in a volume of 100 ml/animal.
[c]Survival at 14 days postinoculation (live/dead).
[d]Average survival time from animals that died from infection (standard deviation).
[e]NEUT titer of pooled sera collected from 2 animals at 21 days postinoculation (titer shown is the highest dilution giving 80% reduction of WNV foci formation).
[f]Protection from challenge with 100 LD$_{50}$ of the NY99 strain of WNV demonstrated by survival at 14 days post-challenge; single survivor from the diluent-inoculated group showed signs of disease (hunched back, ruffled fur, and malaise) from days 8-14. None of the PIV inoculated animals displayed any signs of disease in the 14-day postchallenge observation period.
[g]Not applicable.
[h]NEUT liters in sera from unimmunized mice tested side-by-side with sera from the WN PIV-inoculated mice.

Example 17

Further Modifications to Increase the Yield and Safety of PIVs/RepliVAX

Figure 9:
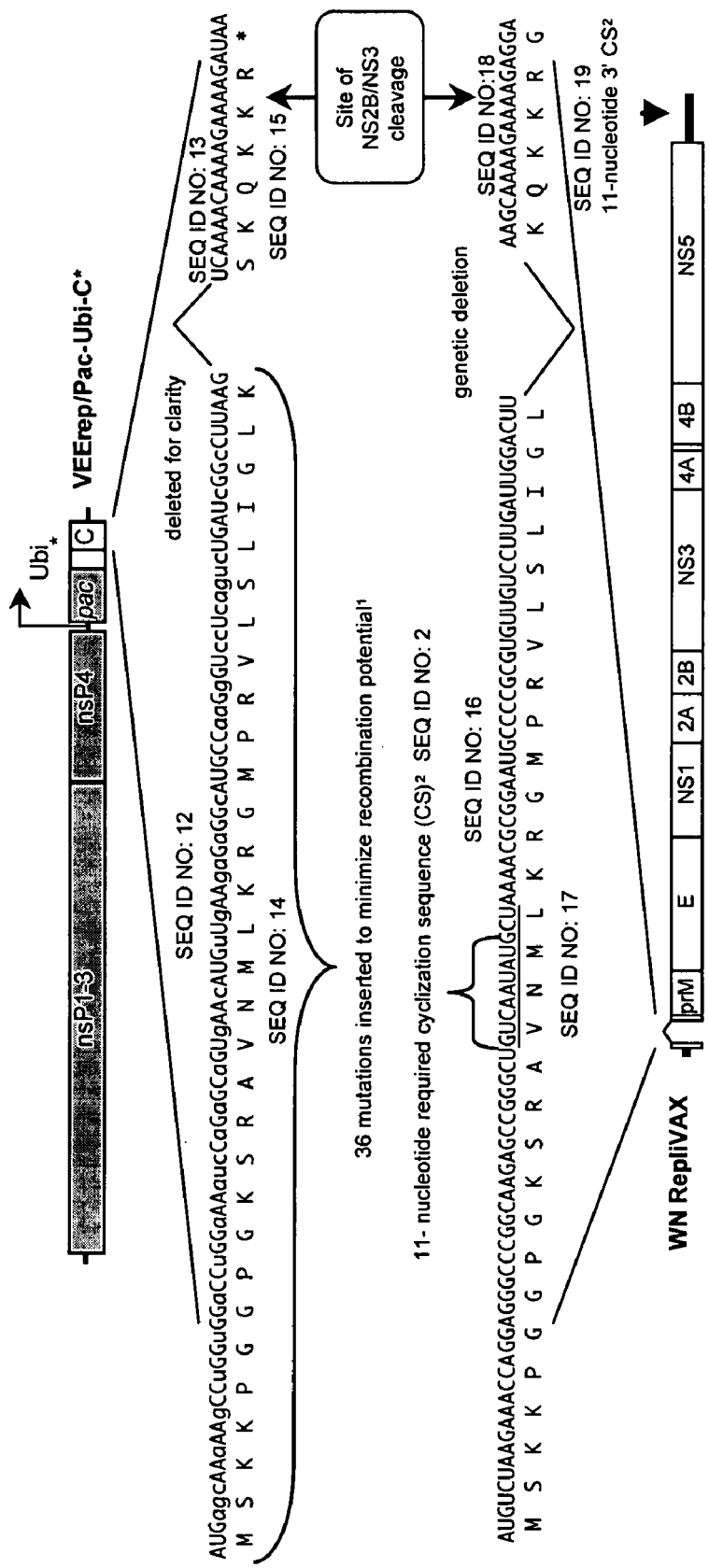
FIG. 9 shows a schematic representation of overlapping regions of RepliVAX and the VEE replicon used to provide C in trans. [1]Thirty-six mutations were inserted into the VEErep/pac-Ubi-C* to minimize homologous recombination with the fragment of C encoded by the RepliVAX genome. [2]Position of 5' and 3' CS sequences in the RepliVAX genome.

The present invention demonstrates that repeated passaging of RepliVAX did not result in recombination, but variants with enhanced growth were selected: The WNV RepliVAX has been repeatedly passaged on a cell line that encodes the WNV C protein. This C protein was produced by fusing a copy of the WNV C gene to a Pac gene driven by the subgenomic promoter of a non-cytopathic VEErep (Petrakova et al., 2005). In the resulting construct (VEErep/Pac-Ubi-C*), the ubiquitin (Ubi) gene was inserted in front of the C gene, and C was followed by a stop codon. In this context, a Pac-Ubi fusion protein would be produced along with a mature C protein (lacking the hydrophobic anchor; see FIG. 9). The C gene in this VEErep (denoted as "C*") was further modified by insertion of 36 mutations that ablate the CS signal, converting this 11-base region from GUCAAUAUGCU (SEQ ID NO: 2) to GUgAAcAUGuU (SEQ ID NO: 3) while maintaining C coding capacity. This large number of mutations dramatically reduces the likelihood of homologous recombination, and furthermore, if recombination did occur between the genomes, the production of a replicationally active genome could not occur, since the resulting RNA would have unmatched CSs, preventing replication (FIG. 9).

To test for the unlikely possibility of productive recombination, a clonal cell line was derived from BHK cells expressing VEErep/Pac-Ubi-C* {BHK(VEErep/Pac-Ubi-C*)}, and this cell line was used to passage the WN RepliVAX 10 times (in each case with infection at an MOI of 0.01), and the resulting RepliVAX was characterized in detail. To determine if this passage 10-(p10) population contained any live virus, Vero cell monolayers were infected at multiplicities of 0.1, 1, and 10 with the p10 WN RepliVAX, and washed extensively to remove extracellular RepliVAX. These monolayers were re-washed 24 hours later, and then harvested 2 days later. Passage of supernatant fluids from these cultures onto fresh Vero cell cultures failed to reveal any immunopositive cells when stained with a highly sensitive polyclonal antibody for WNV, indicating that RepliVAX had not productively recombined with the C protein encoded by the packaging cell line.

Interestingly, when the p10 WN RepliVAX was compared to p0 RepliVAX on the BHK(VEErep/Pac-Ubi-C*) cell line, the p10 RepliVAX produced polymorphic foci of infection, many of which were much larger than those produced by the p0 RepliVAX (FIG. 10). Furthermore, p10 RepliVAX replicates 10 times higher than p0 RepliVAX at early time points, with an endpoint titer twice as high.

Analyses of the PCR products obtained from cDNA produced from Vero cells infected with this p10 RepliVAX demonstrated that there were no products that contained a full-length C coding region. However, sequence analyses of the C-prM junction of the product spanning these regions revealed that two mutations had arisen during passaging. As expected from the heterogeneous nature of the foci produced by the p10 RepliVAX on the packaging cells (FIG. 10), both mutations were present as mixtures with the original RepliVAX sequence. One of the mutations, which appeared to be present over half of the nucleic acid population in these sequence reactions (sequenced in both directions), consisted of a AGC>uGC (S>C) mutation at the P4 position preceding the signal peptidase cleavage site (S(c)VGA|VTLS (SEQ ID NO: 4) in the RepliVAX genome. The second mutation, which was present in only about 30% of the amplified sequences (again in reactions completed in both directions) consisted of an AAG>AuG (K>M) at position P3 following the NS2B/NS3 cleavage site (QKKR|GGK(m)T) (SEQ ID NO: 5). Although these mutations are in the position of the deleted SL5, they do not alter predicted RNA structures. The rapid selection (only 10 growth cycles) of a better-growing RepliVAX is very exciting since it indicates that selection of better-growing variants is a powerful method to improve RepliVAX. The positions of these mutations was not unexpected since it is known that altering efficiency of NS2B/NS3 versus signal peptidase cleavage can influence flavivirus particle yield and infectivity (Keelapang et al., 2004; Lee et al., 2000; Lobigs and Lee, 2004; Yamschikov et al., 1997). Studies are continuing on selection of even better growing variants, and these two mutations are being targeted for insertion into second-generation RepliVAX constructs, to confirm their ability to work separately (or together) to improve RepliVAX yield and antigen production. Nevertheless, the data presented herein indicate that under these passage conditions: 1) no recombination occurred, 2) positive selection could be used to produce improved RepliVAXs.

Blind passage of JE RepliVAX similarly yielded better-growing variants with mutations in the same regions of the genome. The ability to blind passage RepliVAX products to produce better growing variants is a key feature of this invention, and a clear advantage over traditional LAV, where production of better-growing variants is always complicated by the concern that these better-growing variants may have lost their attenuation in man.

Furthermore, the mutated, improved C-expression cassette (VEErep/Pac-Ubi-C*), which has been shown to be stable, and demonstrated freedom from recombination when used in a BHK cell line (not approved for human vaccine generation), has also been shown to be stable and useful for PIV propagation when introduced into Vero cells (an accepted cell line for the production of human vaccines). Specifically, RNAs corresponding to the VEE replicon have been introduced Vero cells from a certified seed using the same methods applied to BHK cells. Following introduction of the RNA into these Vero cells, the cells were maintained in serum free media (an important issue for vaccine generation) containing puromycin, and these cells were shown to be useful for PIV propagation. Under these propagation conditions, these cells have been shown to produce slightly lower titers of PIV than similarly derived BHK cells, but the VEErep/Pac-Ubi-C*-Vero cells hold up better under these culture conditions, permitting multiple harvests. FIG. 11 shows the production of PIV from these cells can be obtained for multiple harvests under serum-free conditions.

In summary, propagation of PIVs in cell lines that express C (especially C cassettes that contain the signal sequence of prM, or this region plus portions of the prM and E genes) can theoretically recombine with the PIV genome, producing a live virus that could cause disease, increasing the risk of the method of vaccine generation. To overcome this problem, the present invention demonstrated that cell lines for the propagation of WN PIV can be produced using a C protein that ends precisely at the NS2B/NS3 cleavage site, minimizing the chance of recombination at this region of the PIV genome, providing an advantage over other propagation methods in which cell lines encode RNAs that encode the portion of the anchor of C (that is also know as the signal peptide of prM) that are shared by the PIV.

To further enhance the safety of this C-expression cassette, the present invention demonstrated that the portion of the cassette that is used to make the VEErep-encoded C that complements the PIV genome (namely the first 30 codons encoding the amino acid sequence that are required to produce a replicating PIV genome due to underlying RNA elements required for viral replication) could be specifically mutated to produce a cassette that differs from the PIV genome at 36 nucleotide positions (introduced without altering the protein product) resulting in a C gene that has a dramatically reduced probability of recombination with the PIV genome (FIG. 9). Furthermore, this mutated C gene was created to have three mutations in the cyclization signal (CS) that must be complementary to a CS in the 3'UTR of the PIV genome to allow viral replication, providing a further safety feature to prevent recombination (FIG. 9). Finally, this C gene was inserted into the VEEreplicon following the selectable marker gene (pac), by using a ubiquitin gene to the intact C product from the resulting polyprotein (alternative self-cleaving sequences such as the auto-proteinase 2A of FMDV, or other related sequences could easily be substituted for ubiquitin). Creation of this single-polyprotein cassette provides the advantage of producing a genetically more stable VEEreplicon, reducing the chance of recombination within the propagating cell lines, eliminating the C-expression cassette, and reducing PIV yield. The resulting construct (VEErep/Pac-Ubi-C*, FIG. 9) was introduced into BHK cells, and the cells were used to produce a clonal cell line expressing the VEE replicon using established methods (Fayzulin et al., Virology 2006).

One clonal cell line was examined after 18 passages from single-cell cloning, and found to have no evidence of any genetic deletion of the C cassettes (by RT-PCR), nor was it found to have any detectable mutations within the C-expression cassette. Most importantly, this cell line displayed similar ability to propagate the WNV PIV at a passage level as high as 41. Finally, following 10 passages of PIV on this cell line, no evidence of recombination producing PIV-recombinants capable of productive replication on cells that do not express the C cassette (namely WT Vero cells), and no evidence of introduction of C-encoding sequences into the PIV genome by RT PCR was observed.

Figure 12A:
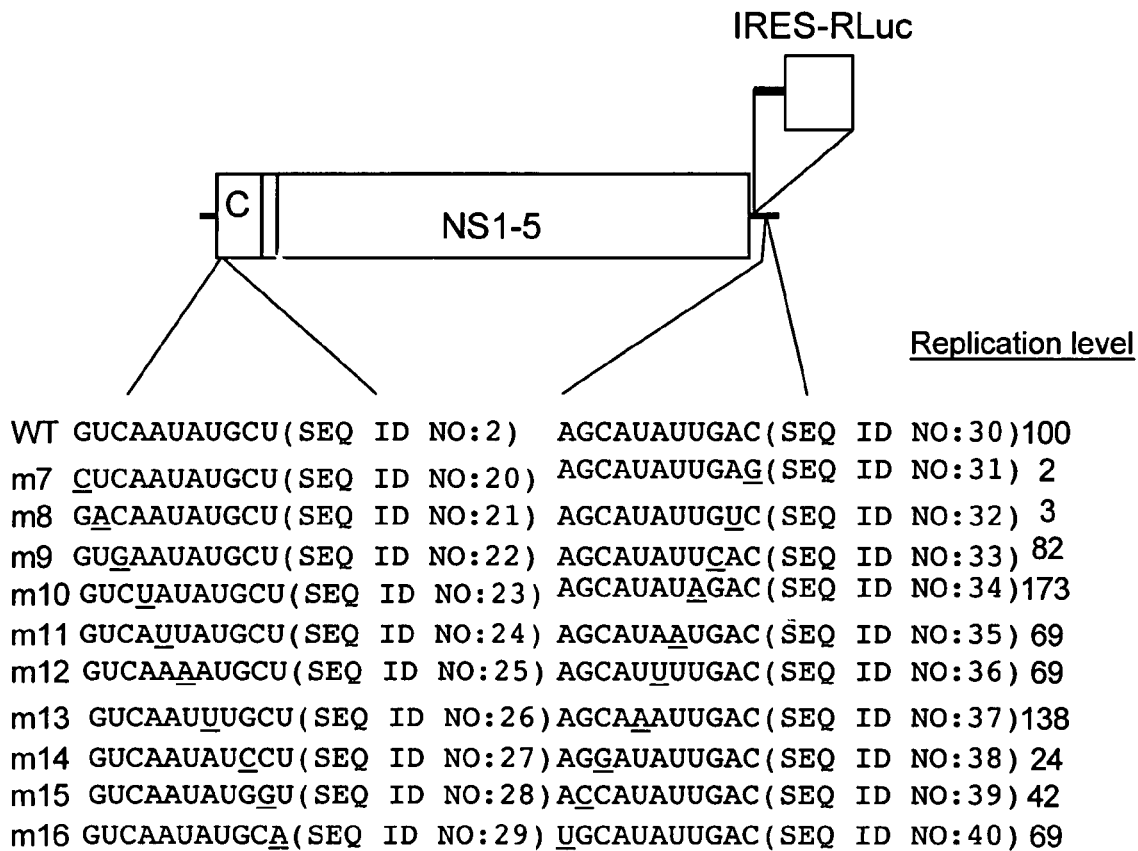
FIGS. 12A-12B show cyclization mutants.
Figure 12B:
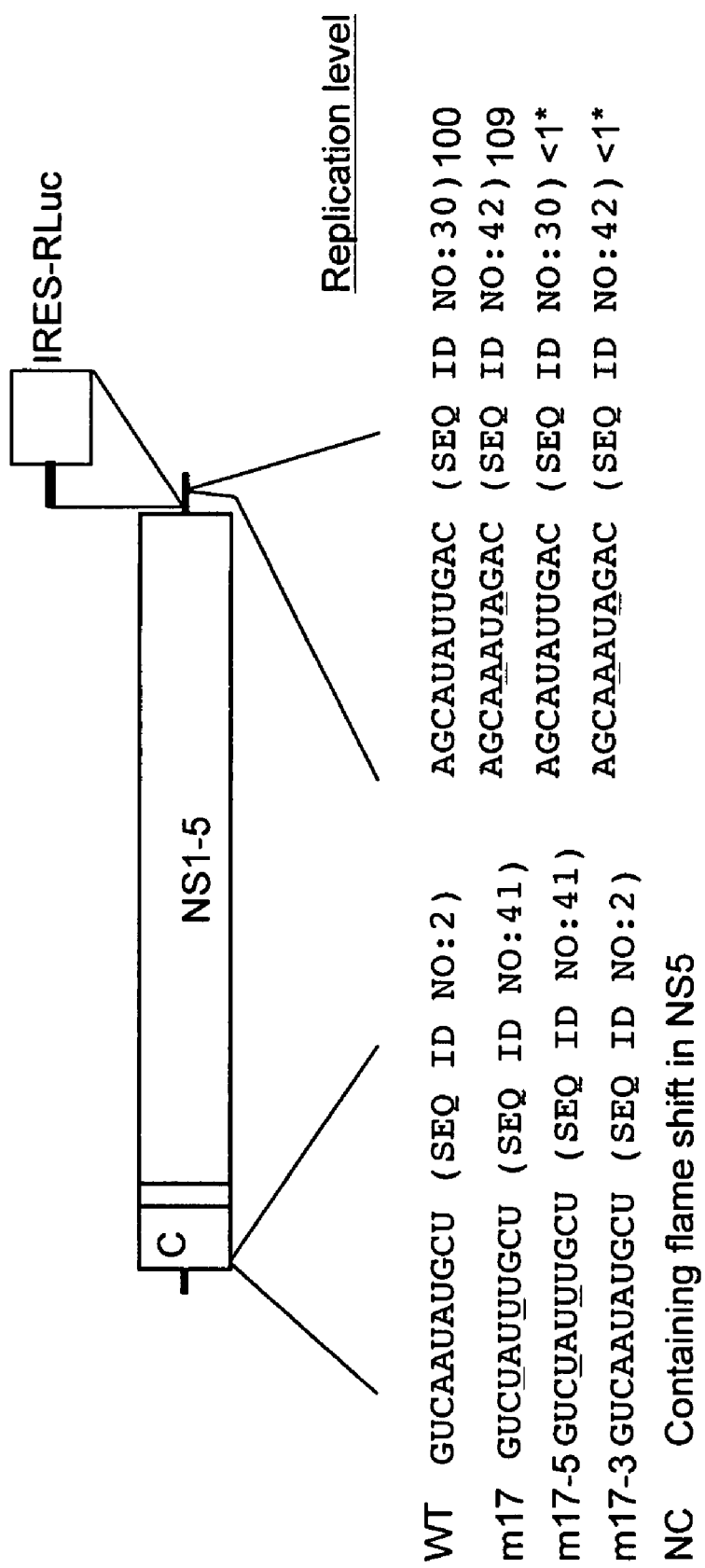

Furthermore, to address concerns that PIV might recombine with flaviviruses in vaccines at the time of their vaccination, producing novel, virulent flaviviruses, the present invention demonstrated that WNV genomes with "unnatural" cyclization signals (CS) present in all known naturally circulating flaviviruses, can be generated that replicate to high levels. Evidence has been produced in several laboratories that the two CS found at the 5' and 3' ends of the genomes of all flaviviruses must be 100% complementary to provide productive viral replication (Khromykh et al. J. Virol., 2001; Lo et al., J. Virol., 2003; Alvarez et al., Virol., 2003). These studies also demonstrated that unnatural CSs could produce replicating genomes, as long as the CS were 100% complementary. However these investigators reported that all genomes with unnatural CS sequences had replication defects. By systematic analysis of CS in WNV genomes, specifically the testing the ability of carefully selected single base swaps to produce high-level replication, single-base changes, and subsequent double-base changes that permit high-levels of genome replication (FIG. 12A) were identified. FIG. 12B demonstrates that high-level replication of WNV genome with two-base substitutions is possible, and that genomes intentionally created with mismatched CS sequences (namely WT and the 2-base mutant) are not replicationally active. This mutation, and others like it, can therefore be utilized to produce PIV with a superior safety profile, since any recombinant virus resulting from a single-point genetic recombination between the CS-modified PIV vaccine and a virus circulating in areas where people are undergoing vaccination would not be replicationally active, and hence could not cause disease.

Example 18

BHK Cells Expressing WNV C Gene Maintain their Phenotype for Multiple Passages

Studies with a WNV C-expressing clonal cell line derived from BHK cells transfected with VEErep/Pac-Ubi-C* has demonstrated its long-term stability and utility in generating RepliVAX for several reasons. Firstly, these cells were useful for repeated passaging of RepliVAX. Secondly, side-by side focus-formation assays on cells at two different passage levels (passages 8 & 24 after single-cell cloning) showed indistinguishable WN RepliVAX titers and foci sizes. Finally, direct analysis of the sequence of the C-encoding cassette in these cells at the passage-24 level revealed no changes relative to the original VEErep sequence. Taken together these data indicate that cells harboring C-expressing VEEreps should be stable enough for use in the currently accepted master cell seed lot format used to produce human vaccines. Furthermore, the fact that VEEreps have already been used in human trials, make it likely that the application of the

Example 19

Lymphoid Tissue Targeting of WNV VLPs

As indicated supra, WNV VLPs are similar to RepliVAX, except in place of the flavivirus prM/E proteins, they can encode a reporter gene, or they can simply contain a flavivirus replicon without a reporter. VLPs can be readily produced in packaging cells expressing all three WNV structural proteins, and have been produced at high titer (Fayzulin et al., 2006). When $10^7$ U of VLP were inoculated into mice, these animals produced 1,000 to 5,000 U/ml of type I interferon (IFN) in their serum 24 hr post-inoculation. IFN responses were produced by both ip and subcutaneous footpad injection (fp). Furthermore, popliteal lymph nodes dissected 24 hrs after fp inoculation with b-galactosidase-expressing VLPs contained large numbers of b-galactosidase-positive cells, indicating that VLPs, which enter cells in a manner indistinguishable from RepliVAX, are targeting important lymph organs. This result is consistent with the high levels of IFN elicited by VLP-injection and suggests that similar targeting is responsible for the high potency and efficacy of RepliVAX.

The following references were cited herein:
Aberle, J. H. et al., 1999, *J Immunol* 163, 6756-61.
Aberle, J. H. et al., 2005, *J Virol* 79, 15107-13.
Bredenbeek, P. J. et al., 2003 *J Gen Virol* 84, 1261-8.
Chambers, T. J. et al., 1999 *J Virol* 73, 3095-101.
Clyde and HArris, 2006, J Virol 80: 2170-2182.
Colombage, G. et al. 1998, *Virology* 250, 151-63.
Davis, B. S. et al., 2001, *Journal of Virology* 75, 4040-4047.
Fayzulin et al., 2006, Virology 351: 196-209.
Filomatori et al., 2006, Genes Dev 20: 2238-2249.
Fonseca, B. A., et al., 1994, *Vaccine* 12, 279-85.
Gentry, M. K et al., 1982, *Am J Trop Med Hyg* 31, 548-55.
Gerasimon, G., and Lowry, K., 2005, *South Med J* 98, 653-6.
Haas, J., et al., 1996 *Curr Biol* 6, 315-24.
Hall, R. A., et al., 2003, *Proc Natl Acad Sci USA* 100, 10460-10464.
Huang, C. Y., et al., 2003, *J Virol* 77, 11436-47.
Kanesa, T. N., et al., 2000 *Vaccine* 19, 483-491.
Keelapang et al., 2004, J Virol 78: 2367-2381.
Kochel, T et al., 1997, *Vaccine* 15, 547-52.
Kochel, T. J. et al., 2000. *Vaccine* 18, 3166-3173.
Kofler, R. M., et al., 2004, *Proc Natl Acad Sci USA* 101, 1951-6.
Konishi, E., and Fujii, A., 2002, *Vaccine* 20, 1058-67.
Konishi, E et al., 2001 *Journal of Virology* 75, 2204-2212.
Konishi, E et al., 1992a *Virology* 190, 454-8.
Konishi, E et al., 1992b, *Virology* 188, 714-20.
Konishi, E et al., 2000a, *Vaccine*. January 18, 1133-1139.
Konishi, E. et al., 2000b, *Virology* 268, 49-55.
Lee et al., 2000, J Virol; 74: 24-32.
Lemm, J. A et al., 1990, *J Virol* 64, 3001-11.
Liljestrom, P et al., 1991 *J Virol* 65, 4107-13.
Lobigs and Lee, 2004, J Virol 78: 178-186.
Lindenbach et al., 2001, 2001, Flaviviridae: the viruses and their replication Knipe et al., (Eds. $4^{th}$ Ed. Fields Virology, Vol. 1, Lippincott Williams and Wilkins, Philadelphia., pp. 991-1041(2 vols)).
Lorenz, I. C. et al., 2002 *J Virol* 76, 5480-91.
Mason, P. W. et al., 1991, *Virology* 180, 294-305.
Minke, J. M. et al., 2004, *Arch Virol Suppl,* 221-30.
Mishin, V. P. et al., 2001 *Virus Research* 81, 113-123.
Monath, T. P. 1991, *Am J Trop Med Hyg* 45, 1-43.
Monath, T. P. et al., 2002 *Vaccine* 20, 1004-18.
Petrakova, O et al., 2005 *J Virol* 79, 7597-608.
Phillpotts, R. J. et al., 1996 *Arch Virol* 141, 743-9.
Pincus, S., et al., 1992 *Virology* 187, 290-7.
Pletnev et al., 2002, *Proc. National Academy of Sciences USA* 99, 3036-3041.
Pugachev, K. V. et al., 2004 *J Virol* 78, 1032-8.
Pugachev, K. V., et al., 1995 *Virology* 212, 587-94.
Qiao, M. e al., 2004 *J Infect Dis* 190, 2104-8.
Rossi, S. L. et al, 2005, *Virology* 331, 457-70.
Schalich et al., 1996, Virology, 70: 4549-4557.
Schmaljohn, C. et al., 1997, *J Virol* 71, 9563-9.
Scholle, F. et al., 2004, *J Virol* 78, 11605-14.
Volkova, E. et al., 2006, *Virology* 344, 315-27.
Xiao, S. Y. et al. 2001, *Emerging Infectious Diseases* July August 7, 714-721.
Yamshchikov, V. F., and Compans, R. W., 1994), *J Virol* 68, 5765-71.
Yamshchikov et al., 1997, J Virol, 71: 4364-4371.
Zuker, 2003, Nucleic Acid Res 31: 3406-3415.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A replication-deficient pseudoinfectious virus comprising:
a West Nile or Yellow Fever deletion mutant genome comprising a deletion within the nucleotide sequence encoding amino acids 26 to 100 of the capsid protein, wherein the deletion mutant genome cannot produce capsid-containing viral particles in a cell that does not express a capsid protein, wherein the deletion does not disrupt the maturation of the prM protein or the RNA sequence required for genome cyclization, and a complementary capsid protein.

2. The replication-deficient pseudoinfectious virus of claim 1, wherein said virus is a chimeric virus comprising a heterologous prM-E cassette.

3. The replication-deficient pseudoinfectious virus of claim 2, wherein the heterologous prM-E cassette is from a yellow fever virus, as West Nile virus, a dengue virus, a tick-borne encephalitis virus, a Saint Louis encephalitis virus, a Japanese encephalitis virus, or a Murray Valley encephalitis virus.

4. The replication-deficient pseudoinfectious virus of claim 1, wherein the deletion is of amino acids 26 to 93, 31-93, 31-100, or 26 to 100 of the capsid protein.

5. The replication-deficient pseudoinfectious virus of claim 1, wherein said deletion mutant genome further encodes a marker protein or an antigen.

6. The replication-deficient pseudoinfectious virus of claim 5, wherein the marker protein is a green fluorescent protein.

7. A cell culture system comprising:
a West Nile or Yellow Fever deletion mutant genome comprising a deletion within the nucleotide sequence encoding amino acids 26 to 100 of the capsid protein, wherein the deletion mutant genome cannot produce capsid-containing viral particles in a cell that does not express a capsid protein, and wherein the deletion does not disrupt the maturation of the prM protein or the RNA sequence required for genome cyclization; the deletion mutant genome being inside a cell that expresses a complementary capsid protein, wherein the cell does not express prM or envelope proteins.

8. The cell culture system of claim 7, wherein the cell comprises a replicon encoding a codon-optimized version of the complementary capsid protein.

9. The cell culture system of claim 7, wherein the cell comprises an alphavirus replicon encoding the complementary capsid protein.

10. The cell culture system of claim 9, wherein the alphavirus is Venezuelan Equine Encephalitis Virus.

11. A method of producing a replication-deficient pseudoinfectious virus comprising:
providing a West Nile or Yellow Fever deletion mutant genome comprising a deletion within the nucleotide sequence encoding amino acids 26 to 100 of the capsid protein, wherein the deletion mutant genome cannot produce capsid-containing viral particles in a cell that does not express a capsid protein, wherein the deletion does not disrupt the maturation of the prM protein or the RNA sequence required for genome cyclization;
providing a cell that expresses a complementary capsid protein;
inserting the deletion mutant genome into the cell; and
culturing the cell to produce a replication-deficient pseudoinfectious virus.

12. The method of claim 11, wherein the deletion mutant genome comprises a heterologous prM-E cassette.

13. The method of claim 12, wherein the heterologous prM-E cassette is from a yellow fever virus, a West Nile virus, a dengue virus, a tick-borne encephalitis virus, a Saint Louis encephalitis virus, a Japanese encephalitis virus, or a Murray Valley encephalitis virus.

14. The method of claim 11, wherein the cell comprises a genetically engineered replicon derived from a viral vector.

15. The method of claim 14, wherein the replicon encodes a codon-optimized version of the complementary capsid protein.

16. The method of claim 14, wherein the replicon comprises the unnatural cyclization sequence of SEQ ID NO:3.

17. The method of claim 11, wherein the deletion mutant genome comprises one or both of altered C-prM junction sequences SEQ ID NO:4 and SEQ ID NO:5.

18. The method of claim 11, wherein inserting the deletion mutant genome into the cell comprises transfecting with in vitro synthesized replicon RNAs, transfecting with plasmid DNAs designed to synthesize functional alphaviral replicons from cellular RNA-polymerase II-specific promoter, or by infecting with alphaviral replicons packaged inside alphaviral structural proteins.

19. The method of claim 14, wherein the replicon is an alphavirus replicon.

20. The method of claim 19, wherein the alphavirus is Venezuelan Equine Encephalitis Virus, Sindbis virus, Eastern Equine Encephalitis virus, Western Equine Encephalitis virus, or Ross River virus.

21. A pharmaceutical composition, comprising the replication-deficient pseudoinfectious virus of claim 1.

22. The replication-deficient pseudoinfetious virus of claim 1, wherein the deletion mutant genome comprises one or both of altered C-prM junction sequences SEQ ID NO:4 and SEQ ID NO:5.

23. The method of claim 11, wherein the cell does not express prM or envelope proteins.

24. The cell culture system of claim 8, wherein the replicon comprises the unnatural cyclization sequence of SEQ ID NO3.

25. The cell culture system of claim 7, wherein the cell further expresses a marker gene.

* * * * *